US012297461B2

(12) United States Patent
Liu et al.

(10) Patent No.: US 12,297,461 B2
(45) Date of Patent: May 13, 2025

(54) METHODS OF PRODUCING AND CHARACTERIZING VIRUS VACCINE AND VIRUS VACCINE COMPOSITION

(71) Applicants: Guangzhou Realbenefitspot Pharmaceutical Co., Ltd., Guangzhou (CN); Guangzhou Yinheyangguang Biologics Co., Ltd., Guangzhou (CN)

(72) Inventors: Dianlian Liu, Guangzhou (CN); Wen Ai, Guangzhou (CN); Mingfeng Shen, Guangzhou (CN)

(73) Assignees: Guangzhou Realbenefitspot Pharmaceutical Co., Ltd., Guangzhou (CN); Guangzhou Yinheyangguang Biologics Co., Ltd., Guangzhou (CN)

( * ) Notice: Subject to any disclaimer, the term of this patent is extended or adjusted under 35 U.S.C. 154(b) by 0 days.

(21) Appl. No.: 17/707,613

(22) Filed: Mar. 29, 2022

(65) Prior Publication Data
US 2022/0333085 A1    Oct. 20, 2022

Related U.S. Application Data

(63) Continuation of application No. 16/268,250, filed on Feb. 5, 2019, now Pat. No. 11,319,529, which is a
(Continued)

(30) Foreign Application Priority Data

Mar. 6, 2017   (CN) .......................... 201710139497.9
Mar. 6, 2017   (CN) .......................... 201710139533.1
(Continued)

(51) Int. Cl.
*C12N 7/00* (2006.01)
*A61K 39/12* (2006.01)
(Continued)

(52) U.S. Cl.
CPC ................ *C12N 7/00* (2013.01); *A61K 39/12* (2013.01); *B01D 15/363* (2013.01);
(Continued)

(58) Field of Classification Search
None
See application file for complete search history.

(56) References Cited

U.S. PATENT DOCUMENTS 6,143,548 A    11/2000   O'Riordan et al.
6,149,917 A    11/2000   Fanget et al.
(Continued)

FOREIGN PATENT DOCUMENTS

CN        1199419 A      11/1998
CN        101189326 A    5/2008
(Continued)

OTHER PUBLICATIONS

Li SM, Bai FL, Xu WJ, Yang YB, An Y, Li TH, Yu YH, Li DS, Wang WF. Removing residual DNA from Vero-cell culture-derived human rabies vaccine by using nuclease. Biologicals. Sep. 2014;42(5):271-6. (Year: 2014).*
(Continued)

*Primary Examiner* — Shanon A. Foley
(74) *Attorney, Agent, or Firm* — MORRISON & FOERSTER LLP

(57) ABSTRACT

This application pertains to methods of isolating virus particles and producing virus vaccine composition comprising subject a biological sample to an anion exchange chromatography and a hydroxyapatite chromatography. The application also pertains to rabies virus vaccine compositions and methods of assessing suitability of a virus vaccine composition or releasing a commercial batch of virus vaccine composition for clinical use.

31 Claims, 10 Drawing Sheets

Related U.S. Application Data continuation of application No. 16/125,492, filed on Sep. 7, 2018, now Pat. No. 10,260,050, which is a continuation of application No. PCT/CN2018/077905, filed on Mar. 2, 2018.

(30) Foreign Application Priority Data

| Apr. 25, 2017 | (CN) | .......................... 201710298490.1 |
| Apr. 25, 2017 | (CN) | .......................... 201710298557.1 |

(51) Int. Cl.

| B01D 15/36 | (2006.01) |
| B01J 20/04 | (2006.01) |
| C07K 1/18 | (2006.01) |
| C07K 1/20 | (2006.01) |
| C07K 1/22 | (2006.01) |
| C07K 1/36 | (2006.01) |
| C07K 14/005 | (2006.01) |
| C12N 7/02 | (2006.01) |
| G01N 30/02 | (2006.01) |

(52) U.S. Cl.
CPC .............. *B01J 20/048* (2013.01); *C07K 1/18* (2013.01); *C07K 1/20* (2013.01); *C07K 1/22* (2013.01); *C07K 1/36* (2013.01); *C07K 14/005* (2013.01); *C12N 7/02* (2013.01); *G01N 30/02* (2013.01); *C12N 2760/16034* (2013.01); *C12N 2760/20134* (2013.01); *C12N 2760/20151* (2013.01); *C12N 2770/24134* (2013.01); *G01N 2030/022* (2013.01)

(56) References Cited

U.S. PATENT DOCUMENTS

| 8,961,997 | B2 | 2/2015 | Fabre et al. | |
| 10,260,050 | B2 | 4/2019 | Liu et al. | |
| 11,319,529 | B2 | 5/2022 | Liu et al. | |
| 2003/0092145 | A1 | 5/2003 | Jira et al. | |
| 2009/0247735 | A1 | 10/2009 | Gagnon et al. | |
| 2010/0260798 | A1* | 10/2010 | Fabre .................. | A61K 39/205 |
| | | | | 435/238 |
| 2014/0004145 | A1 | 1/2014 | Taylor | |
| 2019/0002839 | A1 | 1/2019 | Liu et al. | |
| 2019/0270970 | A1 | 9/2019 | Liu et al. | |

FOREIGN PATENT DOCUMENTS

| CN | 101974490 A | 2/2011 |
| CN | 102171334 A | 8/2011 |
| CN | 102327608 B | 3/2013 |
| CN | 104353608 A | 2/2015 |
| CN | 102171334 B | 5/2015 |
| CN | 105378074 A | 3/2016 |
| CN | 105907729 A | 8/2016 |
| EP | 0171771 A2 | 2/1986 |
| EP | 2351835 A1 | 8/2011 |
| WO | WO2005093049 A1 | 10/2005 |
| WO | WO2006136566 A1 | 12/2006 |
| WO | WO2010065520 A1 | 6/2010 |
| WO | WO2011011390 A1 | 1/2011 |
| WO | WO2012061815 A2 | 5/2012 |

OTHER PUBLICATIONS

Kurosawa et al. Mammalian Virus Purification Using Ceramic Hydroxyapatite. Bio-Rad Bulletin 6549. 2014. (Year: 2014).*

Anonymous. (Date Unknown). "Chromatography CHT™ Ceramic Hydroxyapatite: A Matrix with Unique Separation Properties and Unparalleled Selectivity and Resolution", *Bulletin 5667, Bio-Rad Brochure*, 2 pages.

Bio-Rad Laboratories, Inc. (Date Unknown). "CHT™ Ceramic Hydroxyapatite", *Instruction Manual*, Bio-Rad Life Science Group, 43 pages.

Dietzschold, B. (Jan. 2015). "Purification of Rabies Virus and Its Subunits," Current Laboratory Techniques in Rabies Diagnosis, Research and Prevention 2:47-56.

Gagnon, P. (Apr. 1, 2010). "Hydroxyapatite for Biomolecule Purification With Development Pathways Determined, HA Has Become a Mainstream Industrial Staple", *Gen. Engineering Biotech. News* 30(7):4 pages.

Gagnon, P. (Dec. 15, 2009). "Chromatographic Purification of Virus Particles," *Encyclopedia* of Industrial Biotechnology: Bioprocess, Bioseparation, and Cell Technology, edited by Michael C. Flickinger, 2009, John Wiley & Sons, pp. 1-20, 20 pages.

Gagnon, P. (Jun. 2009). "Monoclonal Antibody Purification with Hydroxyapatite", *New Biotechnology* 25(5):287-293.

Gagnon, P. et al. (Date Unknown). "Chromatography: CHT™ Ceramic Hydroxyapatite—A New Dimension in Chromatography of Biological Molecules", *Bulletin 2156, Bio-Rad Brochure*, 2pages.

International Preliminary Report on Patentability issue date of Sep. 10, 2019 for Patent Application No. PCT/CN2018/077905, filed Mar. 2, 2018, 6 pages.

International Search Report mailed Jun. 7, 2018, for PCT Patent Application No. PCT/CN2018/077905, filed Mar. 2, 2018, 7 pages.

Kang, H. et al. (Mar. 11, 2015). "Chimeric Rabies Virus-Like Particles Containing Membrane-Anchored GM-CSF Enhances the Immune Response Against Rabies Virus," Viruses 7(3):1134-1152.

Kuiper, M. et al. (Nov. 20, 2002). "Purification of A Functional Gene Therapy Vector Derived From Moloney Murine Leukemia Virus Using Membrane Filtration and Ceramic Hydroxyapatite Chromatography," Biotechnology and Bioengineering 80(4):445-453.

Kurosawa, Y et al. (2000). "Mammalian Virus Purification Using Ceramic Hydroxyapatite", *Bulletin 6549, Bio-Rad Brochur*, 6 pages.

Kurosawa, Y. et al. (2012, e-pub. Aug. 2012). "Purification of Dengue Virus Particles By One-Step Ceramic Hydroxyapatite Chromatography," World Journal of Vaccines 2(3):155-160.

Michen, B. et al. (2010). "Isoelectric Points of Viruses," Journal of Applied Microbiology 109(2):388-397.

Navaratnarajah (2008). "Assembly of Viruses: Enveloped Particles," Encyclopedia of Virology, pp. 193-200, 9 pages.

Ng, P. et al. (2008). "Chromatography: How CHT™ Ceramic Hydroxyapatite Works", *Bulletin 5709, Bio-Rad Brochure*, 4 pages.

Pato, T.P. et al. (2014, e-pub. Mar. 11, 2014). "Development of a Membrane Adsorber Based Capture Step for The Purification of Yellow Fever Virus," Vaccine 32(24):2789-2793.

Sokol, F. et al. (Aug. 1968). "Purification of Rabies Virus Grown in Tissue Culture," J. Viral. 2(8):836-849.

Trabelsi, K. et al. (2019, e-pub. Jul. 9, 2019). "Purification of Rabies Virus Produced in Vero Cells Grown in Serum Free Medium," Vaccine 37(47):7052-7060.

Wang, B. et al. (Jun. 1, 2008). "Applications of Hydroxyapatite Chromatography in the Separation and Purification of Biomolecules," *Editorial Office of Journal of Pharmaceutical Analysis* 28(6):1009-1013. (English Abstract Only).

Wolff, M.W. et al. (2011, e-pub. Jan. 9, 2014). "Downstream processing of cell culture-derived virus particles," Expert Reviews 10(10):1451-1475.

Written Opinion of the International Searching Authority mailed Jun. 7, 2018, for PCT Patent Application No. PCT/CN2018/077905, filed Mar. 2, 2018, 5 pages.

* cited by examiner

METHODS OF PRODUCING AND CHARACTERIZING VIRUS VACCINE AND VIRUS VACCINE COMPOSITION

RELATED APPLICATIONS

This application is a Continuation patent applications of U.S. patent application Ser. No. 16/268,250, filed Feb. 5, 2019, which is a Continuation patent applications of U.S. patent application Ser. No. 16/125,492, filed Sep. 7, 2018, now U.S. Pat. No. 10,260,050, which is a Continuation Patent Applications of PCT/CN2018/077905, filed on Mar. 2, 2018 which claims priority benefit to Chinese Applications CN201710298490.1, filed Apr. 25, 2017, CN201710139497.9, filed Mar. 6, 2017, CN201710139533.1, filed Mar. 6, 2017, all of which are incorporated herein by reference in their entirety for all purposes. This application also claims priority benefit to CN201710298557.1, filed Apr. 25, 2017.

FIELD OF THE INVENTION

This application pertains to methods of isolating virus particles and producing virus vaccine composition. The application also pertains to rabies virus vaccine compositions and methods of assessing suitability of a virus vaccine composition for clinical use.

BACKGROUND OF THE INVENTION

Viruses can be divided into enveloped viruses (e.g., rabies virus) and non-enveloped viruses. Non-enveloped viruses only consist of the capsid protein and the viral genomic nucleic acids. They are generally homogenous in structure and easy to separate and purify. The enveloped viruses on the other hand, haves complicated structure and heterogeneity.

Enveloped viruses generally have a linear DNA or RNA in the inner core of the viral particles. The inner core is surrounded by a capsid, which is comprised of multiple nucleoprotein subunits. Together, the inner core and the capsid form a tightly-packed nucleocapsid particle. The nucleocapsid particle is wrapped by a lipid envelop on which one or more than one outer membrane protein is located. Each outer membrane protein has multiple copies on the surface and is densely distributed on the surface of the virus. The one or more outer membrane proteins are generally glycosylated to certain degree.

Current methods of purifying enveloped virus (e.g., rabies virus) are mainly based upon the different molecular sizes between the virus particle and impurities, for example, by using density gradient ultracentrifugation and/or gel filtration chromatography. However, impurities having a similar size as the viral particles cannot be separated by these methods. Therefore, there is a need for new methods of purifying enveloped viruses (e.g., rabies virus).

The disclosures of all publications, patents, patent applications and published patent applications referred to herein are hereby incorporated herein by reference in their entirety.

BRIEF SUMMARY OF THE INVENTION

The present application provides methods of purifying an enveloped virus from a biological sample, comprising subjecting the biological sample to an ion exchange ("IE") chromatography and a hydroxyapatite ("HA") chromatography. In some embodiments, the hydroxyapatite chromatography is carried out after the ion exchange chromatography. In some embodiments, the ion exchange chromatography is carried out after the hydroxyapatite chromatography.

In some embodiments according to any one of the methods described herein, the IE chromatography comprises: a) an optional IE pre-equilibration step, comprising pre-equilibrating an ion exchange column with an ion exchange pre-equilibrating buffer; b) an IE loading step, comprising loading the biological sample or a post-HA chromatography sample to the ion exchange column; c) an optionally IE equilibration step, comprising equilibrating the ion exchange column with an IE equilibrating buffer; d) an optional IE pre-elution step, comprising pre-eluting the ion exchange column with an IE pre-eluting buffer; and e) an IE elution step, comprising eluting the IE column with an IE elution buffer. In some embodiments, the method further comprises a second IE elution step comprising eluting the IE column with a second IE elution buffer. In some embodiments, a first IE eluate and a second IE eluate are collected from the first IE elution step and the second IE elution step, respectively, and wherein the first IE eluate and the second IE eluate comprise virus with different structure, purity or virus protein composition.

In some embodiments according to any one of the methods described herein, the HA chromatography comprises: a) an optional HA pre-equilibration step, comprising pre-equilibrating an HA column with an HA pre-equilibrating buffer; b) an HA loading step, comprising loading the biological sample or a post-IE chromatography sample to the HA column; c) an optionally HA equilibration step, comprising equilibrating the HA column with an HA equilibrating buffer; d) an optional HA pre-elution step, comprising pre-eluting the HA column with an HA pre-eluting buffer; and e) an HA elution step, comprising eluting the HA column with an HA elution buffer. In some embodiments, the method further comprises a second HA elution step comprising eluting the HA column with a second HA elution buffer. In some embodiments, a first HA eluate and a second HA eluate are collected from the first HA elution step and the second HA elution step, respectively, and wherein the first HA eluate and the second HA eluate comprise virus with different structure, purity or virus protein composition.

In some embodiments according to any one of the methods described herein, there is no intervening chromatography between the IE and the HA. In some embodiments, there is no intervening step between the IE and the HA.

In some embodiments according to any one of the methods described herein, the IE chromatography is anion exchange chromatography. In some embodiments, the anion exchange chromatography is Capto-DEAE chromatography. In some embodiments, the method comprises an IE pre-equilibrating step, and wherein the IE pre-equilibrating buffer has pH of about 7.0 to about 9.5. In some embodiments, the IE pre-equilibrating buffer is a phosphate buffer. In some embodiments, the method comprises an IE equilibrating step, and wherein the IE equilibrating buffer has pH of about 7.0 to about 9.5. In some embodiments, the IE equilibrating buffer is a phosphate buffer. In some embodiments, the method comprises an IE pre-elution step, and wherein the IE pre-elution buffer has pH of about 7.0 to about 9.5. In some embodiments, the IE pre-elution buffer is a phosphate buffer. In some embodiments, the IE pre-elution buffer further comprises sodium chloride. In some embodiments, the method comprises an IE elution step, and wherein the IE elution buffer has pH of about 7.0 to about 9.5. In some embodiments, the IE elution buffer is a phosphate buffer. In some embodiments, the IE elution buffer further comprises sodium chloride. In some embodiments, the hydroxyapatite chromatography is CHT chromatography. In some embodiments, the method comprises an HA pre-equilibrating step, and wherein the HA pre-equilibrating buffer has pH of about 7.0 to about 9.5. In some embodiments, the HA pre-equilibrating buffer is a phosphate buffer. In some embodiments, the method comprises an HA equilibrating step, and wherein the HA equilibrating buffer has pH of about 7.0 to about 9.5. In some embodiments, the HA equilibrating buffer is a phosphate buffer. In some embodiments, the method comprises an HA pre-elution step, and wherein the HA pre-elution buffer has pH of about 7.0 to about 9.5. In some embodiments, the HA pre-elution buffer is a phosphate buffer. In some embodiments, the method comprises an HA elution step, and wherein the HA elution buffer has pH of about 7.0 to about 9.5. In some embodiments, the HA elution buffer is a phosphate buffer.

In some embodiments according to any one of the methods described herein, the method further comprises a virus inactivation step. In some embodiments, the virus inactivation step is carried out prior to the IE chromatography, the HA chromatography, or both. In some embodiments, the virus inactivation step is carried out after the IE chromatography, the HA chromatography, or both. In some embodiments, the inactivation step comprises inactivating the virus with an inactivating agent.

In some embodiments according to any one of the methods described herein, the biological sample is subjected to a clarification step prior to being loaded to the IE or HA column. In some embodiments, the clarification step comprise microfiltration through a microfilter having pore size of 0.1-0.5 μm.

In some embodiments according to any one of the methods described herein, the biological sample is not subjected to centrifugation or ultrafiltration prior to being loaded to the IE or HA column.

In some embodiments according to any one of the methods described herein, the biological sample is a virus harvest sample. In some embodiments, the virus harvest sample is derived from a culture of animal tissue, avian tissue, primary animal cells, or passaged cells.

In some embodiments according to any one of the methods described herein, the enveloped virus is selected from the group consisting of rabies virus, influenza virus, Japanese encephalitis virus, measles virus, rubella virus, varicella virus, mumps virus, dengue fever virus, or human immunodeficiency virus (HIV). In some embodiments, the virus is rabies virus.

In some embodiments according to any one of the methods described herein, the method further comprises obtaining the biological sample. In some embodiments, the biological sample is obtained by harvesting a virus with animal tissue, avian tissue, primary animal cells, or passaged cells.

In some embodiments according to any one of the methods described herein, the method further comprises combining the isolated virus with a stabilizer. In some embodiments, the stabilizer comprises sucrose and albumin. In some embodiments, the albumin is human serum albumin. In some embodiments, the weight ratio of sucrose in the mixture is about 0.5-10%. In some embodiments, the weight ratio of albumin in the mixture is about 1-20%.

The present application further provides compositions comprising the isolated enveloped virus obtained according to any one of methods described herein. In some embodiments, the composition is a virus vaccine.

The present application further provides virus compositions comprising rabies virus particles, wherein at least about 80% of the total protein in the composition is viral protein, wherein the viral protein comprises: at least about 35-48% protein G. In some embodiments, the virus protein further comprises: about 28-37% protein N; about 8-12% protein P; and about 13-16% protein M. In some embodiments, at least about 80% of the rabies virus particles in the composition are intact viral particles. In some embodiments, the intactness of the virus particles can be determined by size, shape, potency (e.g., NIH test), biophysical or biochemical characteristics (e.g., glycosylation of outer membrane protein). In some embodiments, the composition is substantially free of non-viral DNA. In some embodiments, the composition has a potency (e.g., NIH test) of at least about 4 IU/dose or 4 IU/25 μg. In some embodiments, the composition is stable for at least about 1, 2, 3, 4, 5, 6, 7, 8, or 9 months at room temperature or under a refrigerated condition. In some embodiments, the virus composition further comprises a stabilizer. In some embodiments, the stabilizer comprises sucrose and albumin. In some embodiments, pH of the composition is about 7.5-7.7. In some embodiments, the composition is white when it is solid, and wherein a solution of the composition is clear. In some embodiments, the water content of the composition is less than 3%. In some embodiments, the potency (e.g., NIH test) of the composition under long term stability test is at least about 4 IU/dose or 4 IU/25 μg. In some embodiments, the potency (e.g., NIH test) of the composition under heat stability test is at least 3 IU/dose. In some embodiments, the bovine serum albumin (BSA) content is less than about 10 ng/dose. In some embodiments, the composition is a virus vaccine composition. In some embodiments, the composition is lyophilized.

The present application further provides commercial batches of a virus vaccine composition described herein.

The present application further provides methods of assessing suitability of a virus vaccine composition comprising rabies virus particles for clinical use, comprising: a) determining the percentage of viral proteins out of the total protein in the composition and b) determining the relative percentage of each of G, N, P, M in the viral proteins, wherein the composition is suitable for clinical use if i) at least about 80% of the total protein in the composition is viral protein, and ii) the viral protein comprises: about 35-48% protein G. In some embodiments, the viral protein in the composition further comprises: about 28-37% protein N; about 8-12% protein P; and about 13-16% protein M.

The present application further provides methods of releasing a commercial batch of a virus vaccine composition comprising rabies virus particles for clinical use, comprising: a) determining the percentage of viral proteins out of the total protein in the composition; b) determining the relative percentage of each of G, N, P, M in the viral proteins, and c) releasing the commercial batch for clinical use if i) at least about 80% of the total protein in the composition is viral protein, and ii) the viral protein comprises about 35-48% protein G. In some embodiments, the viral protein in the composition further comprises: about 28-37% N; about 8-12% P; and about 13-16% M. In some embodiments, the percentage of the viral proteins out of the total proteins in the composition is determined by SDS-PAGE. In some embodiments, the relative percentage of each of G, N, P, M in the viral proteins is determined by HPLC.

Figure 1:
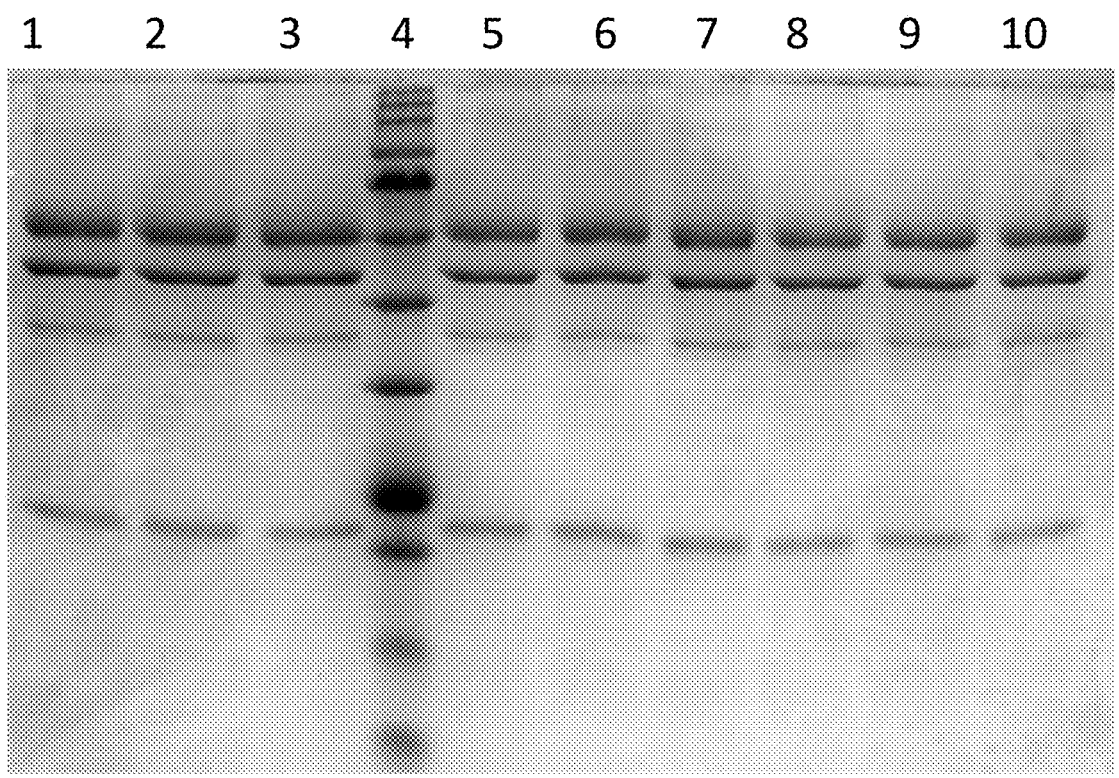
FIG. 1 shows the results of SDS-page electrophoresis of purified rabies virus harvested from different sources as described in Example 1. Bands No. 1-3 represent the purified virus harvested from the Vero cells in square flasks. Band No. 4 represents the protein marker; Band 5-7 represent the purified virus harvested from Vero cells in roller flasks; bands 8-10 represent the purified virus harvested from Vero cells in bioreactor.
Figure 2:
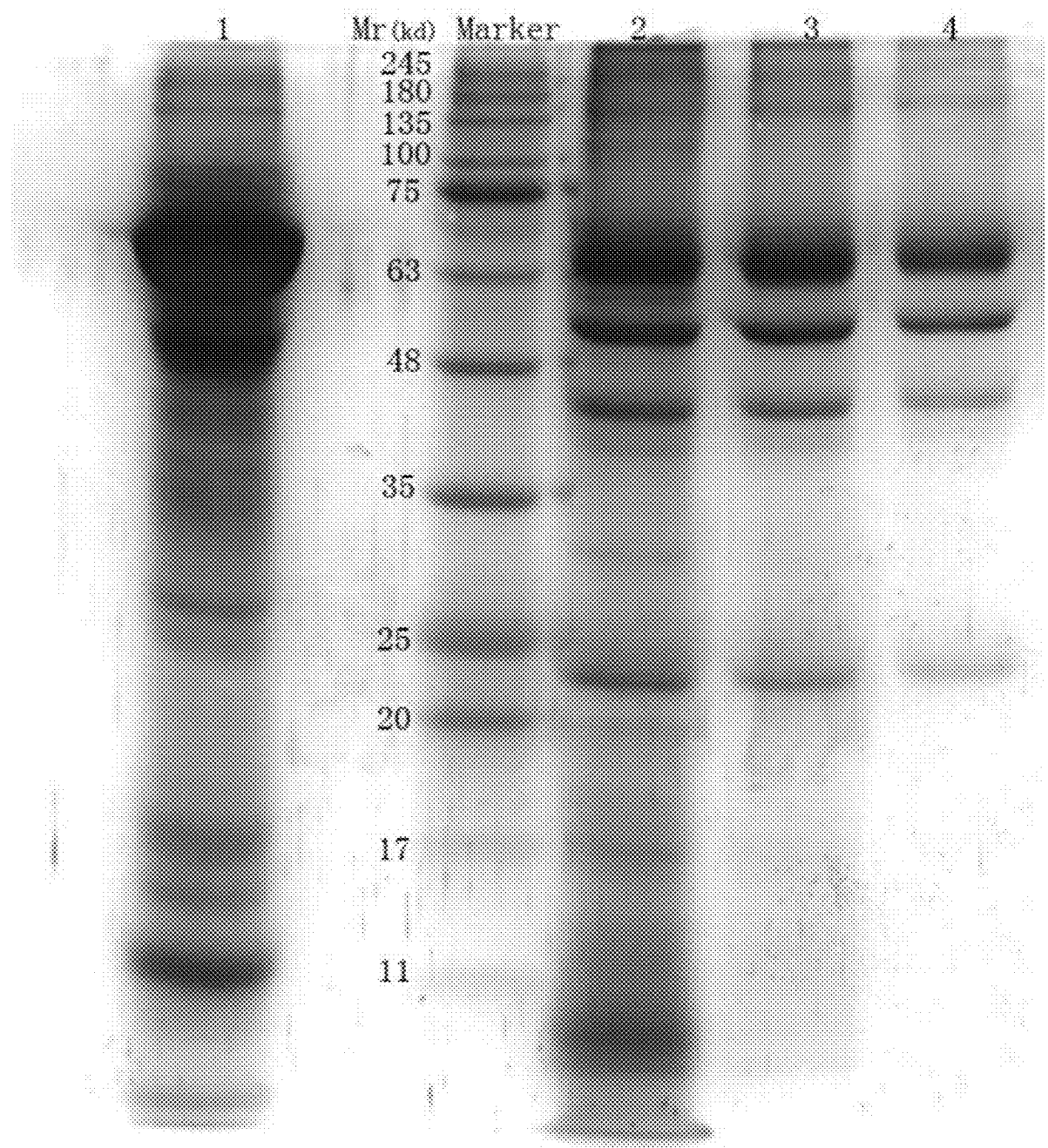
FIG. 2 shows the results of SDS-page electrophoresis of the rabies virus samples in different stages of the purification process as described in Example 1. Marker represents the reference sample that indicates molecular weight standard of proteins. "Mr" is the protein molecular weight of each band (in KD). Band No. 1 represents the virus harvest sample collected from harvest culture. Band No. 2 represents the collected eluate from the ion exchange chromatography. Band No. 3-4 represent the collected eluate from the hydroxyapatite chromatography. Band No. 3 represents the virus sample prior to the desalination. Band No. 4 represents the virus sample after the desalination.

In addition, the outer membrane protein(s) are very fragile and easily damaged or destroyed under the methods such as ultrafiltration. Therefore, purification processes that employ such methods can result in a higher degree of heterogeneity of virus particles (e.g., a higher percentage of incomplete and/or less preferable virus particles). Furthermore, existing purification conditions often need to be extensively changed when the harvest methods are changed. It is also difficult to ensure the production of stable purified virus when purifying different batches of virus particles harvested by the same harvest method.

One example of the enveloped virus is rabies virus. Rabies virus particles consist of a single-stranded RNA (which consists of about 11,930 nucleotides) and five proteins including proteins L, P, G, M and N. Together with single-stranded RNA, 20-150 protein L and 950 protein P form a structurally stable nucleocapsid. The nucleocapsid is encapsulated by the bilayer lipid membrane derived from the host cells. About 1650 protein M are located between the nucleocapsid and the lipid membrane. Different amounts (i.e., copy number) of protein G are located on the surface of the lipid membrane. Different amounts and lengths of oligosaccharides are linked to protein G. The copy number and the degree of glycosylation of the protein G have a critical impact on the biological and immunological properties of the virus particles.

Cultures that can be used to harvest rabies virus include mouse brain, chicken embryo, duck embryo, hamster kidney primary cells, chicken embryo fibroblast, human diploid cells and Vero cells. No matter which culture is used, rabies virus harvest culture is always a mixture of complex components including various structures and/or compositions of virus particles and various impurities.

The size of an intact rabies virus particle is about 75×180 nm. It has a molecular weight of about $5 \times 10^8$-$8 \times 10^8$, sedimentation coefficient of 600S, buoyant density in sucrose solution of 1.14-1.17 g/ml. The diameter of exfoliated cells is about 5 μm. Most of the cell debris has a diameter of more than 0.8 μm, which is significantly larger than those of rabies virus particles. Most of the host cell proteins, lipids, carbohydrates, and RNA (mainly tRNA and rRNA) have molecular weight below 1,000 KD, which are significantly smaller than rabies virus particles. Messenger RNA are larger but very unstable, therefore very few of them exist in the harvest culture. Host cell DNA thereof include DNA and fragments that are larger or smaller than rabies virus particles, or comparable in size as the rabies virus. Structural derivatives of rabies virus particles also include those larger (e.g., viral aggregation), smaller (e.g., viral subunit macromolecules due to viral lysis, fragmentation or failure of proper assembling) or comparable in size (e.g., virus particles with non-preferable copy number and/or non-preferable degree of glycosylation on the outer membrane protein as discussed above) compared to intact and/or preferable rabies virus.

Existing methods for purifying rabies virus particles and producing human rabies vaccine mainly use methods of molecular sieves (such as taking advantage of the differences in molecular weight and buoyant density). For example, early products used microfiltration to remove tissue debris, exfoliated cells or cell debris. Subsequently, in order to improve the potency of the rabies vaccine, ultrafiltration concentration technique was added to remove small molecular impurities. The purity of the rabies vaccine was further improved by the sucrose zone ultracentrifugation technique established in 1970s and the gel filtration chromatography established in 1990s. Since then, the purification process of the human rabies vaccine has no further major improvements. Similar purification methods are employed including: clarification of the virus harvest culture with microfiltration, followed by ultrafiltration concentration, sucrose zone ultracentrifugation and/or gel filtration column chromatography.

However, existing methods for purification of rabies virus particles are less satisfactory because of the following reasons. First, the produced vaccine has a low purity of virus particles. The amount of the harmful impurities in the vaccine product is high, which result in adverse reactions in the vaccine users. These harmful impurities include DNA and proteins derived from host cells, animal origin serum albumin (such as bovine serum albumin) and β-propiolactone-human albumin complex formed during virus inactivation.

Second, the vaccine contains a low dose of the active ingredient. Due to the high amount of the impurities, rapid and accurate physical and chemical analysis and/or methods cannot be carried out to detect and control the dosage of the active ingredient. Instead, potency (NIH test) and antigen concentration (ELISA test) are relied upon to assess the dosage of the active ingredient. However, the results of the two methods were less accurate, especially the former one. (Based upon data published by the WHO Expert Committee, the deviation of the NIH test ranges from 25% to 400%.) The ELISA test detects the total amount of virus particles without distinguishing the dosage of the active ingredient and the impurities such as structural derivations of the virus particles as discussed above. Therefore, the result of the ELISA test does not accurately reflect the biological potency of the vaccine. Because the dosage of the active ingredient cannot be accurately detected and controlled, a dose of the vaccine can have either less than enough or more than enough amount of active dosage, which can lead to a failure of immunogenicity or increased risk or incidence of adverse reactions.

Third, the vaccine formulation is complex and has a poor stability. Because of the low purity of the virus particles, a large amount of protective agents are added to maintain the stability of the vaccine product. Excessive protective agents not only increase user's metabolic burden, but also increase cost for production.

The present application provides methods of producing highly intact, homogenous and stable enveloped virus particles by subjecting the virus sample to ion exchange chromatography ("IE") and hydroxyapatite chromatography ("HA"). In some aspects, the present application provides methods to selectively purify virus particles with preferred properties and/or compositions of the outer membrane protein(s) on the surface of the enveloped virus. The properties and compositions of the outer membrane protein include the amino acid compositions, the charges (e.g., the net charges), the degree of phosphorylation, the degree of glycosylation, and the copy number of the outer membrane proteins. In some aspects, the methods comprise a less harsh clarification step and/or concentration step to preserve the intactness of the virus particles by microfiltration through a microfilter compared to ultracentrifugation and ultrafiltration. In some aspects, the methods comprise a step of combining the virus composition with a stabilizer that comprises sucrose and albumin, wherein the stabilizer does not comprise gelatin, dextran, trehalose, surfactants, and/or animal-proteins. In some aspects, the present application provides virus compositions (such as virus vaccines) comprising virus particles (such as rabies virus particles) that have a high purity and a preferred relative percentage of outer membrane protein(s).

Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

The term "about X-Y" used herein has the same meaning as "about X to about Y." The expression "about X, Y or Z" used herein has the same meaning as "about X, about Y, or about Z."

As used herein, reference to "not" a value or parameter generally means and describes "other than" a value or parameter. For example, the method is not used to treat cancer of type X means the method is used to treat cancer of types other than X.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

Method of Isolating Virus

In some embodiments, there is provides a method of purifying an enveloped virus from a biological sample, comprising subjecting the biological sample to an ion exchange ("IE") chromatography and a hydroxyapatite ("HA") chromatography. In some embodiments, the hydroxyapatite chromatography is carried out after the ion exchange chromatography. In some embodiments, the ion exchange chromatography is carried out after the hydroxyapatite chromatography. In some embodiments, there is no intervening chromatography between the IE and the HA. In some embodiments, the IE chromatography is anion exchange chromatography (e.g., Capto-DEAE chromatography). In some embodiments, the hydroxyapatite chromatography is CHT chromatography. In some embodiments, the virus is selected from the group consisting of rabies virus, Japanese encephalitis virus and influenza virus. In some embodiments, the IE elution buffer comprises a phosphate buffer. In some embodiments, the IE elution buffer has pH of 7.0-9.5. In some embodiments, the IE elution buffer comprises a salt (e.g., sodium chloride). In some embodiments, the HA elution buffer comprises a phosphate buffer and has pH of 7.0-9.5.

In some embodiments, there is provides a method of purifying an enveloped virus from a biological sample, comprising subjecting the biological sample to an ion exchange ("IE") chromatography and a hydroxyapatite ("HA") chromatography, wherein the IE chromatography comprises: a) an optional IE pre-equilibration step, comprising pre-equilibrating an ion exchange column with an ion exchange pre-equilibrating buffer; b) an IE loading step, comprising loading the biological sample or a post-HA chromatography sample to the ion exchange column; c) an optionally IE equilibration step, comprising equilibrating the ion exchange column with an IE equilibrating buffer; d) an optional IE pre-elution step, comprising pre-eluting the ion exchange column with an IE pre-eluting buffer; and e) an IE elution step, comprising eluting the IE column with an IE elution buffer. In some embodiments, the hydroxyapatite chromatography is carried out after the ion exchange chromatography. In some embodiments, the ion exchange chromatography is carried out after the hydroxyapatite chromatography. In some embodiments, there is no intervening chromatography between the IE and the HA. In some embodiments, the IE chromatography is anion exchange chromatography (e.g., Capto-DEAE chromatography). In some embodiments, the hydroxyapatite chromatography is CHT chromatography. In some embodiments, the virus is selected from the list comprising rabies virus, Japanese encephalitis virus and influenza virus. In some embodiments, the IE elution buffer comprises a phosphate buffer. In some embodiments, the IE elution buffer has pH of 7.0-9.5. In some embodiments, the IE elution buffer comprises a salt (e.g., sodium chloride). In some embodiments, the HA elution buffer comprises a phosphate buffer and has pH of 7.0-9.5.

In some embodiments, there is provides a method of purifying an enveloped virus from a biological sample, comprising subjecting the biological sample to an ion exchange ("IE") chromatography and a hydroxyapatite ("HA") chromatography, wherein the HA chromatography comprises: a) an optional HA pre-equilibration step, comprising pre-equilibrating an HA column with an HA pre-equilibrating buffer; b) an HA loading step, comprising loading the biological sample or a post-IE chromatography sample to the HA column; c) an optionally HA equilibration step, comprising equilibrating the HA column with an HA equilibrating buffer; d) an optional HA pre-elution step, comprising pre-eluting the HA column with an HA pre-eluting buffer; and e) an HA elution step, comprising eluting the HA column with an HA elution buffer. In some embodiments, the hydroxyapatite chromatography is carried out after the ion exchange chromatography. In some embodiments, the ion exchange chromatography is carried out after the hydroxyapatite chromatography. In some embodiments, there is no intervening chromatography between the IE and the HA. In some embodiments, the IE chromatography is anion exchange chromatography (e.g., Capto-DEAE chromatography). In some embodiments, the hydroxyapatite chromatography is CHT chromatography. In some embodiments, the virus is selected from the list comprising rabies virus, Japanese encephalitis virus and influenza virus. In some embodiments, the IE elution buffer comprises a phosphate buffer. In some embodiments, the IE elution buffer has pH of 7.0-9.5. In some embodiments, the IE elution buffer comprises a salt (e.g., sodium chloride). In some embodiments, the HA elution buffer comprises a phosphate buffer and has pH of 7.0-9.5.

In some embodiments, there is provides a method of purifying an enveloped virus from a biological sample, comprising subjecting the biological sample to an ion exchange ("IE") chromatography and a hydroxyapatite ("HA") chromatography, wherein the IE chromatography comprises: a) an optional IE pre-equilibration step, comprising pre-equilibrating an ion exchange column with an ion exchange pre-equilibrating buffer; b) an IE loading step, comprising loading the biological sample or a post-HA chromatography sample to the ion exchange column; c) an optionally IE equilibration step, comprising equilibrating the ion exchange column with an IE equilibrating buffer; d) an optional IE pre-elution step, comprising pre-eluting the ion exchange column with an IE pre-eluting buffer; and e) an IE elution step, comprising eluting the IE column with an IE elution buffer, and wherein the HA chromatography comprises: a) an optional HA pre-equilibration step, comprising pre-equilibrating an HA column with an HA pre-equilibrating buffer; b) an HA loading step, comprising loading the biological sample or a post-IE chromatography sample to the HA column; c) an optionally HA equilibration step, comprising equilibrating the HA column with an HA equilibrating buffer; d) an optional HA pre-elution step, comprising pre-eluting the HA column with an HA pre-eluting buffer; and e) an HA elution step, comprising eluting the HA column with an HA elution buffer. In some embodiments, the hydroxyapatite chromatography is carried out after the ion exchange chromatography. In some embodiments, the ion exchange chromatography is carried out after the hydroxyapatite chromatography. In some embodiments, there is no intervening chromatography between the IE and the HA. In some embodiments, the IE chromatography is anion exchange chromatography (e.g., Capto-DEAE chromatography). In some embodiments, the hydroxyapatite chromatography is CHT chromatography. In some embodiments, the virus is selected from the list comprising rabies virus, Japanese encephalitis virus and influenza virus. In some embodiments, the IE elution buffer comprises a phosphate buffer. In some embodiments, the IE elution buffer has pH of 7.0-9.5. In some embodiments, the IE elution buffer comprises a salt (e.g., sodium chloride). In some embodiments, the HA elution buffer comprises a phosphate buffer and has pH of 7.0-9.5.

In some embodiments, there is provided a method of purifying an enveloped virus from a biological sample, comprising 1) subjecting the biological sample to an ion exchange ("IE") chromatography and a hydroxyapatite ("HA") chromatography, and 2) a virus inactivation step, wherein the inactivation step can be carried out prior to, after, or in between of the HA chromatography and IE chromatography. In some embodiments, the virus inactivation step is carried out after the IE chromatography and the HA chromatography. In some embodiments, the inactivation step comprises inactivating the virus with an inactivating agent. In some embodiments, the hydroxyapatite chromatography is carried out after the ion exchange chromatography. In some embodiments, the ion exchange chromatography is carried out after the hydroxyapatite chromatography. In some embodiments, there is no intervening chromatography between the IE and the HA. In some embodiments, the IE chromatography is anion exchange chromatography (e.g., Capto-DEAE chromatography). In some embodiments, the hydroxyapatite chromatography is CHT chromatography. In some embodiments, the virus is selected from the list comprising rabies virus, Japanese encephalitis virus and influenza virus. In some embodiments, the IE elution buffer comprises a phosphate buffer. In some embodiments, the IE elution buffer has pH of 7.0-9.5. In some embodiments, the IE elution buffer comprises a salt (e.g., sodium chloride). In some embodiments, the HA elution buffer comprises a phosphate buffer and has pH of 7.0-9.5.

In some embodiments, there is provided a method of purifying an enveloped virus from a biological sample, comprising 1) a clarification step; and 2) subjecting the biological sample to an ion exchange ("IE") chromatography and a hydroxyapatite ("HA") chromatography, wherein the clarification step can be carried out prior to, after, or in between the HA chromatography and IE chromatography. In some embodiments, the biological sample is subjected to a clarification step prior to being loaded to the IE or HA column. In some embodiments, the clarification step comprises microfiltration through a microfilter having pore size of 0.1-0.5 µm. In some embodiments, the biological sample is not subjected to centrifugation or ultrafiltration prior to being loaded to the IE or HA column. In some embodiments, the hydroxyapatite chromatography is carried out after the ion exchange chromatography. In some embodiments, the ion exchange chromatography is carried out after the hydroxyapatite chromatography. In some embodiments, there is no intervening chromatography between the IE and the HA. In some embodiments, the IE chromatography is anion exchange chromatography (e.g., Capto-DEAE chromatography). In some embodiments, the hydroxyapatite chromatography is CHT chromatography. In some embodiments, the virus is selected from the list comprising rabies virus, Japanese encephalitis virus and influenza virus. In some embodiments, the IE elution buffer comprises a phosphate buffer. In some embodiments, the IE elution buffer has pH of 7.0-9.5. In some embodiments, the IE elution buffer comprises a salt (e.g., sodium chloride). In some embodiments, the HA elution buffer comprises a phosphate buffer and has pH of 7.0-9.5.

In some embodiments, there is provided a method of purifying an enveloped virus from a biological sample, comprising 1) a clarification step; 2) an inactivation step; and 3) subjecting the biological sample to an ion exchange ("IE") chromatography and a hydroxyapatite ("HA") chromatography, wherein the clarification step, the inactivation step, the IE chromatography and the HA chromatography can be carried out in any order. In some embodiments, the clarification step comprises microfiltration through a microfilter having pore size of 0.1-0.5 µm. In some embodiments, the biological sample is not subjected to centrifugation or ultrafiltration prior to being loaded to the IE or HA column. In some embodiments, the hydroxyapatite chromatography is carried out after the ion exchange chromatography. In some embodiments, the ion exchange chromatography is carried out after the hydroxyapatite chromatography. In some embodiments, there is no intervening chromatography between the IE and the HA. In some embodiments, the IE chromatography is anion exchange chromatography (e.g., Capto-DEAE chromatography). In some embodiments, the hydroxyapatite chromatography is CHT chromatography. In some embodiments, the virus is selected from the list comprising rabies virus, Japanese encephalitis virus and influenza virus. In some embodiments, the IE elution buffer comprises a phosphate buffer. In some embodiments, the IE elution buffer has pH of 7.0-9.5. In some embodiments, the IE elution buffer comprises a salt (e.g., sodium chloride). In some embodiments, the HA elution buffer comprises a phosphate buffer and has pH of 7.0-9.5.

In some embodiments, there is provided a method of purifying an enveloped virus from a biological sample, comprising 1) obtaining the biological sample by proliferating the virus in a culture, and 2) subjecting the biological sample to an ion exchange ("IE") chromatography and a hydroxyapatite ("HA") chromatography. In some embodiments, the biological sample is derived from a culture of animal tissue, avian tissue, primary animal cells, or passaged cells. In some embodiments, the hydroxyapatite chromatography is carried out after the ion exchange chromatography. In some embodiments, the ion exchange chromatography is carried out after the hydroxyapatite chromatography. In some embodiments, there is no intervening chromatography between the IE and the HA. In some embodiments, the IE chromatography is anion exchange chromatography (e.g., Capto-DEAE chromatography). In some embodiments, the hydroxyapatite chromatography is CHT chromatography. In some embodiments, the virus is selected from the list comprising rabies virus, Japanese encephalitis virus and influenza virus. In some embodiments, the IE elution buffer comprises a phosphate buffer. In some embodiments, the IE elution buffer has pH of 7.0-9.5. In some embodiments, the IE elution buffer comprises a salt (e.g., sodium chloride). In some embodiments, the HA elution buffer comprises a phosphate buffer and has pH of 7.0-9.5.

In some embodiments, there is provided a method of purifying an enveloped virus from a biological sample, comprising 1) obtaining the biological sample by proliferating the virus in a culture; 2) subjecting the biological sample to a clarification step; and 3) subjecting the biological sample to an ion exchange ("IE") chromatography and a hydroxyapatite ("HA") chromatography, wherein the clarification step can be carried out prior to, in between, or after the HA chromatography and IE chromatography. In some embodiments, the biological sample is subjected to a clarification step prior to being loaded to the IE or HA column. In some embodiments, the hydroxyapatite chromatography is carried out after the ion exchange chromatography. In some embodiments, the ion exchange chromatography is carried out after the hydroxyapatite chromatography. In some embodiments, there is no intervening chromatography between the IE and the HA. In some embodiments, the IE chromatography is anion exchange chromatography (e.g., Capto-DEAE chromatography). In some embodiments, the hydroxyapatite chromatography is CHT chromatography. In some embodiments, the virus is selected from the list comprising rabies virus, Japanese encephalitis virus and influenza virus. In some embodiments, the IE elution buffer comprises a phosphate buffer. In some embodiments, the IE elution buffer has pH of 7.0-9.5. In some embodiments, the IE elution buffer comprises a salt (e.g., sodium chloride). In some embodiments, the HA elution buffer comprises a phosphate buffer and has pH of 7.0-9.5.

In some embodiments, there is provided a method of purifying an enveloped virus from a biological sample, comprising 1) obtaining the biological sample by proliferating the virus in a culture; 2) subjecting the biological sample to a clarification step; and 3) subjecting the biological sample to an ion exchange ("IE") chromatography and a hydroxyapatite ("HA") chromatography, 4) an virus inactivation step. In some embodiments, the virus inactivation step is carried out after the IE chromatography and the HA chromatography. In some embodiments, the clarification step is carried out before the IE chromatography and the HA chromatography. In some embodiments, the hydroxyapatite chromatography is carried out after the ion exchange chromatography. In some embodiments, the ion exchange chromatography is carried out after the hydroxyapatite chromatography. In some embodiments, there is no intervening chromatography between the IE and the HA. In some embodiments, the IE chromatography is anion exchange chromatography (e.g., Capto-DEAE chromatography). In some embodiments, the hydroxyapatite chromatography is CHT chromatography. In some embodiments, the virus is selected from the list comprising rabies virus, Japanese encephalitis virus and influenza virus. In some embodiments, the IE elution buffer comprises a phosphate buffer. In some embodiments, the IE elution buffer has pH of 7.0-9.5. In some embodiments, the IE elution buffer comprises a salt (e.g., sodium chloride). In some embodiments, the HA elution buffer comprises a phosphate buffer and has pH of 7.0-9.5.

In some embodiments, there is provides a method of purifying an enveloped virus from a biological sample, comprising 1) subjecting the biological sample to an ion exchange ("IE") chromatography and a hydroxyapatite ("HA") chromatography, and 2) combining the isolated virus with a stabilizer. In some embodiments, the stabilizer comprises sucrose and albumin. In some embodiments, the albumin is human serum albumin. In some embodiments, the weight ratio of sucrose in the mixture is about 0.5-10%. In some embodiments, the weight ratio of albumin in the mixture is about 1-20%. In some embodiments, the hydroxyapatite chromatography is carried out after the ion exchange chromatography. In some embodiments, the ion exchange chromatography is carried out after the hydroxyapatite chromatography. In some embodiments, there is no intervening chromatography between the IE and the HA. In some embodiments, the IE chromatography is anion exchange chromatography (e.g., Capto-DEAE chromatography). In some embodiments, the hydroxyapatite chromatography is CHT chromatography. In some embodiments, the virus is selected from the list comprising rabies virus, Japanese encephalitis virus and influenza virus. In some embodiments, the IE elution buffer comprises a phosphate buffer. In some embodiments, the IE elution buffer has pH of 7.0-9.5. In some embodiments, the IE elution buffer comprises a salt (e.g., sodium chloride). In some embodiments, the HA elution buffer comprises a phosphate buffer and has pH of 7.0-9.5.

A. Ion Exchange (IE) Chromatography

The methods described herein comprises an IE chromatography step comprising 1) an IE loading step comprising loading the biological sample or a post-HA chromatography sample to the ion exchange column; and 2) an IE elution step, comprising eluting the IE column with an IE elution buffer. In some embodiments, the methods further comprise an IE equilibration step, comprising equilibrating the ion exchange column with an IE equilibrating buffer; an IE pre-equilibration step, comprising pre-equilibrating an ion exchange column with an ion exchange pre-equilibrating buffer; and/or an IE pre-elution step, comprising pre-eluting the ion exchange column with an IE pre-eluting buffer.

In some embodiments, the methods comprise a) an IE loading step, comprising loading the biological sample or a post-HA chromatography sample to the ion exchange column; b) an IE equilibration step, comprising equilibrating the ion exchange column with an IE equilibrating buffer; c)

an IE elution step, comprising eluting the IE column with an IE elution buffer. In some embodiments, the methods comprise a) an IE pre-equilibration step, comprising pre-equilibrating an ion exchange column with an ion exchange pre-equilibrating buffer; b) an IE loading step, comprising loading the biological sample or a post-HA chromatography sample to the ion exchange column; c) an IE equilibration step, comprising equilibrating the ion exchange column with an IE equilibrating buffer; d) an IE elution step, comprising eluting the IE column with an IE elution buffer. In some embodiments, the methods comprise a) an IE pre-equilibration step, comprising pre-equilibrating an ion exchange column with an ion exchange pre-equilibrating buffer; b) an IE loading step, comprising loading the biological sample or a post-HA chromatography sample to the ion exchange column; c) an IE elution step, comprising eluting the IE column with an IE elution buffer. In some embodiments, the methods comprise a) an IE loading step, comprising loading the biological sample or a post-HA chromatography sample to the ion exchange column; b) an IE pre-elution step, comprising pre-eluting the ion exchange column with an IE pre-eluting buffer; and c) an IE elution step, comprising eluting the IE column with an IE elution buffer. In some embodiments, the methods comprise a) an IE loading step, comprising loading the biological sample or a post-HA chromatography sample to the ion exchange column; b) an IE equilibration step, comprising equilibrating the ion exchange column with an IE equilibrating buffer; c) an IE pre-elution step, comprising pre-eluting the IE column with an IE pre-elution buffer; and d) an IE elution step, comprising eluting the IE column with an IE elution buffer.

In some embodiments, the methods comprise a) an IE pre-equilibration step, comprising pre-equilibrating an ion exchange column with an ion exchange pre-equilibrating buffer; b) an IE loading step, comprising loading the biological sample or a post-HA chromatography sample to the ion exchange column; c) an IE equilibration step, comprising equilibrating the ion exchange column with an IE equilibrating buffer; d) an IE pre-elution step, comprising pre-eluting the IE column with an IE pre-elution buffer; and e) an IE elution step, comprising eluting the IE column with an IE elution buffer.

In some embodiments, the IE chromatography comprises an anion exchange (AE) chromatography. In some embodiments, the IE chromatography comprises a cation exchange chromatography.

The conditions of the IE chromatography can be determined according to charge properties of the one or more outer membrane proteins(s) on the surface of the enveloped virus. In some embodiments, one or more outer membrane proteins(s) on the surface of the enveloped virus have positive charge(s), and a cation exchange chromatography is carried out to purify the enveloped virus. In some embodiments, one or more outer membrane proteins(s) on the surface of the enveloped virus have negative charge(s), and an anion exchange chromatography is carried out to purify the enveloped virus. In some embodiments, the charge properties of the one or more outer membrane proteins are characterized by the net charge of one or more outer membrane proteins. In some embodiments, the charge properties of the one or more outer membrane proteins are characterized by the net charge of all the outer membrane proteins. In some embodiments, the enveloped virus is rabies virus, and the charge properties of the one or more membrane proteins on the surface of the enveloped virus are characterized by the net charge of the outer membrane protein G.

In some embodiments, the conditions of IE chromatography are determined according to the copy number of the one or more outer membrane proteins (e.g. copy number of a specific outer membrane protein, a portion of the one or more outer membrane proteins, and/or all of the outer membrane proteins on the surface of the virus), and/or the degree of glycosylation of the one or more outer membrane proteins (e.g. the degree of glycosylation of a specific outer membrane protein, a portion of the one or more outer membrane proteins, and/or all of the outer membrane proteins on the surface of the virus). In some embodiments, the conditions of IE chromatography can be any one or more of the following: the type of the column (e.g., anion or cation), the specific column to use, the conditions (e.g., the ion concentration, pH, whether the specific buffer comprises a salt, the type of salt, salt concentration and/or the volume to apply) of the pre-equilibrating buffer, equilibrating buffer, pre-elution buffer, and/or elution buffer, and/or the volume of the virus sample or amount of the virus to load.

In some embodiments, the ion concentration in an elution buffer is proportional to the copy number of the one or more outer membrane proteins. In some embodiments, the ion concentration in an elution buffer is inversely proportional to the degree of glycosylation of the one or more outer membrane proteins. In some embodiments, the enveloped virus has only one outer membrane protein. In some embodiments, the ion concentration in an elution buffer is proportional to the copy number of the only one outer membrane protein and inversely proportional to the degree of glycosylation of the only one outer membrane protein. In some embodiments, the only one outer membrane protein has a preferred range of copy number and/or a preferred range of degree of glycosylation. For example, the preferred ranger of copy number and/or a preferred range of degree of glycosylation of the only one outer membrane protein results in superior immunogenicity in an individual. In some embodiments, the ion concentration in an elution buffer is proportional to the preferred range of copy number of the only one outer membrane protein and/or inversely proportional to the preferred range of glycosylation degree of the only one outer membrane protein.

In some embodiments, the one or more outer membrane proteins have two copy numbers, or two ranges of copy number (i.e., the first range of copy number and the second range of copy number) and/or two degrees of glycosylation or two ranges of degrees of glycosylation (i.e., the first range of glycosylation degree and the second range of glycosylation degree.) In some embodiments, the IE chromatography comprises a first elution step and a second elution step, wherein first elution step is to elute the first batch of virus comprising the first range of copy number and/or the first range of degree of glycosylation, and wherein the second elution step is to elute the second batch of virus comprising the second range of copy number and/or the second range of degree of glycosylation. In some embodiments, the ion concentration in the first elution buffer is proportional to the first range of copy number of the one or more outer membrane proteins and inversely proportional to the first range of the degree of glycosylation of the one or more outer membrane proteins. In some embodiments, the ion concentration in the second elution buffer is proportional to the second range of copy number of the one or more outer membrane proteins and inversely proportional to the second range of the degree of glycosylation of the one or more outer membrane proteins.

Different copy numbers or preferred copy numbers (or preferred range of copy number) of the one or more outer membrane proteins can be represented by or converted to a particular (e.g., preferred) or a particular range (e.g., preferred range) of the relative percentage of the outer membrane protein in the total viral protein. The particular (e.g., preferred) or the particular range (e.g., preferred range) of the relative percentage of the outer membrane protein in the total viral protein (e.g., "the preferred ratio of outer membrane protein") can be any relative percentage or any range of relative percentages of the one or more outer membrane proteins. Similarly, a particular degree of glycosylation (e.g., a preferred degree of glycosylation, a preferred range of degree of glycosylation) can be any degree or range of degree of glycosylation on the one or more outer membrane proteins. The particular/preferred ratio of the outer membrane protein and the particular/preferred degree of glycosylation can be determined according to the purpose of the viral particles. Exemplary purposes of using the virus particles include for vaccine preparation and for research. In some embodiments, the virus that has the particular/preferred ratio of the outer membrane protein has higher potency (e.g., NIH test) than the same kind of virus that does not have the particular/preferred ratio of the outer membrane protein. In some embodiments, a vaccine with the virus that has the particular/preferred ratio of the outer membrane protein result in higher immunogenicity than a vaccine with the same kind of virus that do not have the particular/preferred ratio of the outer membrane protein. In some embodiments, the virus that has the particular/preferred degree of glycosylation on the outer membrane protein has higher potency (e.g., NIH test) than the same kind of virus that does not have the particular/preferred degree of glycosylation on the outer membrane protein. In some embodiments, a vaccine with the virus that has the particular/preferred degree of glycosylation on the outer membrane protein result in higher immunogenicity than a vaccine with the same kind of virus that do not have the particular/preferred degree of glycosylation on the outer membrane protein.

1) IE Column

In some embodiments, the IE column is an anion exchange (AE) chromatography. Exemplary anion exchange chromatography comprise positively charged ligand attached to a solid phase, such as quaternary amino groups, including for example a quaternary amine, such as quaternary alkylamine and quaternary alkylalkanol amine, or amine, diethylamine, diethylaminoethyl (DEAE) diethylaminopropyl, amino, timethylammoniumethyl, trimethylbenzyl ammonium, dimethylethanolbenzyl ammonium, and polyamine. Exemplary anion exchange chromatography include anion exchange materials such as DEAE cellulose, Poros PI 20, PI 50, HQ 10, HQ 20, HQ 50, D 50 from Applied Biosystems, MonoQ, MiniQ, Source 15Q and 30Q, Q, DEAE and ANX Sepharose Fast Flow, Q Sepharose High Performance, QAE SEPHADEX™ and FAST Q SEPHAROSE™ from GE Healthcare, WP PEI, WP DEAM, WP QUAT from J.T. Baker, Hydrocell DEAE and Hydrocell QA from Biochrom Labs Inc., UNOsphere Q, Macro-Prep DEAE and Macro-Prep High Q from BioRad, Ceramic HyperD Q, Ceramic HyperD DEAE, Q HyperZ, Trisacryl M and LS DEAE, Spherodex LS DEAE, QMA Spherosil LS, QMA Spherosil M from Pall Technologies, DOWEX Fine Mesh Strong Base Type I and Type π Anion Resins and DOWEX MONOSPHERE 77, weak base anion from Dow Liquid Separations, Matrex Cellufme A200, A500, Q500, and Q800, from Millipore, Fractogel® EMD TMAE, Fractogel® EMD DEAE, and Fractogel® EMD DMAE from EMD, Amberlite weak and strong anion exchangers type I and II, DOWEX weak and strong anion exchangers type I and II, Diaion weak and strong anion exchangers type I and II, Duolite from Sigma-Aldrich, TSK gel Q and DEAE 5PW and 5PW-HR, Toyopearl® SuperQ-650S, 650M and 650C3 QAE-550C and 650S, DEAE-650M and 650C from Tosoh, and QA52, DE23, DE32, DE51, DE52, DE53, Express-Ion D and Express-Ion Q from Whatman. Commercially available high-capacity resins include GigaCap Q-650M (Tosoh), Capto Q (GE Healthcare), Eshmuno™ Q from EMD, and Nuvia™ Q from Bio-rad. In some embodiments, the AE chromatography comprises a DEAE chromatography. In some embodiments, the DEAE chromatography is selected from the group consisting of DEAE-Sepharose®, Capto®-DEAE, and DEAE Cellulose chromatography. In some embodiments, the DEAE chromatography is Capto™-DEAE chromatography. In some embodiments, the AE chromatography comprises a quaternary ammonium (Q) chromatography. In some embodiments, the Q chromatography is selected from the group consisting of Q Sepharose®, Capto™-Q, Dowex®1×2, Amberlite/Amberjet®, and QAE Sephadex®.

In some embodiments, the IE column is a cation exchange chromatography. Exemplary cation exchange chromatography comprise negatively charged groups attached to a solid phase such as a sulfonate based group (e.g., MonoS, MiniS, Source 15S and 30S, SP Sepharose Fast Flow™, SP Sepharose High Performance from GE Healthcare, Toyopearl® SP-650S and SP-650M from Tosoh, Macro-Prep High S from BioRad, Ceramic HyperD S, Trisacryl M and LS SP and Spherodex LS SP from Pall Technologies); a sulfoethyl based group (e.g., Fractogel EMD SE from EMD, Poros S-10 and S-20 from Applied Biosystems); a sulphopropyl based group (e.g., TSK Gel SP 5PW and SP-5P W-HR from Tosoh, Poros HS-20 and HS 50 from Applied Biosystems); a sulfoisobutyl based group (e.g., Fractogel® EMD S03 from EMD); a sulfoxyethyl based group (e.g., SE52, SE53 and Express-Ion S from Whatman), a carboxymethyl based group (e.g., CM Sepharose Fast Flow from GE Healthcare, Hydrocell CM from Biochrom Labs Inc., Macro-Prep CM from BioRad, Ceramic HyperD CM, Trisacryl M CM, Trisacryl LS CM, from Pall Technologies, Matrex Cellufme C500 and C200 from Millipore, CM52, CM32, CM23 and Express—Ion C from Whatman, Toyopearl® CM-650S, CM-650M and CM-650C from Tosoh); sulfonic and carboxylic acid based groups (e.g. BAKERBOND Carboxy-Sulfon from J.T. Baker); a carboxylic acid based group (e.g., WP CBX from J.T Baker, DOWEX MAC-3 from Dow Liquid Separations, Amberlite Weak Cation Exchangers, DOWEX Weak Cation Exchanger, and Diaion Weak Cation Exchangers from Sigma-Aldrich and Fractogel EMD COO— from EMD); a sulfonic acid based group (e. g., Hydrocell SP from Biochrom Labs Inc., DOWEX Fine Mesh Strong Acid Cation Resin from Dow Liquid Separations, UNOsphere S from BioRad, WP Sulfonic from J.T. Baker, Amberlite Strong Cation Exchangers, DOWEX Strong Cation and Diaion Strong Cation Exchanger from Sigma-Aldrich); and a orthophosphate based group (e.g., PI 1 from Whatman). Commercially available high-capacity resins include GigaCap S-650M (Tosoh), Eshmuno™ S (EMD), Nuvia™ S (BioRad), Poros® XS (Applied Biosystems), and Capto S (GE Healthcare). In some embodiments, a cation exchange membrane can be used, e.g., Sartobind S (Sartorius; Edgewood, NY), Natrix Adsept™ S (also referred to as "Natrix S") and Natri Adsept™ C (also referred to as "Natrix C", and Mustang S (Pall). In some embodiments, the cation exchange chromatography comprises a carboxymethyl chromatography. In some embodiments, the cation exchange chromatography comprises a sulphomethy chromatography. In some embodiments, the cation exchange chromatography comprises a sulphoprophyl chromatography.

2) IE Pre-Equilibration Step

In some embodiments, the IE chromatography comprises an IE pre-equilibration step comprising pre-equilibrating an ion exchange column with an IE pre-equilibrating buffer.

In some embodiments, the IE pre-equilibrating buffer is an anionic buffer. In some embodiments, the anionic buffer is selected from the group consisting of phosphate buffer, Tris-HCl buffer, Tricine buffer, Hepes buffer, glycine buffer, TEA buffer, and Barbitone sodium buffer. In some embodiments, the pre-equilibrating buffer is a phosphate buffer.

In some embodiments, the IE pre-equilibrating buffer has pH of about 6.0-10.0, 6.5-9.5, 7.0-9.5, 7.0-9.0, 7.0-8.5, 7.0-8.0, 7.2-7.8, 7.4-7.7, 7.5-7.6 or 7.6.

In some embodiments, the IE pre-equilibrating buffer (e.g., anionic buffer, e.g., phosphate buffer) has a ion concentration (e.g., anion concentration in an anionic buffer, e.g., phosphate ion concentration) of about 1-80 mM, 1-50 mM, 3-40 mM, 5-30 mM, 10-30 mM, 15-25 mM, 18-22 mM, or 20 mM.

In some embodiments, the IE pre-equilibrating buffer (e.g., a phosphate buffer) further comprises a salt. In some embodiments, the salt is a sodium salt. In some embodiments, the salt is sodium chloride. In some embodiments, the concentration of the salt (e.g., sodium chloride) in the IE pre-equilibrating buffer (e.g., a phosphate buffer) is about 50 mM to about 220 mM. In some embodiments, the concentration of the salt (e.g., sodium chloride) in the IE pre-equilibrating buffer (e.g., a phosphate buffer) is about 1-500 mM, 10-400 mM, 50-300 mM, 100-200 mM, 125-175 mM, or 150 mM. In some embodiments, the IE pre-equilibrating buffer (e.g., a phosphate buffer) does not comprise a salt (e.g., a sodium salt, sodium chloride).

In some embodiments, about 1-20, 1-10, 1-8, 2-8, 2-6, or 2-5 column volumes of pre-equilibrating buffer is applied to the column.

In some embodiments, the IE pre-equilibrating buffer is a phosphate buffer that has pH of about 7.0-9.5. In some embodiments, the IE pre-equilibrating buffer is a phosphate buffer that has a phosphate ion concentration of about 10-30 mM, or 20 mM. In some embodiments, the IE pre-equilibrating buffer is a phosphate buffer that has pH of about 7.0-9.5 and a phosphate ion concentration of about 10-30 mM, or 20 mM. In some embodiments, the phosphate buffer further comprises sodium chloride of about 100-200 mM (e.g., 150 mM).

In some embodiments, the IE pre-equilibrating step is carried out at about 4-30° C., 10-25° C. or room temperature. In some embodiments, the IE pre-equilibrating step is carried out at about 2-8° C.

3) IE Loading Step

A virus sample (e.g., a supernatant containing virus harvested from a culture, e.g., an eluate collected from a HA chromatography) is loaded to the column in the IE chromatography. In some embodiments, the column is pre-equilibrated prior to the loading of the virus sample. In some embodiments, the column is not pre-equilibrated prior to the loading of the virus sample. In some embodiments, the virus sample is pretreated prior to the loading. In some embodiments, the virus sample is clarified prior to the loading. In some embodiments, the virus sample is clarified through microfiltration before being loaded to the column. In some embodiments, the microfiltration comprises filtrating the virus sample through a membrane with a pore size of about 0.1-1 μm or 1-1.5 μm.

In some embodiments, about 1-50, 1-40, 1-30, 1-20 or 5-20 column volumes of the virus sample are loaded to the IE column.

In some embodiments, the IE loading step is carried out at about 4-30° C., 10-25° C. or room temperature. In some embodiments, the IE pre-equilibrating step is carried out at about 2-8° C.

4) IE Equilibrating Step

In some embodiments, the IE chromatography comprises an IE equilibration step comprising equilibrating an ion exchange column with an IE equilibrating buffer.

In some embodiments, the IE equilibrating buffer is an anionic buffer. In some embodiments, the anionic buffer is selected from the group consisting of phosphate buffer, Tris-HCl buffer, Tricine buffer, Hepes buffer, glycine buffer, TEA buffer, and Barbitone sodium buffer. In some embodiments, the equilibrating buffer is a phosphate buffer.

In some embodiments, the IE equilibrating buffer is the same as the IE pre-equilibrating buffer.

In some embodiments, the IE equilibrating buffer (e.g., a phosphate buffer) has pH of about 6.0-10.0, 6.5-9.5, 7.0-9.5, 7.0-9.0, 7.0-8.5, 7.0-8.0, 7.2-7.8, 7.4-7.7, 7.5-7.6 or 7.6.

In some embodiments, the IE equilibrating buffer (e.g., phosphate buffer) has a ion concentration (e.g., phosphate ion concentration) of about 1-50 mM, or 1-40 mM, 5-30 mM, 10-30 mM, 15-25 mM, 18-22 mM, or 20 mM.

In some embodiments, the IE equilibrating buffer (e.g., a phosphate buffer) further comprises a salt. In some embodiments, the salt is a sodium salt. In some embodiments, the salt is sodium chloride. In some embodiments, the concentration of the salt (e.g., sodium chloride) in the IE equilibrating buffer (e.g., a phosphate buffer) is about 50 mM to about 220 mM. In some embodiments, the concentration of the salt (e.g., sodium chloride) in the IE equilibrating buffer (e.g., a phosphate buffer) is about 1-500 mM, 10-400 mM, 50-300 mM, 100-200 mM, 125-175 mM, or 150 mM. In some embodiments, the IE equilibrating buffer (e.g., a phosphate buffer) does not comprise a salt (e.g., a sodium salt, sodium chloride).

In some embodiments, about 1-20, 1-10, 1-8, 2-8, 2-6, or 2-5 column volumes of equilibrating buffer is applied to the column.

In some embodiments, the IE equilibrating buffer is a phosphate buffer that has pH of about 7.0-9.5. In some embodiments, the IE equilibrating buffer is a phosphate buffer that has a phosphate ion concentration of about 10-30 mM, or 20 mM. In some embodiments, the IE equilibrating buffer is a phosphate buffer that has pH of about 7.0-9.5 and a phosphate ion concentration of about 10-30 mM, or 20 mM. In some embodiments, the phosphate buffer further comprises sodium chloride of about 100-200 mM (e.g., 150 mM).

In some embodiments, the IE-equilibrating step is carried out at about 4-30° C., 10-25° C. or room temperature.

5) IE Pre-Elution Step

In some embodiments, the IE chromatography comprises an IE pre-elution step comprising pre-eluting an ion exchange column with an IE pre-elution buffer.

In some embodiments, the IE pre-elution buffer is an anionic buffer. In some embodiments, the anionic buffer is selected from the group consisting of phosphate buffer, Tris-HCl buffer, Tricine buffer, Hepes buffer, glycine buffer, TEA buffer, and Barbitone sodium buffer. In some embodiments, the IE pre-elution buffer is a phosphate buffer.

In some embodiments, the IE pre-elution buffer and the IE pre-equilibrating buffer/IE equilibrating buffer comprise a same kind of buffer (e.g. phosphate buffer).

In some embodiments, the pre-elution buffer (e.g., a phosphate buffer) has pH of about 6.0-10.0, 6.5-9.5, 7.0-9.5, 7.0-9.0, 7.0-8.5, 7.0-8.0, 7.2-7.8, 7.4-7.7, 7.5-7.6 or 7.6. In some embodiments, the difference of pH of the IE pre-elution buffer and the IE pre-equilibrating buffer/IE equilibrating buffer is less than about 2, 1, 1.5, 1, 0.8, 0.5, 0.2, 0.1. In some embodiments, the IE pre-elution buffer has pH that is the same as the IE pre-equilibrating buffer or IE equilibrating buffer. In some embodiments, the IE pre-elution buffer and the IE equilibrating buffer/IE pre-equilibrating buffer has a comparable pH (e.g., the pH difference less than about 0.5 or 0.2).

In some embodiments, the pre-elution buffer (e.g., a phosphate buffer) has an ion concentration (e.g., phosphate ion concentration) of about 1-50 mM, or 1-40 mM, 5-30 mM, 10-30 mM, 15-25 mM, 18-22 mM, or 20 mM. In some embodiments, the difference of ion concentration (e.g., phosphate ion concentration) of the IE pre-elution buffer and the IE pre-equilibrating buffer/IE equilibrating buffer is less than about 50 mM, 40 mM, 30 mM, 20 mM, 10 mM, 5 mM or 2 mM. In some embodiments, the IE pre-elution buffer has an ion concentration (e.g., phosphate ion concentration) that is the same as the IE pre-equilibrating buffer or IE equilibrating buffer.

In some embodiments, the IE pre-elution buffer (e.g., a phosphate buffer) further comprises a salt. In some embodiments, the salt is a sodium salt. In some embodiments, the salt is sodium chloride. In some embodiments, the concentration of the salt (e.g., sodium chloride) in the IE pre-elution buffer (e.g., a phosphate buffer) is about 1-700 mM, 10-600 mM, 50-500 mM, 100-350 mM, 150-300 mM, 175-275 mM, or 250-300 mM. In some embodiments, the concentration of the salt (e.g., sodium chloride) in the IE pre-elution buffer (e.g., a phosphate buffer) is about 1-300, 10-200, 20-100 mM, 30-80 mM, 40-60 mM, 45-55 mM, or 50 mM. In some embodiments, the concentration of the salt (e.g., sodium chloride) in the IE pre-elution buffer (e.g., a phosphate buffer) is about 1-350 mM, 10-300 mM, 50-200 mM, 70-180 mM, 100-150 mM, or 120 mM. In some embodiments, the concentration of the salt (e.g., sodium chloride) in the IE pre-elution buffer (e.g., a phosphate buffer) is at least about 20 mM, 40 mM, 50 mM, 75 mM, 100 mM, or 120 mM higher than the concentration of the salt (e.g., sodium chloride) in the IE pre-equilibrating buffer or the IE equilibrating buffer. In some embodiments, the concentration of the salt (e.g., sodium chloride) in the IE pre-elution buffer (e.g., a phosphate buffer) is at least about 10%, 20%, 30%, 40%, 50%, 60%, or 66% higher than the concentration of the salt (e.g., sodium chloride) in the IE pre-equilibrating buffer or the IE equilibrating buffer.

In some embodiments, about 1-20, 1-10, 1-8, 2-8, 2-6, or 2-5 column volumes of IE pre-elution buffer is applied to the column.

In some embodiments, the IE pre-elution step is carried out at about 4-30° C., 10-25° C. or room temperature.

In some embodiments, the IE pre-elution buffer is a phosphate buffer that has pH of about 7.0-9.5. In some embodiments, the IE pre-elution buffer is a phosphate buffer that has a phosphate ion concentration of about 10-30 mM, or 20 mM. In some embodiments, the IE pre-elution buffer is a phosphate buffer that has pH of about 7.0-9.5 and a phosphate ion concentration of about 10-30 mM, or 20 mM. In some embodiments, the phosphate buffer further comprises sodium chloride of about 200-300 mM (e.g., 250 mM), 20-100 mM (e.g., 50 mM), or 50-180 mM (e.g., 120 mM).

6) IE Elution Step

The IE chromatography provided herein comprises an IE elution step comprising eluting an ion exchange column with an IE elution buffer.

In some embodiments, the IE elution buffer is an anionic buffer. In some embodiments, the anionic buffer is selected from the group consisting of phosphate buffer, Tris-HCl buffer, Tricine buffer, Hepes buffer, glycine buffer, TEA buffer, and Barbitone sodium buffer. In some embodiments, the IE elution buffer is a phosphate buffer.

In some embodiments, the IE elution buffer and the IE pre-elution buffer/IE pre-equilibrating buffer/IE equilibrating buffer comprise a same kind of buffer (e.g. phosphate buffer). In some embodiments, the IE elution buffer, the IE pre-elution buffer, and the IE equilibration buffer/the IE pre-equilibration buffer comprise a same kind of buffer (e.g. phosphate buffer).

In some embodiments, the IE elution buffer (e.g., a phosphate buffer) has pH of about 6.0-10.0, 6.5-9.5, 7.0-9.5, 7.0-9.0, 7.0-8.5, 7.0-8.0, 7.2-7.8, 7.4-7.7, 7.5-7.6 or 7.6. In some embodiments, the difference of pH of the IE elution buffer and the IE pre-elution buffer is less than about 2, 1, 1.5, 1, 0.8, 0.5, 0.2, 0.1. In some embodiments, the difference of pH of the IE elution buffer and the IE pre-equilibrating buffer/IE equilibrating buffer is less than about 2, 1, 1.5, 1, 0.8, 0.5, 0.2, 0.1. In some embodiments, the IE elution buffer has pH that is the same as the IE pre-elution buffer, the IE pre-equilibrating buffer or the IE equilibrating buffer. In some embodiments, the IE elution buffer and the IE pre-elution buffer have comparable pH (e.g., the pH difference less than about 0.5 or 0.2). In some embodiments, the IE elution buffer and the IE equilibrating buffer/IE pre-equilibrating buffer have a comparable pH (e.g., the pH difference less than about 0.5 or 0.2).

In some embodiments, the IE elution buffer (e.g., a phosphate buffer) has an ion concentration (e.g., phosphate ion concentration) of about 1-50 mM, or 1-40 mM, 5-30 mM, 10-30 mM, 15-25 mM, 18-22 mM, or 20 mM. In some embodiments, the difference of ion concentration (e.g., phosphate ion concentration) of the IE elution buffer and the IE pre-elution buffer is less than about 50 mM, 40 mM, 30 mM, 20 mM, 10 mM, 5 mM or 2 mM. In some embodiments, the difference of the ion concentration (e.g., phosphate ion concentration) of the IE elution buffer and the IE pre-equilibrating buffer/IE equilibrating buffer is less than about 50 mM, 40 mM, 30 mM, 20 mM, 10 mM, 5 mM or 2 mM. In some embodiments, the IE elution buffer has an ion concentration (e.g., phosphate ion concentration) that is the same as the IE pre-elution buffer, the IE pre-equilibrating buffer or the IE equilibrating buffer.

In some embodiments, the IE elution buffer (e.g., a phosphate buffer) further comprises a salt. In some embodiments, the salt is a sodium salt. In some embodiments, the salt is sodium chloride. In some embodiments, the concentration of the salt (e.g., sodium chloride) in the IE elution buffer (e.g., a phosphate buffer) is about 50-1000 mM, 100-800 mM, or 200-700 mM. In some embodiments, the concentration of the salt (e.g., sodium chloride) in the IE elution buffer (e.g., a phosphate buffer) is about 250-750 mM, 300-700 mM, 350-650 mM, 400-600 mM, 450-600 mM, or 500-550 mM. In some embodiments, the concentration of the salt (e.g., sodium chloride) in the IE elution buffer (e.g., a phosphate buffer) is about 100-500 mM, 150-450 mM, 200-400 mM, 250-350 mM, 275-325 mM or 300 mM. In some embodiments, the concentration of the salt (e.g., sodium chloride) in the IE elution buffer (e.g., a phosphate buffer) is at least about 50 mM, 100 mM, 150 mM, 200 mM or 250 mM higher than the concentration of the salt (e.g., sodium chloride) in the IE pre-elution buffer. In some embodiments, the concentration of the salt (e.g., sodium chloride) in the IE elution buffer (e.g., a phosphate buffer) is at least about 50 mM, 100 mM, 150 mM, 200 mM, 250 mM, 300 mM, 350 mM, or 400 mM higher than the concentration of the salt (e.g., sodium chloride) in the IE pre-equilibrating buffer or the IE equilibrating buffer. In some embodiments, the concentration of the salt (e.g., sodium chloride) in the IE elution buffer (e.g., a phosphate buffer) is at least about 50%, 75%, 100%, 125%, 150%, 175%, 200%, 250%, 300%, 350%, 400%, 450%, or 500% higher than the concentration of the salt (e.g., sodium chloride) in the IE pre-elution buffer. In some embodiments, the concentration of the salt (e.g., sodium chloride) in the IE elution buffer (e.g., a phosphate buffer) is at least about 50%, 100%, 150%, 200%, 225%, or 250% higher than the concentration of the salt (e.g., sodium chloride) in the IE pre-equilibrating buffer or the IE equilibrating buffer.

In some embodiments, about 1-20, 1-10, 1-8, 2-8, 2-6, or 2-5 column volumes of IE elution buffer is applied to the column.

In some embodiments, the IE loading step is carried out at about 4-30° C., 10-25° C. or room temperature.

In some embodiments, the IE elution buffer is a phosphate buffer that has pH of about 7.0-9.5. In some embodiments, the IE elution buffer is a phosphate buffer that has a phosphate ion concentration of about 10-30 mM, or 20 mM. In some embodiments, the IE elution buffer is a phosphate buffer that has pH of about 7.0-9.5 and a phosphate ion concentration of about 10-30 mM, or 20 mM. In some embodiments, the phosphate buffer further comprises sodium chloride of about 400-650 mM (e.g., 500-550 mM), or 200-400 mM (e.g., 300 mM).

In some embodiments, the IE chromatography comprises more than one IE elution steps, and a first IE elution step comprises eluting the IE column with a first IE elution buffer, and wherein the second elution step comprises eluting the IE column with a second IE elution buffer. In some embodiments, the second IE elution buffer and the first IE elution buffer are both phosphate buffer, and/or have same or comparable pH (e.g., the pH difference less than about 0.5 or 0.2). In some embodiments, the first IE eluate and the second IE eluate respectively comprise a first virus composition and a second virus composition, and the first virus composition and the second virus composition have a different structure, purity or virus protein composition. In some embodiments, the first virus composition and the second virus composition have a different purity (i.e., the ratio of viral protein to the total protein). In some embodiments, the first virus composition and the second virus composition have a different one or more outer membrane proteins composition (e.g., different copy number of the one or more outer membrane proteins, e.g., different glycosylation of the one or more outer membrane proteins, e.g., different ratio of the one or more outer membrane proteins.) In some embodiments, the first virus composition and the second virus composition have a different virus titer. In some embodiments, the first virus composition and the second virus composition have a different amount of non-viral DNA and/or protein. In some embodiments, the non-viral DNA and/or protein is host cell DNA and/or protein. In some embodiment, the non-viral protein is a serum albumin. In some embodiments, the serum albumin is bovine serum albumin.

In some embodiments, the IE pre-equilibrating buffer, the equilibrating buffer, the pre-elution buffer and/or the elution buffer comprise the same kind of buffer, have same pH and different salt concentration. In some embodiments, the buffer is phosphate buffer.

In some embodiments, the virus is rabies virus, and the IE chromatography is an anion exchange chromatography (e.g., Capto-DEAE chromatography). In some embodiments, the IE pre-equilibrating buffer and/or IE equilibrating buffer is a phosphate buffer. In some embodiments, the phosphate ion concentration in the IE pre-equilibrating phosphate buffer or IE equilibrating phosphate buffer is about 5-50 mM, 10-40 mM, or 20 mM. In some embodiments, the IE pre-equilibrating buffer and/or the IE equilibrating buffer has pH of about 6.0-9.5, 7.0-9.5, 7.0-8.5, 7.0-8.0, 7.2-7.8, or 7.6. In some embodiments, the IE pre-equilibrating buffer and/or the IE equilibrating buffer comprises a salt. In some embodiments, the salt is sodium chloride. In some embodiments, the IE pre-equilibrating buffer and/or the IE equilibrating buffer comprises about 50-300, 100-200, 120-180, 140-160 or 150 mM NaCl. In some embodiments, about 5-40, 10-30, 15-25, or 20 column volumes of sample is loaded to the IE column. In some embodiments, the IE pre-elution buffer and/or the IE elution buffer is a phosphate buffer. In some embodiments, the phosphate ion concentration in the IE pre-elution phosphate buffer or the IE elution phosphate buffer is about 5-50 mM, 10-40 mM, or 20 mM. In some embodiments, the IE pre-elution buffer and/or the IE elution buffer has pH of about 6.0-9.5, 7.0-9.5, 7.0-8.5, 7.0-8.0, 7.2-7.8, or 7.6. In some embodiments, the IE pre-elution buffer and/or the IE elution buffer comprises a salt. In some embodiments, the salt is sodium chloride. In some embodiments, the IE pre-elution buffer comprises about 150-500, 200-400, 250-300 or 250 mM NaCl. In some embodiments, the IE elution buffer comprises about 200-800, 300-700, 400-600, 500-600, or 500-550 mM NaCl.

In some embodiments, the virus is Japanese encephalitis virus, and the IE chromatography is an anion exchange chromatography (e.g., Capto-DEAE chromatography). In some embodiments, the IE pre-equilibrating buffer and/or the IE equilibrating buffer is a phosphate buffer. In some embodiments, the phosphate ion concentration in the IE pre-equilibrating phosphate buffer or the IE equilibrating phosphate buffer is about 5-50 mM, 10-40 mM, or 20 mM. In some embodiments, the IE pre-equilibrating buffer and/or the IE equilibrating buffer has pH of about 6.0-9.5, 7.0-9.5, 7.0-8.5, 7.0-8.0, 7.2-7.8, or 7.6. In some embodiments, the IE pre-equilibrating buffer and/or the IE equilibrating buffer comprises a salt. In some embodiments, the salt is sodium chloride. In some embodiments, the IE pre-equilibrating buffer and/or IE equilibrating buffer does not comprise a salt (e.g., sodium chloride). In some embodiments, about 5-40, 10-30, 15-25, or 20 column volumes of sample is loaded to the IE column. In some embodiments, about 1-20, 1-10, 2-8, or 2-5 column volumes of equilibrating buffer is applied to the column after the sample is loaded. In some embodiments, the IE pre-elution buffer and/or IE elution buffer is a phosphate buffer. In some embodiments, the phosphate ion concentration in the IE pre-elution phosphate buffer or the IE elution phosphate buffer is about 5-50 mM, 10-40 mM, or 20 mM. In some embodiments, the IE pre-elution buffer and/or the IE elution buffer has pH of about 6.0-9.5, 7.0-9.5, 7.0-8.5, 7.0-8.0, 7.2-7.8, or 7.6. In some embodiments, the IE pre-elution buffer and/or the IE elution buffer comprises a salt. In some embodiments, the salt is sodium chloride. In some embodiments, the IE pre-elution buffer comprises about 1-250, 20-100, 30-70, 40-60, or 50 mM NaCl. In some embodiments, the IE elution buffer comprises about 100-500, 200-400, 250-350, or 300 mM NaCl.

In some embodiments, the virus is influenza virus, and the IE chromatography is an anion exchange chromatography (e.g., Capto-DEAE chromatography). In some embodiments, the IE pre-equilibrating buffer and/or the IE equilibrating buffer is a phosphate buffer. In some embodiments, the phosphate ion concentration in the IE pre-equilibrating phosphate buffer or the IE equilibrating phosphate buffer is about 5-50 mM, 10-40 mM, or 20 mM. In some embodiments, the IE pre-equilibrating buffer and/or the IE equilibrating buffer has pH of about 6.0-9.5, 7.0-9.5, 7.0-8.5, 7.0-8.0, 7.2-7.8, or 7.6. In some embodiments, the IE pre-equilibrating buffer and/or the IE equilibrating buffer comprises a salt. In some embodiments, the salt is sodium chloride. In some embodiments, the IE pre-equilibrating buffer and/or the IE equilibrating buffer does not comprise a salt (e.g., sodium chloride). In some embodiments, about 5-40, 10-30, 15-25, or 20 column volumes of sample is loaded to the IE column. In some embodiments, about 1-20, 1-10, 2-8, or 2-5 column volumes of IE equilibrating buffer is applied to the column after the sample is loaded. In some embodiments, the IE pre-elution buffer and/or the IE elution buffer is a phosphate buffer. In some embodiments, the phosphate ion concentration in the IE pre-elution phosphate buffer or the IE elution phosphate buffer is about 5-50 mM, 10-40 mM, or 20 mM. In some embodiments, the IE pre-elution buffer and/or the IE elution buffer has pH of about 6.0-9.5, 7.0-9.5, 7.0-8.5, 7.0-8.0, 7.2-7.8, or 7.6. In some embodiments, the IE pre-elution buffer and/or the IE elution buffer comprises a salt. In some embodiments, the salt is sodium chloride. In some embodiments, the IE pre-elution buffer comprises about 1-400, 50-250, 80-160, 100-150, or 120 mM NaCl. In some embodiments, the IE elution buffer comprises about 200-800, 300-700, 400-600, 450-550, or 500 mM NaCl.

B. Hydroxyapatite (HA) Chromatography

The methods described herein comprises an HA chromatography step comprising 1) an HA loading step comprising loading the biological sample or a post-IE chromatography sample to the hydroxyapatite column; and 2) an HA elution step, comprising eluting the HA column with an HA elution buffer. In some embodiments, the methods further comprise an HA equilibration step, comprising equilibrating the hydroxyapatite column with an HA equilibrating buffer; an HA pre-equilibration step, comprising pre-equilibrating a hydroxyapatite column with a hydroxyapatite pre-equilibrating buffer; and/or an HA pre-elution step, comprising pre-eluting the hydroxyapatite column with an HA pre-eluting buffer.

In some embodiments, the methods comprise a) an HA loading step, comprising loading the biological sample or a post-IE chromatography sample to the hydroxyapatite column; b) an HA equilibration step, comprising equilibrating the hydroxyapatite column with an HA equilibrating buffer; c) an HA elution step, comprising eluting the HA column with an HA elution buffer. In some embodiments, the methods comprise a) an HA pre-equilibration step, comprising pre-equilibrating a hydroxyapatite column with a hydroxyapatite pre-equilibrating buffer; b) an HA loading step, comprising loading the biological sample or a post-IE chromatography sample to the hydroxyapatite column; c) an HA equilibration step, comprising equilibrating the hydroxyapatite column with an HA equilibrating buffer; d) an HA elution step, comprising eluting the HA column with an HA elution buffer. In some embodiments, the methods comprise a) an HA pre-equilibration step, comprising pre-equilibrating a hydroxyapatite column with a hydroxyapatite pre-equilibrating buffer; b) an HA loading step, comprising loading the biological sample or a post-IE chromatography sample to the hydroxyapatite column; c) an HA elution step, comprising eluting the HA column with an HA elution buffer. In some embodiments, the methods comprise a) an HA loading step, comprising loading the biological sample or a post-IE chromatography sample to the hydroxyapatite column; b) an HA pre-elution step, comprising pre-eluting the hydroxyapatite column with an HA pre-eluting buffer; and c) an HA elution step, comprising eluting the HA column with an HA elution buffer. In some embodiments, the methods comprise a) an HA loading step, comprising loading the biological sample or a post-IE chromatography sample to the hydroxyapatite column; b) an HA equilibration step, comprising equilibrating the hydroxyapatite column with an HA equilibrating buffer; c) an HA pre-elution step, comprising pre-eluting the HA column with an HA pre-elution buffer; and d) an HA elution step, comprising eluting the HA column with an HA elution buffer.

In some embodiments, the methods comprise a) an HA pre-equilibration step, comprising pre-equilibrating a hydroxyapatite column with a hydroxyapatite pre-equilibrating buffer; b) an HA loading step, comprising loading the biological sample or a post-IE chromatography sample to the hydroxyapatite column; c) an HA equilibration step, comprising equilibrating the hydroxyapatite column with an HA equilibrating buffer; d) an HA pre-elution step, comprising pre-eluting the HA column with an HA pre-elution buffer; and e) an HA elution step, comprising eluting the HA column with an HA elution buffer.

In some embodiments, the virus comprises one or more outer membrane proteins. The conditions of the HA chromatography can be determined according to one or more of the following: a) the amino acid composition of the one or more outer membrane proteins; b) the copy number of the one or more outer membrane proteins; c) the degree of glycosylation of the one or more outer membrane proteins; and d) the degree of phosphorylation of the one or more outer membrane proteins on the surface of the enveloped virus. In some embodiments, the conditions of HA chromatography can be any one or more of the following: the type of the column, the specific column to use, the conditions (e.g., the ion concentration, pH, whether the specific buffer comprises a salt, the type of salt, salt concentration and/or the volume to apply) of the pre-equilibrating buffer, equilibrating buffer, pre-elution buffer, and/or elution buffer, and/or the volume of the virus sample or amount of the virus to load.

In some embodiments, the amino acid composition of the one or more outer membrane proteins comprises the composition of negatively charged amino acids (e.g., aspartic acid and glutamic acid) on the one or more outer membrane proteins. In some embodiments, the amino acid composition of the one or more outer membrane proteins comprises the composition of positively charged amino acids (e.g., arginine, histidine, and lysine) on the one or more outer membrane proteins. In some embodiments, the amino acid composition of the one or more outer membrane proteins comprises both negatively charged amino acids (e.g., aspartic acid, glutamic acid) on the one or more outer membrane proteins and positively charged amino acids (e.g., arginine, histidine, and lysine) on the one or more outer membrane proteins.

In some embodiments, the amino acid composition of the one or more outer membrane proteins is the weight ratio of the negatively charged amino acids (e.g., total aspartic acid and glutamic acid) on the one or more outer membrane proteins to the one or more outer membrane proteins. In some embodiments, the elution buffer comprises a phosphate buffer, wherein the phosphate ion concentration in the phosphate buffer is proportional to the weight ratio of the negatively charged amino acids (e.g., total aspartic acid and glutamic acid) on the one or more outer membrane proteins to the one or more outer membrane proteins.

In some embodiments, the amino acid composition of the one or more outer membrane proteins is the weight ratio of the positively charged amino acids (e.g., total arginine, histidine and lysine) on the one or more outer membrane proteins to the one or more outer membrane proteins. In some embodiments, the elution buffer comprises a calcium buffer, wherein the calcium ion concentration in the buffer is proportional to the weight ratio of the positively charged amino acids (e.g., total arginine, histidine and lysine) on the one or more outer membrane proteins to the one or more outer membrane proteins.

In some embodiments, the elution buffer has a phosphate buffer, and the concentration of the phosphate ion is proportional to the degree of the phosphorylation of the one or more outer membrane proteins.

In some embodiments, the conditions of HA chromatography are determined according to the copy number of the one or more outer membrane proteins. In some embodiments, the phosphate concentration in the elution buffer is proportional to the copy number of the one or more outer membrane proteins. In some embodiments, the copy number of the one or more outer membrane proteins is an average copy number of the one or more membrane protein on more than one virus (a batch of virus). In some embodiments, the copy number is a preferred copy number or a preferred range of copy number. In some embodiments, a virus vaccine with the preferred or preferred range of copy number of the one or more outer membrane proteins results in immunogenicity in an individual. In some embodiments, a virus vaccine with the preferred copy number or preferred range of copy number of the one or more outer membrane proteins results in superior immunogenicity in an individual (e.g., compared to a virus vaccine with a non-preferred copy number of the one or more outer membrane proteins).

In some embodiments, the one or more outer membrane proteins have two copy numbers, or two ranges of copy number (i.e., the first range of copy number and the second range of copy number) and/or two degrees of glycosylation or two ranges of degrees of glycosylation (i.e., the first range of glycosylation degree and the second range of glycosylation degree.) In some embodiments, the HA chromatography comprises a first elution step and a second elution step, wherein first elution step is to elute the first batch of virus comprising the first range of copy number and/or the first range of degree of glycosylation, and wherein the second elution step is to elute the second batch of virus comprising the second range of copy number and/or the second range of degree of glycosylation. In some embodiments, the phosphate ion concentration in the first elution buffer is proportional to the first range of copy number of the one or more outer membrane proteins and inversely proportional to the first range of the degree of glycosylation of the one or more outer membrane proteins. In some embodiments, the phosphate ion concentration in the second elution buffer is proportional to the second range of copy number of the one or more outer membrane proteins and inversely proportional to the second range of the degree of glycosylation of the one or more outer membrane proteins.

As discussed above, different copy numbers or preferred copy numbers (or preferred range of copy number) of the one or more outer membrane proteins can be represented by or converted to a particular (e.g., preferred) or a particular range (e.g., preferred range) of the relative percentage of the outer membrane protein in the total viral protein. The particular (e.g., preferred) or the particular range (e.g., preferred range) of the relative percentage of the outer membrane protein in the total viral protein (e.g., "the preferred ratio of outer membrane protein") can be any relative percentage or any range of relative percentages of the one or more outer membrane proteins. Similarly, a particular degree of glycosylation (e.g., a preferred degree of glycosylation, a preferred range of degree of glycosylation) can be any degree or range of degree of glycosylation on the one or more outer membrane proteins. The particular/preferred ratio of the outer membrane protein and the particular/preferred degree of glycosylation can be determined according to the purpose of the viral particles. Exemplary purposes of using the virus particles include for vaccine preparation and for research. In some embodiments, the virus that has the particular/preferred ratio of the outer membrane protein has higher potency than the same kind of virus that does not have the particular/preferred ratio of the outer membrane protein. In some embodiments, a vaccine with the virus that has the particular/preferred ratio of the outer membrane protein result in higher immunogenicity than a vaccine with the same kind of virus that do not have the particular/preferred ratio of the outer membrane protein. In some embodiments, the virus that has the particular/preferred degree of glycosylation on the outer membrane protein has higher potency than the same kind of virus that does not have the particular/preferred degree of glycosylation on the outer membrane protein. In some embodiments, a vaccine with the virus that has the particular/preferred degree of glycosylation on the outer membrane protein result in higher immunogenicity than a vaccine with the same kind of virus that do not have the particular/preferred degree of glycosylation on the outer membrane protein.

1) HA Column

Various hydroxyapatite chromatographic resins are available commercially, and any available form of the material can be used in the practice of the subject matter of this application. In some embodiments, the hydroxyapatite is in a crystalline form. In some embodiments, the hydroxyapatite is agglomerated to form particles and sintered at high temperatures into a stable porous ceramic mass.

The particle size of the hydroxyapatite may vary widely. In some embodiments, the particle size ranges from 1 μm to 1,000 μm in diameter, or from 10 μm to 100 μm.

Any suitable hydroxyapatite column may be utilized. Exemplary hydroxyapatite include ceramic hydroxyapatite column (CHT Type I and Type II, Bio-Rad Laboratories, Hercules, Calif.), HA Ultrogel hydroxyapatite column (Pall Corp., East Hills, N.Y.), and ceramic fluoroapatite column (CFT Type I and Type II, Bio-Rad Laboratories, Hercules, Calif.).

In some embodiments, the hydroxyapatite is loose and packed in a column. In some embodiments, the hydroxyapatite is in a continuous annular chromatograph. In some embodiments, the hydroxyapatite is ceramic hydroxyapatite. In some embodiments, ceramic hydroxyapatite is packed in a column. In some embodiments, a column diameter of at least 0.5 cm with a bed height of about 20 cm is used for small scale purification. In some embodiments, a column diameter of from about 35 cm to about 60 cm is used. In some embodiments, a column diameter of from about 60 cm to about 85 cm is used. In some embodiments, a column diameter of from about 85 cm to about 120 cm (e.g., 100 cm) is used. In some embodiments, a column diameter of more than about 120 cm is used.

2) HA Pre-Equilibration Step

In some embodiments, the HA chromatography comprises an HA pre-equilibration step comprising pre-equilibrating a hydroxyapatite column with an HA pre-equilibrating buffer.

In some embodiments, the HA pre-equilibrating buffer is an anionic buffer. In some embodiments, the anionic buffer is selected from the group consisting of phosphate buffer, Tris-HCl buffer, Tricine buffer, Hepes buffer, glycine buffer, TEA buffer, and Barbitone sodium buffer. In some embodiments, the pre-equilibrating buffer is a phosphate buffer.

In some embodiments, the HA pre-equilibrating buffer has pH of about 6.0-10.0, 6.5-9.5, 7.0-9.5, 7.0-9.0, 7.0-8.5, 7.0-8.0, 7.2-7.8, 7.4-7.7, 7.5-7.6 or 7.6.

In some embodiments, the HA pre-equilibrating buffer (e.g., phosphate buffer) has a ion concentration (e.g., phosphate ion concentration) of about 1-50 mM, or 1-40 mM, 5-30 mM, 10-30 mM, 15-25 mM, 18-22 mM, or 20 mM. In some embodiments, the HA pre-equilibrating buffer (e.g., phosphate buffer) has a ion concentration (e.g., phosphate ion concentration) of about 1-20 mM, or 1-10 mM, 2-8 mM, 4-6 mM, or 5 mM.

In some embodiments, the HA pre-equilibrating buffer (e.g., a phosphate buffer) further comprises a salt. In some embodiments, the salt is a sodium salt. In some embodiments, the salt is sodium chloride. In some embodiments, the concentration of the salt (e.g., sodium chloride) in the HA pre-equilibrating buffer (e.g., a phosphate buffer) is about 50 mM to about 220 mM. In some embodiments, the concentration of the salt (e.g., sodium chloride) in the HA pre-equilibrating buffer (e.g., a phosphate buffer) is about 1-500 mM, 10-400 mM, 50-300 mM, 100-200 mM, 125-175 mM, or 150 mM. In some embodiments, the concentration of the salt (e.g., sodium chloride) in the HA pre-equilibrating buffer (e.g., a phosphate buffer) is about 100-1000 mM, 300-800 mM, 400-700 mM, 500-600 mM, or 550 mM. In some embodiments, the HA pre-equilibrating buffer (e.g., a phosphate buffer) does not comprise a salt (e.g., a sodium salt, sodium chloride).

In some embodiments, about 1-20, 1-10, 1-8, 2-8, 2-6, or 2-5 column volumes of pre-equilibrating buffer is applied to the column.

In some embodiments, the HA pre-equilibrating buffer is a phosphate buffer that has pH of about 7.0-9.5. In some embodiments, the HA pre-equilibrating buffer is a phosphate buffer that has a phosphate ion concentration of about 1-50 mM, 10-30 mM, 1-10 mM, 2-8 mM, 4-6 mM, 10 mM-30 mM, 15-25 mM, 5 mM or 20 mM. In some embodiments, the HA pre-equilibrating buffer is a phosphate buffer that has pH of about 7.0-9.5 and a phosphate ion concentration of about 10-30 mM, 20 mM, 2-8 mM, 4-6 mM, or 5 mM. In some embodiments, the phosphate buffer further comprises sodium chloride of about 100-200 mM (e.g., 150 mM) or 500-600 (e.g., 550 mM).

In some embodiments, the HA pre-equilibrating step is carried out at about 4-30° C., 10-25° C. or room temperature.

3) HA Loading Step

A virus sample (e.g., a supernatant containing virus harvested from a culture, e.g., an eluate collected from a IE chromatography) is loaded to the column in the HA chromatography. In some embodiments, the column is pre-equilibrated prior to the loading of the virus sample. In some embodiments, the column is not pre-equilibrated prior to the loading of the virus sample. In some embodiments, the virus sample is pretreated prior to the loading. In some embodiments, the virus sample is clarified prior to the loading. In some embodiments, the virus sample is clarified through microfiltration before being loaded to the column. In some embodiments, the microfiltration comprises filtrating the virus sample through a membrane with a pore size of about 0.1-1 μm or 1-1.5 μm.

In some embodiments, about 1-50, 1-40, 1-30, 1-20 or 5-20 column volumes of the virus sample are loaded to the HA column.

In some embodiments, the HA loading step is carried out at about 4-30° C., 10-25° C. or room temperature.

4) HA Equilibrating Step

In some embodiments, the HA chromatography comprises an HA equilibration step comprising equilibrating a hydroxyapatite column with an HA equilibrating buffer.

In some embodiments, the HA equilibrating buffer is an anionic buffer. In some embodiments, the anionic buffer is selected from the group consisting of phosphate buffer, Tris-HCl buffer, Tricine buffer, Hepes buffer, glycine buffer, TEA buffer, and Barbitone sodium buffer. In some embodiments, the equilibrating buffer is a phosphate buffer.

In some embodiments, the HA equilibrating buffer is the same as the HA pre-equilibrating buffer.

In some embodiments, the HA equilibrating buffer (e.g., a phosphate buffer) has pH of about 6.0-10.0, 6.5-9.5, 7.0-9.5, 7.0-9.0, 7.0-8.5, 7.0-8.0, 7.2-7.8, 7.4-7.7, 7.5-7.6 or 7.6.

In some embodiments, the HA equilibrating buffer (e.g., phosphate buffer) has a ion concentration (e.g., phosphate ion concentration) of about 1-50 mM, or 1-40 mM, 5-30 mM, 10-30 mM, 15-25 mM, 18-22 mM, or 20 mM. In some embodiments, the HA equilibrating buffer (e.g., phosphate buffer) has a ion concentration (e.g., phosphate ion concentration) of about 1-20 mM, or 1-10 mM, 2-8 mM, 4-6 mM, or 5 mM.

In some embodiments, the HA equilibrating buffer (e.g., a phosphate buffer) further comprises a salt. In some embodiments, the salt is a sodium salt. In some embodiments, the salt is sodium chloride. In some embodiments, the concentration of the salt (e.g., sodium chloride) in the HA equilibrating buffer (e.g., a phosphate buffer) is about 50 mM to about 220 mM. In some embodiments, the concentration of the salt (e.g., sodium chloride) in the HA equilibrating buffer (e.g., a phosphate buffer) is about 1-500 mM, 10-400 mM, 50-300 mM, 100-200 mM, 125-175 mM, or 150 mM. In some embodiments, the concentration of the salt (e.g., sodium chloride) in the HA equilibrating buffer (e.g., a phosphate buffer) is about 100-1000 mM, 300-800 mM, 400-700 mM, 500-600 mM, or 550 mM. In some embodiments, the HA equilibrating buffer (e.g., a phosphate buffer) does not comprise a salt (e.g., a sodium salt, sodium chloride).

In some embodiments, about 1-20, 1-10, 1-8, 2-8, 2-6, or 2-5 column volumes of equilibrating buffer is applied to the column.

In some embodiments, the HA equilibrating buffer is a phosphate buffer that has pH of about 7.0-9.5. In some embodiments, the HA equilibrating buffer is a phosphate buffer that has a phosphate ion concentration of about 1-50 mM, 10-30 mM, 1-10 mM, 2-8 mM, 4-6 mM, 10 mM-30 mM, 15-25 mM, 5 mM or 20 mM. In some embodiments, the HA equilibrating buffer is a phosphate buffer that has pH of about 7.0-9.5 and a phosphate ion concentration of about 10-30 mM, 20 mM, 2-8 mM, 4-6 mM, or 5 mM. In some embodiments, the phosphate buffer further comprises sodium chloride of about 100-200 mM (e.g., 150 mM) or 500-600 (e.g., 550 mM).

In some embodiments, the HA-equilibrating step is carried out at about 4-30° C., 10-25° C. or room temperature.

5) HA Pre-Elution Step

In some embodiments, the HA chromatography comprises an HA pre-elution step comprising pre-eluting a hydroxyapatite column with an HA pre-elution buffer.

In some embodiments, the HA pre-elution buffer is an anionic buffer. In some embodiments, the anionic buffer is selected from the group consisting of phosphate buffer, Tris-HCl buffer, Tricine buffer, Hepes buffer, glycine buffer, TEA buffer, and Barbitone sodium buffer. In some embodiments, the HA pre-elution buffer is a phosphate buffer.

In some embodiments, the HA pre-elution buffer and the HA pre-equilibrating buffer/IE equilibrating buffer comprise a same kind of buffer (e.g. phosphate buffer).

In some embodiments, the pre-elution buffer (e.g., a phosphate buffer) has pH of about 6.0-10.0, 6.5-9.5, 7.0-9.5, 7.0-9.0, 7.0-8.5, 7.0-8.0, 7.2-7.8, 7.4-7.7, 7.5-7.6 or 7.6. In some embodiments, the difference of pH of the HA pre-elution buffer and the HA pre-equilibrating buffer/IE equilibrating buffer is less than about 2, 1, 1.5, 1, 0.8, 0.5, 0.2, 0.1. In some embodiments, the HA pre-elution buffer has pH that is the same as the HA pre-equilibrating buffer or HA equilibrating buffer. In some embodiments, the HA pre-elution buffer and the HA equilibrating buffer/IE pre-equilibrating buffer has a comparable pH (e.g., the pH difference less than about 0.5 or 0.2).

In some embodiments, the HA pre-elution buffer (e.g., a phosphate buffer) has an ion concentration (e.g., phosphate ion concentration) of about 1-300 mM. In some embodiments, the HA pre-elution buffer (e.g., a phosphate buffer) has an ion concentration (e.g., phosphate ion concentration) of about 1-50 mM, or 1-40 mM, 5-30 mM, 10-30 mM, 15-25 mM, 18-22 mM, or 20 mM. In some embodiments, the HA pre-elution buffer (e.g., a phosphate buffer) has an ion concentration (e.g., phosphate ion concentration) of about 1-20 mM, or 1-10 mM, 2-8 mM, 4-6 mM, or 5 mM. In some embodiments, the HA pre-elution buffer (e.g., a phosphate buffer) has an ion concentration (e.g., phosphate ion concentration) of about 1-200 mM, 20-180 mM, 30-150 mM, 40-120 mM, 50-100 mM, 40-60 mM, 80-120 mM, 50 mM, or 100 mM. In some embodiments, the ion concentration (e.g., phosphate ion concentration) of the HA pre-elution buffer is higher than ion concentration (e.g., phosphate ion concentration) of the HA pre-equilibrating buffer/HA equilibrating buffer. In some embodiments, the difference in ion concentration (e.g., phosphate ion concentration) of the HA pre-elution buffer and the HA pre-equilibrating buffer/IE equilibrating buffer is about or less than about 80 mM, 70 mM, 60 mM, 50 mM, 40 mM, 30 mM, 20 mM, 10 mM, 5 mM or 2 mM. In some embodiments, the difference of ion concentration (e.g., phosphate ion concentration) of the HA pre-elution buffer and the HA pre-equilibrating buffer/IE equilibrating buffer is about 0.1-100 mM, 20-80 mM, 30-70 mM, 20-40 mM, or 70-90 mM. In some embodiments, the HA pre-elution buffer has an ion concentration (e.g., phosphate ion concentration) that is the same as the HA pre-equilibrating buffer or HA equilibrating buffer. In some embodiments, the ion concentration (e.g., phosphate ion concentration) of the HA pre-elution buffer is at least about 50%, 100%, 150%, 200%, 300%, or 400% higher than the HA pre-equilibrating buffer or HA equilibrating buffer.

In some embodiments, the HA pre-elution buffer (e.g., a phosphate buffer) further comprises a salt. In some embodiments, the salt is a sodium salt. In some embodiments, the salt is sodium chloride. In some embodiments, the concentration of the salt (e.g., sodium chloride) in the HA pre-elution buffer (e.g., a phosphate buffer) is about 1-500 mM, 10-400 mM, 50-300 mM, 100-200 mM, 125-175 mM, or 150 mM. In some embodiments, the difference in the concentration of the salt (e.g., sodium chloride) of the HA pre-elution buffer and the HA pre-equilibrating buffer/IE equilibrating buffer is less than 50 mM, 20 mM, 10 mM, 5 mM, or 2 mM. In some embodiments, the HA pre-elution buffer (e.g., a phosphate buffer) does not comprise a salt (e.g., a sodium salt, sodium chloride).

In some embodiments, about 1-20, 1-10, 1-8, 2-8, 2-6, or 2-5 column volumes of HA pre-elution buffer is applied to the column.

In some embodiments, the HA pre-elution step is carried out at about 4-30° C., 10-25° C. or room temperature.

In some embodiments, the HA pre-elution buffer is a phosphate buffer that has pH of about 7.0-9.5. In some embodiments, the HA pre-elution buffer is a phosphate buffer that has a phosphate ion concentration of about 10-30 mM, or 20 mM. In some embodiments, the HA pre-elution buffer is a phosphate buffer that has a phosphate ion concentration of about 2-8 mM, or 5 mM. In some embodiments, the HA pre-elution buffer is a phosphate buffer that has a phosphate ion concentration of about 40-120 mM (e.g., 40-60 mM, 80-120 mM), 50-100 mM, 50 mM or 100 mM. In some embodiments, the HA pre-elution buffer is a phosphate buffer that has pH of about 7.0-9.5 and a phosphate ion concentration of about 10-30 mM, 20 mM, 2-8 mM, 5 mM, 40-120 mM (e.g., 40-60 mM, 80-120 mM), 50-100 mM, 50 mM, or 100 mM. In some embodiments, the phosphate buffer further comprises sodium chloride of about 100-200 mM (e.g., 150 mM), or does not comprise sodium chloride.

6) HA Elution Step

The HA chromatography provided herein comprises an HA elution step comprising eluting a hydroxyapatite column with an HA elution buffer.

In some embodiments, the HA elution buffer is an anionic buffer. In some embodiments, the anionic buffer is selected from the group consisting of phosphate buffer, Tris-HCl buffer, Tricine buffer, Hepes buffer, glycine buffer, TEA buffer, and Barbitone sodium buffer. In some embodiments, the HA elution buffer is a phosphate buffer.

In some embodiments, the HA elution buffer and the HA pre-elution buffer/IE pre-equilibrating buffer/IE equilibrating buffer comprise a same kind of buffer (e.g. phosphate buffer). In some embodiments, the HA elution buffer, the HA pre-elution buffer, and the HA equilibration buffer/the HA pre-equilibration buffer comprise a same kind of buffer (e.g. phosphate buffer).

In some embodiments, the HA elution buffer (e.g., a phosphate buffer) has pH of about 6.0-10.0, 6.5-9.5, 7.0-9.5, 7.0-9.0, 7.0-8.5, 7.0-8.0, 7.2-7.8, 7.4-7.7, 7.5-7.6 or 7.6. In some embodiments, the difference of pH of the HA elution buffer and the HA pre-elution buffer is less than about 2, 1, 1.5, 1, 0.8, 0.5, 0.2, 0.1. In some embodiments, the difference of pH of the HA elution buffer and the HA pre-equilibrating buffer/IE equilibrating buffer is less than about 2, 1, 1.5, 1, 0.8, 0.5, 0.2, 0.1. In some embodiments, the HA elution buffer has pH that is the same as the HA pre-elution buffer, the HA pre-equilibrating buffer or the HA equilibrating buffer. In some embodiments, the HA elution buffer and the HA pre-elution buffer have comparable pH (e.g., the pH difference less than about 0.5 or 0.2). In some embodiments, the HA elution buffer and the HA equilibrating buffer/IE pre-equilibrating buffer have a comparable pH (e.g., the pH difference less than about 0.5 or 0.2).

In some embodiments, the HA elution buffer (e.g., a phosphate buffer) has an ion concentration (e.g., phosphate ion concentration) of about 50-500 mM, 75-350 mM, 80-320 mM, 90-310 mM, 100-300 mM, 80-120 mM, 150-250 mM, 180-220 mM, 250-350 mM, 280-380 mM, 75-225 mM, 100 mM, 200 mM, or 300 mM. In some embodiments, the HA elution buffer (e.g., a phosphate buffer) has an ion concentration (e.g., phosphate ion concentration) of about 200 mM. In some embodiments, the HA elution buffer (e.g., a phosphate buffer) has an ion concentration (e.g., phosphate ion concentration) of about 100-200 mM, 125-175 mM, or 150 mM. In some embodiments, the ion concentration (e.g., phosphate ion concentration) of the HA elution buffer is higher than ion concentration (e.g., phosphate ion concentration) of the HA pre-elution or the HA pre-equilibrating buffer/HA equilibrating buffer. In some embodiments, the difference in ion concentration (e.g., phosphate ion concentration) of the HA elution buffer and the HA pre-elution buffer is about or at least about 10-400 mM, 30-300 mM, 50-250 mM, 120-180 mM, 150-200 mM, 100 mM, 150 mM, or 180 mM. In some embodiments, the difference in ion concentration (e.g., phosphate ion concentration) of the HA elution buffer and the HA pre-equilibrating buffer/IE equilibrating buffer is about or at least about 50-500 mM, 70-300 mM, 80-280 mM, 100-200 mM, 140-180 mM, 145 mM, or 180 mM. In some embodiments, the ion concentration (e.g., phosphate ion concentration) of the HA elution buffer is at least about 1.5-fold, 2-fold, 3-fold, 4-fold, 5-fold, 6-fold, 10-fold, 15-fold, 20-fold, 25-fold, or 30-fold of the ion concentration (e.g., phosphate ion concentration) of the HA pre-elution buffer. In some embodiments, the ion concentration (e.g., phosphate ion concentration) of the HA elution buffer is at least about 2-fold, 5-fold, 10-fold, 15-fold, 20-fold, 25-fold, or 30-fold of the ion concentration (e.g., phosphate ion concentration) of the HA pre-equilibrating buffer/IE equilibrating buffer.

In some embodiments, the HA elution buffer (e.g., a phosphate buffer) further comprises a salt. In some embodiments, the salt is a sodium salt. In some embodiments, the salt is sodium chloride. In some embodiments, the concentration of the salt (e.g., sodium chloride) in the HA elution buffer (e.g., a phosphate buffer) is about 1-500 mM, 10-400 mM, 50-300 mM, 100-200 mM, 125-175 mM, or 150 mM. In some embodiments, the difference in the concentration of the salt (e.g., sodium chloride) of the HA elution buffer and the HA pre-elution buffer is less than 50 mM, 20 mM, 10 mM, 5 mM, or 2 mM. In some embodiment, the difference in the concentration of the salt (e.g., sodium chloride) of the HA elution buffer and the HA pre-equilibrating buffer/IE equilibrating buffer is less than 50 mM, 20 mM, 10 mM, 5 mM, or 2 mM. In some embodiments, the HA pre-elution buffer (e.g., a phosphate buffer) does not comprise a salt (e.g., a sodium salt, sodium chloride).

In some embodiments, about 1-20, 1-10, 1-8, 2-8, 2-6, or 2-5 column volumes of HA elution buffer is applied to the column.

In some embodiments, the HA elution step is carried out at about 4-30° C., 10-25° C. or room temperature.

In some embodiments, the pre-elution buffer and the elution buffer comprise a same buffer. In some embodiments, the pre-elution buffer and the elution buffer has a pH difference less than about 2, 1.5, 1, 0.8, 0.5, or 0.2. In some embodiments, the pre-elution buffer and the elution buffer has a comparable pH (e.g., the pH difference less than 0.5).

In some embodiments, the HA pre-elution buffer and the HA elution buffer both comprise a salt. In some embodiments, the HA pre-elution buffer and the HA elution buffer have a same salt. In some embodiments, the salt is a sodium salt. In some embodiments, the salt is sodium chloride. In some embodiments, the salt in the HA pre-elution buffer has a same salt concentration as the salt in the HA elution buffer. In some embodiments, the sodium salt (e.g., sodium chloride) in the pre-elution buffer has a higher or lower concentration than in the elution buffer.

In some embodiments, the HA chromatography comprises more than one elution steps, wherein a first elution step comprises eluting the HA column with a first elution buffer, and wherein the second elution step comprises eluting the HA column with a second elution buffer. In some embodiments, the second elution buffer and the first elution buffer are both phosphate buffer, and/or have same pH. In some embodiments, the first eluate and the second eluate respectively comprise a first virus composition and a second virus composition, wherein the first virus composition and the second virus composition have a different structure, purity or virus protein composition. In some embodiments, the first virus composition and the second virus composition have a different purity (e.g., the ratio of viral protein to the total protein). In some embodiments, the first virus composition and the second virus composition have a different one or more outer membrane proteins composition (e.g., different copy number of the one or more outer membrane proteins, e.g., different glycosylation of the one or more outer membrane proteins, e.g., different ratio of the one or more outer membrane proteins.) In some embodiments, the first virus composition and the second virus composition have a different virus titer. In some embodiments, first virus composition and the second virus composition have a different amount of non-viral DNA and/or protein. In some embodiments, the non-viral DNA and/or protein is host cell DNA and/or protein. In some embodiment, the non-viral protein is a serum albumin. In some embodiments, the serum albumin is bovine serum albumin.

In some embodiments, the HA pre-equilibrating buffer, the HA equilibrating buffer, the HA pre-elution buffer and/or the HA elution buffer are same kind of buffer and/or have same pH. In some embodiments, the buffer is phosphate buffer.

In some embodiments, the virus is rabies virus. In some embodiments, the HA chromatography is a CHT chromatography. In some embodiments, the pre-equilibrating buffer and/or equilibrating buffer is a phosphate buffer. In some embodiments, the phosphate ion concentration in the pre-equilibrating phosphate buffer or equilibrating phosphate buffer is about 5-50 mM, 10-40 mM, 10-30 mM, 15-25 mM, or 20 mM. In some embodiments, the pre-equilibrating buffer and/or equilibrating buffer has pH of about 6.0-9.5, 7.0-9.5, 7.0-8.5, 7.0-8.0, 7.2-7.8, or 7.6. In some embodiments, the pre-equilibrating buffer and/or equilibrating buffer comprises a salt. In some embodiments, the salt is sodium chloride. In some embodiments, the pre-equilibrating buffer and/or equilibrating buffer comprises about 50-300, 100-200, 120-180, 140-160 or 150 mM NaCl. In some embodiments, the pre-equilibrating buffer and/or equilibrating buffer comprises about 200-800, 300-700, 400-650, 500-600 or 550 mM NaCl. In some embodiments, the pre-equilibrating buffer and/or equilibrating buffer does not comprise a salt (e.g., sodium chloride). In some embodiments, about 5-40, 10-30, 15-25, or 20 column volumes of sample is loaded to the HA column. In some embodiments, the pre-elution buffer and/or elution buffer is a phosphate buffer. In some embodiments, the phosphate ion concentration in the pre-elution phosphate buffer or elution phosphate buffer is about 20-100 mM, 30-70 mM, 40-60 mM, or 50 mM. In some embodiments, the phosphate ion concentration in the elution phosphate buffer or elution phosphate buffer is about 100-300, 125-275, 150-250, 175-225, or 200 mM. In some embodiments, the pre-elution buffer and/or the elution buffer has pH of about 6.0-9.5, 7.0-9.5, 7.0-8.5, 7.0-8.0, 7.2-7.8, or 7.6. In some embodiments, the pre-elution buffer and/or the elution buffer comprises a salt. In some embodiments, the salt is sodium chloride. In some embodiments, the pre-elution buffer or the elution buffer comprises about 50-300, 100-200, 125-175, or 150 mM NaCl. In some embodiments, the pre-elution buffer or the elution buffer does not comprise a salt (e.g., sodium chloride).

In some embodiments, the virus is Japanese encephalitis virus. In some embodiments, the HA chromatography is a CHT chromatography. In some embodiments, the pre-equilibrating buffer and/or equilibrating buffer is a phosphate buffer. In some embodiments, the phosphate ion concentration in the pre-equilibrating phosphate buffer or equilibrating phosphate buffer is about 0-20 mM, 1-15 mM, 1-10 mM, 3-8 mM, 4-7 mM, or 5 mM. In some embodiments, the pre-equilibrating buffer and/or equilibrating buffer has pH of about 6.0-9.5, 7.0-9.5, 7.0-8.5, 7.0-8.0, 7.2-7.8, or 7.6. In some embodiments, the pre-equilibrating buffer and/or equilibrating buffer does not comprise a salt (e.g., sodium chloride). In some embodiments, about 5-40, 10-30, 15-25, or 20 column volumes of sample is loaded to the HA column. In some embodiments, the pre-elution buffer and/or elution buffer is a phosphate buffer. In some embodiments, the phosphate ion concentration in the pre-elution phosphate buffer or elution phosphate buffer is about 0-20 mM, 1-15 mM, 1-10 mM, 3-8 mM, 4-7 mM, or 5 mM. In some embodiments, the phosphate ion concentration in the elution phosphate buffer or elution phosphate buffer is about 50-300, 100-200, 125-175, or 150 mM. In some embodiments, the pre-elution buffer and/or the elution buffer has pH of about 6.0-9.5, 7.0-9.5, 7.0-8.5, 7.0-8.0, 7.2-7.8, or 7.6. In some embodiments, the pre-elution buffer or the elution buffer does not comprise a salt (e.g., sodium chloride).

In some embodiments, the virus is influenza virus. In some embodiments, the HA chromatography is a CHT chromatography. In some embodiments, the pre-equilibrating buffer and/or equilibrating buffer is a phosphate buffer. In some embodiments, the phosphate ion concentration in the pre-equilibrating phosphate buffer or equilibrating phosphate buffer is about 5-50 mM, 10-40 mM, 10-30 mM, 15-25 mM, or 20 mM. In some embodiments, the pre-equilibrating buffer and/or equilibrating buffer has pH of about 6.0-9.5, 7.0-9.5, 7.0-8.5, 7.0-8.0, 7.2-7.8, or 7.6. In some embodiments, the pre-equilibrating buffer and/or equilibrating buffer does not comprise a salt (e.g., sodium chloride). In some embodiments, about 5-40, 10-30, 15-25, or 20 column volumes of sample is loaded to the HA column. In some embodiments, the pre-elution buffer and/or elution buffer is a phosphate buffer. In some embodiments, the phosphate ion concentration in the pre-elution phosphate buffer or elution phosphate buffer is about 5-50 mM, 10-40 mM, 10-30 mM, 15-25 mM, or 20 mM. In some embodiments, the phosphate ion concentration in the elution phosphate buffer or elution phosphate buffer is about 100-300, 125-275, 150-250, 175-225, or 200 mM. In some embodiments, the pre-elution buffer and/or the elution buffer has pH of about 6.0-9.5, 7.0-9.5, 7.0-8.5, 7.0-8.0, 7.2-7.8, or 7.6. In some embodiments, the pre-elution buffer or the elution buffer does not comprise a salt (e.g., sodium chloride).

C. Virus inactivation

In some embodiments, the method further comprises a step of inactivating virus. In some embodiments, the virus inactivation step is carried out prior to the IE chromatography, the HA chromatography, or both. In some embodiments, the virus inactivation is carried out after the IE chromatography, the HA chromatography, or both.

In some embodiments, the inactivation step comprises contacting the virus with an inactivation agent. In some embodiments, the inactivation agent disrupts a spatial structure of the one or more outer membrane proteins. In some embodiments, the inactivation agent alters the genome of virus or the structure of the virus genome. The viral inactivation can be carried out by means of chemical agents well known to those skilled in the art, such as formaldehyde, glutaraldehyde or β-propiolactone. It is also possible to use the inactivation method as described in WO 2005/093049, which consists in bringing the purified viral solution into contact with a photoactivatable hydrophobic compound and in exposing this mixture to light. Among the photoactivatable hydrophobic compounds, mention is made of azidobenzene, 1-azidonaphthalene, 4-azido-2-nitro-1-(phenylthio)benzene, 1-azido-4-iodobenzene, 1-azido-5-iodonaphthalene, 3-phenyl-3H-diazirene, 3-phenyl-3-(trifluoromethyl)-3H-diazirene, 3-(3-iodophenyl)-3-(trifluoromethyl)-3H-diazirene, 1-azidopyrene, adamantine diazirene, 12-(4-azido-2-nitrophenoxy)stearic acid, w-(m-diazirinophenoxy) fatty acid, 12-[(azidocarbonyl)oxy] stearic acid, 12-azidostearic acid, 11-(3-azidophenoxy)undecanoic acid or w-(m-diazirinophenoxy)undecanoic acid or 1,5-iodonaphtyl azide.

In some embodiments, β-propiolactone (BPL) is used. In some embodiments, the inactivation of the virus is carried out by means of a solution of β-propiolactone diluted to between 1/1000-1/10000, 1/2000-1/8000, 1/3000-1/6000, or 1/3500-1/4000 (final volume concentration in the solution containing the purified virus).

In some embodiments, the inactivation step is performed at a temperature of approximately 5-25° C., 10-15° C., or 12° C. In some embodiments, the inactivation step is performed at a temperature between 20-37° C. In some embodiments, the inactivation of the virus is carried out in a time period ranging from about 4-72 hours, 6-60 hours, or 12-48 hours.

In some embodiments, the β-propiolactone is hydrolyzed. In some embodiments, the β-propiolactone is hydrolyzed by heating the solution at a temperature of approximately 25-40° C., 30-40° C., 35-40° C., or 37° C. for 0.5-8 hours, 1-6 hours, 2-4 hours, or 2 hours. In some embodiments, the pH of the virus solution immediately prior to or during β-propiolactone treatment is at least 7, or 7.5.

D. Clarification

In some embodiments, the biological sample is subjected to a clarification step. In some embodiments, the clarification step is carried out prior to the IE chromatography, HA chromatography or both. In some embodiments, the clarification step is carried out after the IE chromatography, HA chromatography or both.

In some embodiments, the clarification step comprises microfiltration through a microfilter. In some embodiments, the microfilter has a pore size of about or at least about 0.1 μm, 0.2 μm, 0.7 μm, 0.8 μm, 0.9 μm, 1.0 μm, 1.1 μm, 1.2 μm, 1.3 μm, 1.4 μm, 1.5 μm, 1.6 μm, 1.7 μm, 1.8 μm, 1.9 μm, 2.0 μm. In some embodiments, the microfilter has a pore size of about 0.1-2.0 μm, 0.25-2.0 μm, 0.5-2.0 μm, 0.75-2.0 μm, 1.0-2.0 μm, 1.25-2.0 μm, 1.5-2.0 μm, 1.75-2.0 μm, 0.1-1.75 μm, 0.25-1.75 μm, 0.5-1.75 μm, 0.75-1.75 μm, 1.0-1.75 μm, 1.25-1.75 µm, 1.5-1.75 µm, 0.1-1.5 µm, 0.25-1.5 µm, 0.5-1.5 µm, 0.75-1.5 µm, 1.0-1.5 µm, 1.25-1.5 µm, 0.1-1.25 µm, 0.25-1.25 µm, 0.5-1.25 µm, 0.75-1.25 µm, 1.0-1.25 µm, 0.1-1.0 µm, 0.25-1.0 µm, 0.5-1.0 µm, 0.75-1.0 µm, 0.1-0.75 µm, 0.25-0.75 µm, 0.5-0.75 µm, 0.1-0.5 µm, 0.25-0.5 µm, or 0.1-0.25 µm. In some embodiments, the microfilter has a pore size of about 0.45 µm. In some embodiments, the microfilter has a pore size of about 1.2 µm. In some embodiments, the microfilter has a pore size, wherein at least 50%, 60%, 70%, 80%, 85%, 90%, 95%, or 98% of the virus passing through the microfilter remain intact. The intactness of the virus can be assessed by observing the virus under electron microscopy, assessing the virus titer, or any other methods known in the art. In some embodiments, the virus titer after the microfiltration is at least about 50%, 55%, 60%, 65%, 70%, 75%, 80%, 85%, 90%, 95% or 98% of the virus titer prior to the microfiltration.

In some embodiments, the virus is not subjected to a centrifugation step prior to being subjected to the IE chromatography and/or the HA chromatography. In some embodiments, the virus is not subjected to an ultracentrifugation step prior to being subjected to the IE chromatography and/or the HA chromatography. In some embodiments, the virus is not subjected to an ultrafiltration step prior to being subjected to the IE chromatography and/or the HA chromatography. In some embodiments, the virus is not subjected to a gel filtration step prior to being subjected to the IE chromatography and/or the HA chromatography. In some embodiments, the virus is not subjected to an filtration step through a filter, wherein the filter has a pore size about or less than about 1.2 μm, 1.1 μm, 1.0 μm, 0.9 μm, 0.8 μm, 0.7 μm, 0.6 μm, 0.5 μm, 0.45 μm, 0.4 μm, 0.3 μm, 0.2 μm, 0.1 μm, 0.75 μm, 0.05 μm, 0.25 μm, or 0.01 μm. In some embodiments, the virus is not subjected to a filtration (e.g., ultrafiltration) or centrifugation (e.g., ultracentrifugation) step prior to being subjected to the IE chromatography and/or the HA chromatography, wherein at least 5%, 10%, 15%, 20%, 25%, 30%, 35%, 40%, 45%, 50%, 55%, 60%, 65%, 70%, 75%, 80% of the virus loses intactness. The intactness of the virus can be assessed by observing the virus under electron microscopy, assessing the virus titer, or any other methods known in the art. In some embodiments, the virus titer after the filtration (e.g., ultrafiltration) or centrifugation (e.g., ultracentrifugation) is about or less than about 50%, 55%, 60%, 65%, 70%, 75%, 80%, 85%, 90%, 95% or 98% of the virus titer prior to the microfiltration.

E. Virus

The virus described in this application can be any enveloped virus. In some embodiments, the virus is selected from the group consisting of rabies virus, influenza virus, Japanese encephalitis virus, measles virus, rubella virus, varicella virus, mumps virus, dengue fever virus, or human immunodeficiency virus (HIV).

In some embodiments, the strain of virus is attenuated. In some embodiments, the strain of virus is not attenuated.

In some embodiments, the virus is rabies virus. In some embodiments, the strain of the virus is CTN-1V. In some embodiments, the virus is Japanese encephalitis virus. In some embodiments, the strain of the virus is P3. In some embodiments, the virus is influenza virus. In some embodiments, the strain of the virus is H1N1.

1) Purified Virus Particles

Also provided herein are isolated viruses produced by the methods described herein. In some embodiments, the purified virus comprises one or more outer membrane proteins. In some embodiments, the one or more outer membrane proteins have a preferred copy number or a preferred range of copy number. In some embodiments, the preferred copy number or the preferred range of copy number is higher than a non-preferred copy number or range of copy number. In some embodiments, the purified virus with the preferred copy number or the preferred range of copy number of the outer membrane protein has a higher stability than the virus with a non-preferred copy number of the outer membrane protein. In some embodiments, a virus vaccine with the purified virus with the preferred copy number or the preferred range of copy number is more immunogenic than a virus vaccine with a virus with the non-preferred copy number or range of copy number on the outer membrane protein. In some embodiments, the preferred copy number is at least about or 20, 50, 100, 150, 200, 250, 300, 350, 400, 450, 500, 600, 700, 800, 900, 1000. In some embodiments, the preferred range of copy number is about 20-50, 50-100, 100-150, 150-200, 250-300, 350-400, 450-500, 500-600, 600-700, 700-800, 800-900, 900-1000, or more than 1000.

In some embodiments, the one or more than one outer membrane protein comprises a glycoprotein. In some embodiments, the glycoprotein has a preferred degree or preferred range of degree of glycosylation. In some embodiments, the preferred degree or preferred range of degree of glycosylation is higher than a non-preferred degree or range of degree of glycosylation. In some embodiments, the purified virus with a preferred degree of glycosylation on the one or more outer membrane proteins have a higher stability than the virus with a non-preferred degree of glycosylation on the one or more than one outer membrane protein. In some embodiments, a virus vaccine with the purified virus with a preferred degree of glycosylation on the one or more outer membrane proteins is more immunogenic than a virus vaccine a virus with a non-preferred degree of glycosylation on the one or more than one outer membrane protein.

In some embodiments, the one or more outer membrane proteins comprises a glycoprotein comprising oligosaccharide, wherein the weight ratio of oligosaccharide to the whole glycoprotein being about or at least about 3, 4, 5, 6, 7, 8, 9, 10, 11, or 12 percent. In some embodiments, the weight ratio of oligosaccharide to the whole glycoprotein being about 5-20, 10-18, or 12-15 percent.

In some embodiments, the one or more outer membrane proteins have a weight ratio of about or at least about 5, 10, 15, 20, 25, 30, 35, 40, 45, 50, 55, 60, 65, 70, 75, 80, 85, or 90 percent to the total viral protein. In some embodiments, the one or more outer membrane proteins have a weight ratio of about 5-10, 10-15, 15-20, 20-25, 25-30, 30-40, 40-45, 45-50, 50-55, 55-60, 60-65, 65-70, 70-75, 75-80, 80-85, or 85-90 percent to the total viral protein.

In some embodiments, the purified virus comprises a non-outer membrane protein. In some embodiments, the weight ratio of the non-outer membrane protein to the total viral protein is about or at least about 5, 10, 15, 20, 25, 30, 35, 40, 45, 50, 55, 60, 65, 70, 75, 80, 85, or 90 percent. In some embodiments, the weight ratio of the protein to the total viral protein is less than about 5, 10, 15, 20, 25, 30, 35, 40, 45, 50, 55, 60, 65, 70, 75, 80, 85, or 90 percent. In some embodiments, the weight ratio of the protein to the total viral protein is about 5-10, 10-15, 15-20, 20-25, 25-30, 30-40, 40-45, 45-50, 50-55, 55-60, 60-65, 65-70, 70-75, 75-80, 80-85, or 85-90 percent.

In some embodiments, the purified virus is rabies virus comprising an outer membrane protein G. In some embodiments, the weight ratio of protein G to the total viral protein is at least about 10, 20, 30, 40, 45 percent. In some embodiments, the weight ratio of protein G to the total viral protein is about 25-70%, 30-60%, 35-55%, or 35-48%.

In some embodiments, at least about 20%, 30%, 40%, 50%, 60%, 70%, 75%, 80%, 85%, 90%, 92% or 95% of the purified virus in the composition are intact particles. In some embodiment, the intactness of the purified virus particles can be determined by size, shape, potency (e.g., NIH test), biophysical or biochemical characteristics (e.g., glycosylation of outer membrane protein).

The intactness can be determined by observing the appearance (e.g., size or shape) of the virus particles. The particle size or shape can be analyzed by any methods known in the art, for example, by means of electron microscopy or the zetasizer Nano ZS machine (Malvern Instruments), which measures the Brownian motion of the particles on the basis of "quasielastic" light scattering (Dynamic Light scattering).

In some embodiments, the purified virus is essentially free of non-viral DNA. In some embodiments, the purified virus is essentially free of DNA from host cells. In some embodiments, the purified virus has less than less than about 100 pg, 80 pg, 60 pg, 40 pg, or 20 pg non-viral DNA or DNA from host cells per dose. In some embodiments, the purified virus has less than less than about 100 pg, 80 pg, 60 pg, 40 pg, or 20 pg non-viral DNA or DNA from host cells per dose, wherein each dose has a potency of at least 2.5 IU (NIH test). In some embodiments, the purified virus has less than less than about 100 pg, 80 pg, 60 pg, 40 pg, 20 pg, or 10 pg non-viral DNA or DNA from host cells per 50 µg. In some embodiments, the purified virus has about or less than about 1%, 0.5%, 0.3%, 0.2%, 0.1%, or 0.08% DNA from host cells.

In some embodiments, the purified virus is essentially free of non-viral protein. In some embodiments, the purified virus is essentially free of protein from host cells. In some embodiments, the purified virus comprises about or less than about 4 µg, 3 µg, 2 µg, 1 µg, 0.8 µg, 0.7 µg, 0.6 µg, or 0.5 µg non-viral protein or protein from host cells per dose. In some embodiments, the purified virus comprises about or less than about 4 µg, 3 µg, 2 µg, 1 µg, 0.8 µg, 0.7 µg, 0.6 µg, or 0.5 µg non-viral protein or protein from host cells per dose, wherein each dose has a potency of at least 2.5 IU (NIH test). In some embodiments, the purified virus comprises about or less than about 4 µg, 3 µg, 2 µg, 1 µg, 0.8 µg, 0.7 µg, 0.6 µg, or 0.5 µg non-viral protein or protein from host cells per 50 µg. In some embodiments, the purified virus has about or less than about 50%, 35%, 20%, 10%, 8%, 5%, 4%, or 3% proteins from host cells.

In some embodiments, the purified virus is essentially free of a serum albumin. In some embodiments, the serum albumin is of animal origin. In some embodiments, the serum albumin is of human origin. In some embodiments, the serum albumin is of bovine origin. In some embodiments, the serum albumin is fetal bovine serum albumin. In some embodiments, the serum albumin is calf serum albumin. In some embodiments, the purified virus comprises about or less than about 50 ng, 40 ng, 30 ng, 20 ng, 10 ng, 8 ng, 6 ng, 5 ng, 4 ng, 3 ng, 2 ng, or 1 ng of the serum albumin per dose. In some embodiments, the serum albumin is calf serum albumin. In some embodiments, the purified virus comprises about or less than about 50 ng, 40 ng, 30 ng, 20 ng, 10 ng, 8 ng, 6 ng, 5 ng, 4 ng, 3 ng, 2 ng, or 1 ng of the serum albumin in each dose, wherein each dose has a potency of at least 2.5 IU (NIH test). In some embodiments, the purified virus comprises about or less than about 50 ng, 40 ng, 30 ng, 20 ng, 10 ng, 8 ng, 6 ng, 5 ng, 4 ng, 3 ng, 2 ng, or 1 ng of the serum albumin per 50 µg. In some embodiments, the purified virus has about or less than about 0.1%, 0.075%, 0.05%, 0.025%, 0.01%, 0.008%, or 0.006% serum albumin.

In some embodiments, the purified virus has pH of about 7.2-8.0, 7.4-7.8, 7.5-7.7, or 7.6-7.7. In some embodiments, the purified virus has osmolality of about or 300-450, 350-400, or 370-390 mOsmol/kg.

In some embodiments, the purified virus has a potency (e.g., NIH test) of about or at least about 2.5 IU, 3 IU, 3.5 IU, 4 IU, 4.5 IU, or 5 IU per dose or per 25 µg. In some embodiments, the purified virus is in a solution, wherein the solution is clear. In some embodiments, the solution is a phosphate buffer.

In some embodiments, the purified virus is stable for or at least about 1, 2, 3, 4, 5, 6, 7, 8, 9, 10, 11, or 12 months at room temperature (e.g., at about 20-25° C.) or under a refrigerated condition (e.g., at about 2-8° C.). In some embodiments, the purified virus is stable for at least about 14, 28, 31, 35, 39, or 42 days at about 35-40° C. (e.g., 37° C.). The purified virus is stable when the composition has about or at least about 2.5 IU, 3 IU, 3.5 IU, 4 IU, 4.5 IU, or 5 IU per dose or per 25 µg after being kept for said time period under said condition or temperature. In some embodiments, the purified virus has a potency (e.g., NIH test) of about or at least about 3 IU, 3.5 IU, 4 IU, 4.5 IU, 5 IU, 5.5 IU, 6 IU, 6.6 IU, 7 IU, 7.5 IU, 8 IU, 8.5 IU per dose or per 25 µg after being kept for said time period under said condition or temperature. In some embodiments, the purified virus after being kept for longer than 3 months (e.g., about 4, 5, 6, 7, 8, 9, 10, 11, 12 months) at room temperature or under a refrigerated condition has a potency (e.g., NIH test) which is not decreased by more than about 2.5%, 5%, 10%, 15%, or 20% compared to the potency after being kept for 3 months under said condition. In some embodiments, the purified virus after being kept for more than 28 days at about 35-40° C. (e.g., 37° C.) has a potency (e.g., NIH test) which is not decreased by more than about 2.5%, 5%, 10%, 15%, or 20% compared to the potency after being kept for 28 days under said condition.

In some embodiments, the purified virus has a potency (e.g., NIH test) of about or at least about 2.5 IU, 2.6 IU, 2.7 IU, 2.8 IU, 2.9 IU, 3 IU, 3.1 IU, 3.2 IU, 3.3 IU per dose or per 25 µg under heat stability test. The stability test is carried out by keeping the composition at a high temperature (e.g., a temperature higher than room temperature, e.g., more than about 30° C., e.g., about 35-40° C., e.g., about 37° C.) for a period of time (e.g., about or at least about 14, 28, 31, 35, 39, or 42 days), and assessing the potency (e.g., NIH test) of the virus in the composition after said time period.

In some embodiments, the purities of the purified virus from two different batches of the biological samples are not different by more than 1%, 2%, 3%, 4%, 5%, 7.5%, 10%, 15%, or 20%. In some embodiments, the purity of the purified virus is the ratio of the viral protein to the total protein. In some embodiments, the purities of the purified virus from multiple batches of the biological samples are not below 80%, 85%, 90%, 92.5% or 95%.

In some embodiments, the ratios of the one or more outer membrane proteins to the total viral protein of the purified virus from two different batches of the biological samples are not different by more than 1%, 2%, 3%, 4%, 5%, 7.5%, 10%, 15%, 20%, 30%, 40%, or 50%. In some embodiments, the copy numbers of the one or more outer membrane proteins on the purified virus from two different batches of the biological samples are not different by more than 1%, 2%, 3%, 4%, 5%, 7.5%, 10%, 15%, 20%, 30%, 40%, or 50%. In some embodiments, the glycosylation degrees (e.g., the ratio of oligosaccharides to the outer membrane protein(s)) of the one or more outer membrane proteins on the purified virus from two different batches of the biological samples are not different by more than 1%, 2%, 3%, 4%, 5%, 7.5%, 10%, 15%, 20%, 30%, 40%, or 50%.

In some embodiments, the potencies (e.g., NIH test) of the purified virus from multiple batches of the biological samples are not different by more than about 1%, 2%, 3%, 4%, 5%, 7.5%, 10%, 15%, 20%, 30%, 40%, or 50% per dose or 25 μg. In some embodiments, the potencies (e.g., NIH test) of the purified virus from multiple batches of the biological samples are not different by more than about 0.5 IU, HU, 1.5 IU, 2 IU, 2.5 IU, 3 IU, 4 IU, or 5 IU per dose or 25 μg.

In some embodiments, the multiple batches comprise about or at least about 2, 3, 4, 5 batches. In some embodiments, the two or multiple different batches of biological samples are derived from inoculating same type of cells or tissues. In some embodiments, the two or multiple different batches of biological samples are derived from inoculating different type of cells or tissues. In some embodiments, the two or multiple different batches of biological samples are derived from inoculating the same cells or tissues. In some embodiments, the two or multiple different batches of biological samples are derived from inoculating the same cells or tissues.

In some embodiments, the purified virus is for preparing a vaccine.

F. Virus Harvest

In some embodiments, the biological sample is derived from a culture that harvests a virus. In some embodiments, the culture is a cell culture. In some embodiments, the culture is a tissue culture. In some embodiments, the tissue is an animal tissue. In some embodiments, the tissue is an avian tissue. In some embodiments, the tissue is a brain tissue. In some embodiments, the brain tissue is from a mouse. In some embodiments, the culture is an embryo culture. In some embodiments, the embryo is a bird embryo. In some embodiments, the embryo is a chicken embryo. In some embodiments, the embryo is a duck embryo.

In some embodiments, the culture is a culture of primary cells. In some embodiments, the culture is a culture of passaged cells. In some embodiments, the cells are animal cells. In some embodiments, the cells are human cells. In some embodiments, the cells are human diploid cells. In some embodiments, the cells are MRC-5 cells. In some embodiments, the cells are Vero cells. In some embodiments, the cells are primary hamster cells. In some embodiments, the cells are kidney cells. In some embodiments, the cells are primary hamster kidney cells. In some embodiments, the cells are dog kidney cells. In some embodiments, the cells are primary dog kidney cells. In some embodiments, the cells are fibroblasts. In some embodiments, the fibroblasts are from chicken embryo. In some embodiments, the cells are primary fibroblasts from chicken embryo.

The cell culture may be prepared either in a bioreactor or traditionally in flasks (Roux dishes, rolling flasks, Multitray™, Cell-Cube™, etc.). In some embodiments, a large-volume bioreactor (e.g., with a volume of about 500-2000 L) is used. The virus is introduced into the cell culture. In some embodiments, the amount of the introduced virus is calculated to have a 0.01-0.1 multiplicity of infection (MOI). In some embodiments, the amount of the introduced virus is calculated to have a MOI less than 0.01.

The medium used for harvesting virus can be any suitable medium. In some embodiments, the medium is MEM. In some embodiments, the medium has less than about 10 g/L, or 5 g/L proteins (e.g., human albumin).

In some embodiments, the virus is harvested in the presence of a serum. In some embodiments, the serum is not human origin. In some embodiments, the serum is animal origin. In some embodiments, the serum is a bovine serum. In some embodiments, the serum is a fetal serum or calf serum.

The period required for viral multiplication and propagation may be determined by monitoring the infectious titer. In some embodiments, the harvesting is carried out by simple removal of the viral multiplication medium which contains the viruses produced by the cells. In some embodiments, after having removed the viral multiplication medium, new medium is reintroduced into the bioreactor so as to allow a further viral multiplication leading to a further harvest. In some embodiments, at least 2, 3, 4, 5, 6, 7, or 8 successive harvests are obtained in the same bioreactor from the same cell culture. In some embodiments, the virus is harvested under a temperature of about 32° C., 33° C., 34° C., 35° C., 36° C., 37° C. or 38° C. In some embodiments, the virus is harvested under pH of about 6.5-7.8. In some embodiments, the virus is harvested under pH of about 7.0-7.5.

In some embodiments, the virus is rabies virus. In some embodiments, the strain of the virus is CTN-1V. In some embodiments the rabies virus is harvested from a medium (e.g., MEM) supplemented with fetal bovine serum or calf serum. In some embodiments, the virus is harvested under 33° C. In some embodiments, the virus is harvested under 37° C. In some embodiments, the virus is harvested under pH of about 7.0-7.5. In some embodiments, the virus is harvested under pH of about 7.2. In some embodiments, the virus is harvested from a culture of Vero cells. In some embodiments, the virus is harvested from a culture of MRC-5 cells. In some embodiments, the virus is harvested from a culture of chicken embryo.

Rabies Virus Compositions

Provided herein include rabies virus compositions produced by any of the methods described herein. In some embodiments, the virus compositions comprise a virus vaccine.

Also provided are rabies virus compositions described herein. In some embodiments, there is provided a virus composition comprising rabies virus particles, wherein at least about 80% of the total protein in the composition is viral protein, wherein the viral protein comprises: at least about 35-48% protein G. In some embodiments, the virus protein further comprises: about 28-37% protein N; about 8-12% protein P; and about 13-16% protein M. In some embodiments, the virus composition further comprises a stabilizer. In some embodiments, the stabilizer comprises sucrose and albumin. In some embodiments, pH of the composition is about 7.5-7.7. In some embodiments, the composition is white when it is solid, and wherein a solution of the composition is clear. In some embodiments, the water content of the composition is less than 3%. In some embodiments, the potency (e.g., NIH test) of the virus composition under long term stability test is at least about 4 IU/dose or 4 IU/25 μg. In some embodiments, the potency of the composition under heat stability test is at least 3 IU/dose. In some embodiments, the bovine serum albumin (BSA) content is less than about 10 ng/dose. In some embodiments, the composition is a virus vaccine composition. In some embodiments, the composition is lyophilized. In some embodiments, the virus composition is substantially free of non-viral DNA.

In some embodiments, there is provided a virus composition comprising rabies virus particles, wherein at least about 80% of the total protein in the composition is viral protein, wherein the viral protein comprises: at least about 35-48% protein G, and wherein at least about 80% of the rabies virus particles in the composition are intact viral particles. In some embodiments, the intactness of the virus particles can be determined by size, shape, potency (e.g., NIH test), biophysical or biochemical characteristics (e.g., glycosylation of outer membrane protein). In some embodiments, the virus protein further comprises: about 28-37% protein N; about 8-12% protein P; and about 13-16% protein M. In some embodiments, the virus composition further comprises a stabilizer. In some embodiments, the stabilizer comprises sucrose and albumin. In some embodiments, pH of the composition is about 7.5-7.7. In some embodiments, the composition is white when it is solid, and wherein a solution of the composition is clear. In some embodiments, the water content of the composition is less than 3%. In some embodiments, the potency (e.g., NIH test) of the virus in the composition under long term stability test is at least about 4 IU/dose or 4 IU/25 μg. In some embodiments, the potency (e.g., NIH test) of the virus in the composition under heat stability test is at least 3 IU/dose. In some embodiments, the bovine serum albumin (BSA) content is less than about 10 ng/dose. In some embodiments, the composition is a virus vaccine composition. In some embodiments, the composition is lyophilized. In some embodiments, the virus composition is substantially free of non-viral DNA.

In some embodiments, there is provided a virus composition comprising rabies virus particles, wherein at least about 80% of the total protein in the composition is viral protein, wherein the viral protein comprises: at least about 35-48% protein G, and wherein the composition is substantially free of non-viral DNA. In some embodiments, the virus protein further comprises: about 28-37% protein N; about 8-12% protein P; and about 13-16% protein M. In some embodiments, the virus composition further comprises a stabilizer. In some embodiments, the stabilizer comprises sucrose and albumin. In some embodiments, pH of the composition is about 7.5-7.7. In some embodiments, the composition is white when it is solid, and wherein a solution of the composition is clear. In some embodiments, the water content of the composition is less than 3%. In some embodiments, the potency (e.g., NIH test) of the virus in the composition under long term stability test is at least about 4 IU/dose or 4 IU/25 μg. In some embodiments, the potency (e.g., NIH test) of the virus in the composition under heat stability test is at least 3 IU/dose. In some embodiments, the bovine serum albumin (BSA) content is less than about 10 ng/dose. In some embodiments, the composition is a virus vaccine composition. In some embodiments, the composition is lyophilized.

In some embodiments, there is provided a virus composition comprising rabies virus particles, wherein at least about 80% of the total protein in the composition is viral protein, wherein the viral protein comprises: at least about 35-48% protein G, and wherein the composition has a potency (e.g., NIH test) of at least about 4 IU/dose or 4 IU/25 μg. In some embodiments, the virus protein further comprises: about 28-37% protein N; about 8-12% protein P; and about 13-16% protein M. In some embodiments, the virus composition further comprises a stabilizer. In some embodiments, the stabilizer comprises sucrose and albumin. In some embodiments, pH of the composition is about 7.5-7.7. In some embodiments, the composition is white when it is solid, and wherein a solution of the composition is clear. In some embodiments, the water content of the composition is less than 3%. In some embodiments, the potency (e.g., NIH test) of the virus in the composition under long term stability test is at least about 4 IU/dose or 4 IU/25 μg. In some embodiments, the potency (e.g., NIH test) of the virus in the composition under heat stability test is at least 3 IU/dose. In some embodiments, the bovine serum albumin (BSA) content is less than about 10 ng/dose. In some embodiments, the composition is a virus vaccine composition. In some embodiments, the composition is lyophilized. In some embodiments, the virus composition is substantially free of non-viral DNA.

In some embodiments, there is provided a virus composition comprising rabies virus particles, wherein at least about 80% of the total protein in the composition is viral protein, wherein the viral protein comprises: at least about 35-48% protein G, wherein at least about 80% of the rabies virus particles in the composition are intact viral particles, and wherein the composition has a potency (e.g., NIH test) of at least about 4 IU/dose or 4 IU/25 μg. In some embodiments, the virus protein further comprises: about 28-37% protein N; about 8-12% protein P; and about 13-16% protein M. In some embodiments, the virus composition further comprises a stabilizer. In some embodiments, the stabilizer comprises sucrose and albumin. In some embodiments, pH of the composition is about 7.5-7.7. In some embodiments, the composition is white when it is solid, and wherein a solution of the composition is clear. In some embodiments, the water content of the composition is less than 3%. In some embodiments, the potency (e.g., NIH test) of the virus in the composition under long term stability test is at least about 4 IU/dose or 4 IU/25 μg. In some embodiments, the potency (e.g., NIH test) of the virus in the composition under heat stability test is at least 3 IU/dose. In some embodiments, the bovine serum albumin (BSA) content is less than about 10 ng/dose. In some embodiments, the composition is a virus vaccine composition. In some embodiments, the composition is lyophilized. In some embodiments, the virus composition is substantially free of non-viral DNA.

In some embodiments, there is provided a virus composition comprising rabies virus particles, wherein at least about 80% of the total protein in the composition is viral protein, wherein the viral protein comprises: at least about 35-48% protein G, and wherein the composition is stable for at least about 1, 2, 3, 4, 5, 6, 7, 8, or 9 months at room temperature or under a refrigerated condition. In some embodiments, the virus protein further comprises: about 28-37% protein N; about 8-12% protein P; and about 13-16% protein M. In some embodiments, the virus composition further comprises a stabilizer. In some embodiments, the stabilizer comprises sucrose and albumin. In some embodiments, pH of the composition is about 7.5-7.7. In some embodiments, the composition is white when it is solid, and wherein a solution of the composition is clear. In some embodiments, the water content of the composition is less than 3%. In some embodiments, the potency (e.g., NIH test) of the virus in the composition under long term stability test is at least about 4 IU/dose or 4 IU/25 μg. In some embodiments, the potency (e.g., NIH test) of the virus in the composition under heat stability test is at least 3 IU/dose. In some embodiments, the bovine serum albumin (BSA) content is less than about 10 ng/dose. In some embodiments, the composition is a virus vaccine composition. In some embodiments, the composition is lyophilized. In some embodiments, the virus composition is substantially free of non-viral DNA.

In some embodiments, there is provided a virus composition comprising rabies virus particles, wherein at least about 80% of the total protein in the composition is viral protein, wherein the viral protein comprises: at least about 35-48% protein G, wherein at least about 80% of the rabies virus particles in the composition are intact viral particles, wherein at least about 80% of the rabies virus particles in the composition are intact viral particles, and wherein the composition is stable for at least about 1, 2, 3, 4, 5, 6, 7, 8, or 9 months at room temperature or under a refrigerated condition. In some embodiments, the virus protein further comprises: about 28-37% protein N; about 8-12% protein P; and about 13-16% protein M. In some embodiments, the virus composition further comprises a stabilizer. In some embodiments, the stabilizer comprises sucrose and albumin. In some embodiments, pH of the composition is about 7.5-7.7. In some embodiments, the composition is white when it is solid, and wherein a solution of the composition is clear. In some embodiments, the water content of the composition is less than 3%. In some embodiments, the potency (e.g., NIH test) of the virus in the composition under long term stability test is at least about 4 IU/dose or 4 IU/25 μg. In some embodiments, the potency (e.g., NIH test) of the virus in the composition under heat stability test is at least 3 IU/dose. In some embodiments, the bovine serum albumin (BSA) content is less than about 10 ng/dose. In some embodiments, the composition is a virus vaccine composition. In some embodiments, the composition is lyophilized. In some embodiments, the virus composition is substantially free of non-viral DNA.

In some embodiments, there is provided a virus composition comprising rabies virus particles, wherein at least about 80% of the total protein in the composition is viral protein, wherein the viral protein comprises: at least about 35-48% protein G, wherein at least about 80% of the rabies virus particles in the composition are intact viral particles, wherein the composition has a potency (e.g., NIH test) of at least about 4 IU/dose or 4 IU/25 μg, and wherein the composition is stable for at least about 1, 2, 3, 4, 5, 6, 7, 8, or 9 months at room temperature or under a refrigerated condition. In some embodiments, the virus protein further comprises: about 28-37% protein N; about 8-12% protein P; and about 13-16% protein M. In some embodiments, the virus composition further comprises a stabilizer. In some embodiments, the stabilizer comprises sucrose and albumin. In some embodiments, pH of the composition is about 7.5-7.7. In some embodiments, the composition is white when it is solid, and wherein a solution of the composition is clear. In some embodiments, the water content of the composition is less than 3%. In some embodiments, the potency (e.g., NIH test) of the virus in the composition under long term stability test is at least about 4 IU/dose or 4 IU/25 μg. In some embodiments, the potency (e.g., NIH test) of the virus in the composition under heat stability test is at least 3 IU/dose. In some embodiments, the bovine serum albumin (BSA) content is less than about 10 ng/dose. In some embodiments, the composition is a virus vaccine composition. In some embodiments, the composition is lyophilized. In some embodiments, the virus composition is substantially free of non-viral DNA.

In some embodiments, there is provided a virus composition comprising rabies virus particles, wherein at least about 80% of the total protein in the composition is viral protein, wherein the viral protein comprises: at least about 35-48% protein G, wherein at least about 80% of the rabies virus particles in the composition are intact viral particles, wherein at least about 80% of the rabies virus particles in the composition are intact viral particles, wherein the composition has a potency (e.g., NIH test) of at least about 4 IU/dose or 4 IU/25 μg, and wherein the composition is stable for at least about 1, 2, 3, 4, 5, 6, 7, 8, or 9 months at room temperature or under a refrigerated condition. In some embodiments, the virus protein further comprises: about 28-37% protein N; about 8-12% protein P; and about 13-16% protein M. In some embodiments, the virus composition further comprises a stabilizer. In some embodiments, the stabilizer comprises sucrose and albumin. In some embodiments, pH of the composition is about 7.5-7.7. In some embodiments, the composition is white when it is solid, and wherein a solution of the composition is clear. In some embodiments, the water content of the composition is less than 3%. In some embodiments, the potency (e.g., NIH test) of the virus in the composition under long term stability test is at least about 4 IU/dose or 4 IU/25 μg. In some embodiments, the potency (e.g., NIH test) of the virus in the composition under heat stability test is at least 3 IU/dose. In some embodiments, the bovine serum albumin (BSA) content is less than about 10 ng/dose. In some embodiments, the composition is a virus vaccine composition. In some embodiments, the composition is lyophilized. In some embodiments, the virus composition is substantially free of non-viral DNA.

In some embodiments, the virus composition comprises rabies virus particles, and at least about 20%, 30%, 40%, 50%, 60%, 70%, 75%, 80%, 85%, 90%, 92% or 95% of the rabies virus particles in the composition are intact particles. In some embodiment, the intactness of the virus particles can be determined by size, shape, potency (e.g., NIH test), biophysical or biochemical characteristics (e.g., glycosylation of outer membrane protein).

In some embodiments, the intactness can be determined by observing the appearance of the virus particles. The size of the rabies virus is about 75×180 nm. In some embodiments, the virus particle is intact when the size is about the size of the rabies virus (e.g., at least 70%, 75%, 80%, 85%, 90%, or 95% or at most 105%, 110%, 115%, 120%, 125%, or 130% of the size of rabies virus). The particle size can be analyzed by any methods known in the art, for example, by means of electron microscopy or the zetasizer Nano ZS machine (Malvern Instruments), which measures the Brownian motion of the particles on the basis of "quasielastic" light scattering (Dynamic Light scattering).

The rabies virus has a classic bullet shape. In some embodiments, the virus particle is intact when the shape of the virus particle is matching the shape of the rabies virus. In some embodiments, the virus particle is intact when the size of the particle is about the size of the rabies virus and the shape of the particle matches the shape of the rabies virus.

In some embodiments, the intactness of the virus particles can be determined by their immunogenicity. For example, the intactness of the virus particles can be determined comparing the potency (e.g., NIH test) of a certain amount of virus particles in the cell culture or animal to the potency of known intact virus of the same amount after infecting cells or animal.

In some embodiments, about or at least about 30%, 40%, 50%, 60%, 70%, 75%, 80%, 85%, 90%, 92% or 95% of the total protein in the composition is viral protein.

In some embodiments, the viral protein comprises about or at least about 10%, 15%, 20%, 25%, 30%, 35%, 40%, 45%, or 47% protein G. In some embodiments, the viral protein comprises about 25-70%, 30-60%, 35-55%, or 35-48% protein G.

In some embodiments, the viral protein comprises about or at least about 10%, 15%, 20%, 25% or 30% protein N. In some embodiments, the viral protein comprises about 10-50%, 20-40%, or 25-35% protein N.

In some embodiments, the viral protein comprises about or at least about 3%, 5%, 6%, 7% or 8% protein P. In some embodiments, the viral protein comprises about 3-20%, 5-15%, 7-13%, or 8-12% protein P.

In some embodiments, the viral protein comprises about or at least about 5%, 8%, 10%, 12%, or 13% protein M. In some embodiments, the viral protein comprises about 5-25%, 8-20%, 10-18% or 12-16% protein M.

In some embodiments, the protein G comprises oligosaccharide, wherein the weight ratio of oligosaccharide to the protein G is about or at least about 5, 7.5, 10, 12.5, 15, 17.5, 20, 22.5, 25, 27.5, or 30 percent. In some embodiments, the weight ratio of oligosaccharide to the protein G is about 5-40, 10-35, 20-30, or 24-30 percent.

In some embodiments, the virus composition is essentially free of non-viral DNA. In some embodiments, the virus composition is essentially free of DNA from host cells. In some embodiments, the virus composition has less than less than about 100 pg, 80 pg, 60 pg, 40 pg, or 20 pg non-viral DNA or DNA from host cells per dose, wherein each dose has a potency of at least 2.5 IU (NIH test). In some embodiments, the virus composition has less than less than about 100 pg, 80 pg, 60 pg, 40 pg, or 20 pg non-viral DNA or DNA from host cells per 50 µg.

In some embodiments, the virus composition is essentially free of non-viral protein. In some embodiments, the virus composition is essentially free of protein from host cells. In some embodiments, the virus composition comprises about or less than about 4 µg, 3 µg, 2 µg, 1 µg, 0.8 µg, 0.7 µg, 0.6 µg, or 0.5 µg non-viral protein or protein from host cells, wherein each dose has a potency of at least about 2.5 IU (NIH test). In some embodiments, the virus composition comprises about or less than about 4 µg, 3 µg, 2 µg, 1 µg, 0.8 µg, 0.7 µg, 0.6 µg, or 0.5 µg non-viral protein or protein from host cells per 50 µg.

In some embodiments, the virus composition is essentially free of a serum albumin. In some embodiments, the serum albumin is of animal origin. In some embodiments, the serum albumin is of human origin. In some embodiments, the serum albumin is of bovine origin. In some embodiments, the serum albumin is fetal bovine serum albumin. In some embodiments, the serum albumin is calf serum albumin. In some embodiments, the virus composition comprises about or less than about 50 ng, 40 ng, 30 ng, 20 ng, 10 ng, 8 ng, 6 ng, 5 ng, 4 ng, 3 ng, 2 ng, or 1 ng of the serum albumin in each dose, wherein each dose has a potency of at least about 2.5 IU (NIH test). In some embodiments, the virus composition comprises about or less than about 50 ng, 40 ng, 30 ng, 20 ng, 10 ng, 8 ng, 6 ng, 5 ng, 4 ng, 3 ng, 2 ng, or 1 ng of the serum albumin per 50 µg.

In some embodiments, the virus composition has pH of about 7.2-8.0, 7.4-7.8, 7.5-7.7, or 7.6-7.7. In some embodiments, the virus composition has a water content of about or less than about 3%, 2.9%, 2.8%, 2.7%, 2.6%, 2.5%, 2.4%, 2.3%, 2.2%, 2.1%, 1.9%, 1.8%, 1.7%, 1.6%, 1.5%. In some embodiments, the virus composition has osmolality of about or 300-450, 350-400, or 370-390 mOsmol/kg.

In some embodiments, the virus composition has a potency (e.g., NIH test) of about or at least about 2.5 IU, 3 IU, 3.5 IU, 4 IU, 4.5 IU, or 5 IU per dose or per 25 µg. In some embodiments, the virus composition is white and/or loose when it is solid. In some embodiments, the virus composition is in a solution, wherein the solution is clear. In some embodiments, the solution is a phosphate buffer.

In some embodiments, the virus composition is stable for or at least about 1, 2, 3, 4, 5, 6, 7, 8, 9, 10, 11, or 12 months at room temperature (e.g., at about 20-25° C.) or under a refrigerated condition (e.g., at about 2-8° C.). In some embodiments, the virus composition is stable for at least about 14, 28, 31, 35, 39, or 42 days at about 35-40° C. (e.g., 37° C.). The virus composition is stable when the composition has about or at least about 2.5 IU, 3 IU, 3.5 IU, 4 IU, 4.5 IU, or 5 IU per dose or per 25 µg after being kept for said time period under said condition or temperature. In some embodiments, the virus composition has a potency (e.g., NIH test) of about or at least about 3 IU, 3.5 IU, 4 IU, 4.5 IU, 5 IU, 5.5 IU, 6 IU, 6.6 IU, 7 IU, 7.5 IU, 8 IU, 8.5 IU per dose or per 25 µg after being kept for said time period under said condition or temperature. In some embodiments, the virus composition after being kept for longer than 3 months (e.g., about 4, 5, 6, 7, 8, 9, 10, 11, 12 months) at room temperature or under a refrigerated condition has a potency (e.g., NIH test) which is not decreased by more than about 2.5%, 5%, 10%, 15%, or 20% compared to the potency (e.g., NIH test) after being kept for 3 months under said condition. In some embodiments, the virus composition after being kept for more than 28 days at about 35-40° C. (e.g., 37° C.) has a potency (e.g., NIH test) which is not decreased by more than about 2.5%, 5%, 10%, 15%, or 20% compared to the potency (e.g., NIH test) after being kept for 28 days under said condition.

In some embodiments, the virus composition has a potency (e.g., NIH test) of about or at least about 2.5 IU, 2.6 IU, 2.7 IU, 2.8 IU, 2.9 IU, 3 IU, 3.1 IU, 3.2 IU, 3.3 IU per dose or per 25 µg under heat stability test. The stability test is carried out by keeping the composition at a high temperature (e.g., a temperature higher than room temperature, e.g., more than about 30° C., e.g., about 35-40° C., e.g., about 37° C.) for a period of time (e.g., about or at least about 14, 28, 31, 35, 39, or 42 days), and assessing the potency (e.g., NIH test) of the virus in the composition after said time period.

In some embodiments, the virus composition further comprises a stabilizer. In some embodiments, the stabilizer comprises sucrose and/or albumin. In some embodiments, the virus composition comprises about 0.1-10%, 0.5-5%, 1-5%, or 1-3% albumin. In some embodiments, the albumin is a human albumin. In some embodiments, the albumin is a human serum albumin. In some embodiments, the virus composition comprises about 0.1-20%, 1-10%, 3-10%, or 3-6% sucrose.

In some embodiments, the virus composition comprises a phosphate buffer. In some embodiments, the phosphate buffer has pH of about 7.0-9.0, 7.2-8.5, or 7.2-8.0.

In some embodiments, the stabilizer or the virus composition is free of gelatin, dextran, trehalose, surfactants, and/or animal-proteins.

In some embodiments, the virus composition is lyophilized. In some embodiments, the lyophilized virus composition has a potency (e.g., NIH test) of about 2.5 IU, 5 IU, 7.5 IU, or 10 IU per dose or per 25 µg. In some embodiments, the potency (e.g., NIH test) of the lyophilized virus composition is decreased by about or less than about 20%, 25%, 30%, 35%, or 40%. In some embodiments, the lyophilized virus has a water content of about or less than about 3%, 2.9%, 2.8%, 2.7%, 2.6%, 2.5%, 2.4%, 2.3%, 2.2%, 2.1%, 1.9%, 1.8%, 1.7%, 1.6%, 1.5%.

In some embodiments, the lyophilized virus composition is stable for or at least about 1, 2, 3, 4, 5, 6, 7, 8, 9, 10, 11, or 12 months at room temperature (e.g., at about 20-25° C.) or under a refrigerated condition (e.g., at about 2-8° C.). In some embodiments, the lyophilized virus composition is stable for at least about 2, 3, 4, 5, or 6 weeks at about 37° C. The lyophilized virus composition is stable when the composition has about or at least about 2.5 IU, 3 IU, 3.5 IU, 4 IU, 4.5 IU, or 5 IU per dose or per 25 µg after being kept for said time period under said condition or temperature. In some embodiments, the lyophilized virus composition has a potency (e.g., NIH test) of about or at least about 3 IU, 3.5 IU, 4 IU, 4.5 IU, 5 IU, or 5.5 IU per dose or per 25 µg after being kept for said time period under said condition or temperature. In some embodiments, the lyophilized virus composition after being kept for 2, 3, 4, 5, 6, 7, 8, or 9 months at room temperature or under a refrigerated condition has a potency (e.g., NIH test) which is not decreased by more than about 5%, 7.5%, 10%, 12.5%, 15%, 17.5%, 20%, 30%, 40% or 50% compared to the lyophilized virus potency (e.g., NIH test) before being kept under said condition. In some embodiments, the lyophilized virus composition after being kept for 3, 4, 5, or 6 weeks at about 37° C. has a potency (e.g., NIH test) which is not decreased by more than about 25%, 30%, 35%, 37.5%, 40%, 45%, 50% compared to the potency (e.g., NIH test) after being kept for 28 days under said condition.

In some embodiments, the lyophilized virus composition has a potency (e.g., NIH test) of about or at least about 2.5 IU, 2.6 IU, 2.8 IU, 3 IU, 3.2 IU, 3.4 IU, 3.6 IU, 3.8 IU, 4 IU, 4.1 IU per dose or per 25 µg under heat stability test. The stability test is carried out by keeping the lyophilized composition at a high temperature (e.g., a temperature higher than room temperature, e.g., more than about 30° C., e.g., about 35-40° C., e.g., about 37° C.) for a period of time (e.g., about or at least about 2, 3, 4, 5, 6 weeks), and assessing the potency (e.g., NIH test) of the lyophilized virus composition after said time period.

In some embodiments, the lyophilized virus composition is re-dissolved in a solution in less than 60, 50, 40, 30, 20, 15, 10 seconds.

In some embodiments, the lyophilized virus composition has a water content of about or less than about 3%, 2.8%, 2.6%, 2.4%, 2.2%, 2%, 1.8%, 1.6%, or 1.5%.

Vaccine Formulation

Provided herein are methods of a vaccine formulation and vaccine formulations. The vaccine can be any vaccine and is not limited to the vaccines described herein or produced with a method described herein.

In some embodiments, the vaccine comprises inactivated virus. In some embodiments, the vaccine comprises inactivated whole virus. Inactivated whole virus vaccines are often administered subcutaneously or intramuscularly because such administrations can recruit immune cells, especially antigen presenting cells (APCs) and related cytokines to the local area to quickly induce the body to produce a protective immune response. Vaccine products are usually prepared in the form of solution or freeze-dried powder. Relatively speaking, freeze-dried powder can be preserved and transported more easily and conveniently, and can be preserved for a longer time period for use.

Vaccine excipients or additives used in the formulation of vaccines are indispensable ingredients in vaccine formulation. They can provide dosage forms, necessary physical, chemical, pharmacological and biological properties of vaccine. They also have a critical role in the stability and biological activity of the vaccine, its product quality, and the development of new dosage forms and/or kinds.

One to sixty-four of every 10,000 people who received a Japanese encephalitis vaccine had allergic reactions, severe systemic urticarial, facial angioedema, or respiratory distress. According to the WHO, the adverse reactions may be attributed to a stabilizer in the vaccine, gelatin. Recent studies have shown that individuals who had allergic reactions to monovalent measles, mumps and rubella vaccination had immunoglobulin E antibodies against gelatin, which is also a stabilizer in the vaccine. Therefore, a considerable proportion of adverse reactions caused by the vaccine can be due to the excipients and/or additives. Excipients or additives supplemented in the biological products were no longer seen as inactive substances.

Rabies vaccine formulation often contains excipients and/or additives such as gelatin, trehalose and surfactants, which may provide protection to the vaccine during lyophilization and preservation, but may also has an effect on the safety of the product.

There is provided a method of producing a vaccine formulation comprising combining the vaccine with a stabilizer. In some embodiments, the stabilizer comprises sucrose and/or albumin. In some embodiments, the vaccine formulation comprises about 0.1-10%, 0.5-5%, 1-5%, or 1-3% albumin. In some embodiments, the albumin is a human albumin. In some embodiments, the albumin is a human serum albumin. In some embodiments, the virus formulation comprises about 0.1-20%, 1-10%, 3-10%, or 3-6% sucrose.

In some embodiments, the virus formulation comprises a phosphate buffer. In some embodiments, the phosphate buffer has pH of about 7.0-9.0, 7.2-8.5, or 7.2-8.0.

In some embodiments, the stabilizer or the virus formulation is free or essentially free of gelatin, dextran, trehalose, surfactants, and/or animal-proteins.

In some embodiments, the method further comprises lyophilizing the vaccine formulation. In some embodiments, the lyophilized virus formulation has a potency (e.g., NIH test) of about 2.5 IU, 5 IU, 7.5 IU, or 10 IU per dose or per 25 µg. In some embodiments, the potency (e.g., NIH test) of the lyophilized virus formulation is decreased by about or less than about 20%, 25%, 30%, 35%, or 40%.

In some embodiments, the lyophilized virus formulation is stable for or at least about 1, 2, 3, 4, 5, 6, 7, 8, 9, 10, 11, or 12 months at room temperature (e.g., at about 20-25° C.) or under a refrigerated condition (e.g., at about 2-8° C.). In some embodiments, the lyophilized virus formulation is stable for at least about 2, 3, 4, 5, or 6 weeks at about 37° C. The lyophilized virus formulation is stable when the formulation has about or at least about 2.5 IU, 3 IU, 3.5 IU, 4 IU, 4.5 IU, or 5 IU per dose or per 25 μg after being kept for said time period under said condition or temperature. In some embodiments, the lyophilized virus formulation has a potency (e.g., NIH test) of about or at least about 3 IU, 3.5 IU, 4 IU, 4.5 IU, 5 IU, or 5.5 IU per dose or per 25 μg after being kept for said time period under said condition or temperature. In some embodiments, the lyophilized virus formulation after being kept for 2, 3, 4, 5, 6, 7, 8, or 9 months at room temperature or under a refrigerated condition has a potency (e.g., NIH test) which is not decreased by more than about 5%, 7.5%, 10%, 12.5%, 15%, 17.5%, 20%, 30%, 40% or 50% compared to the lyophilized virus potency (e.g., NIH test) before being kept under said condition. In some embodiments, the lyophilized virus formulation after being kept for 3, 4, 5, or 6 weeks at about 37° C. has a virus potency (e.g., NIH test) which is not decreased by more than about 25%, 30%, 35%, 37.5%, 40%, 45%, 50% compared to the virus potency (e.g., NIH test) after being kept for 28 days under said condition.

In some embodiments, the lyophilized virus formulation has a potency (e.g., NIH test) of about or at least about 2.5 IU, 2.6 IU, 2.8 IU, 3 IU, 3.2 IU, 3.4 IU, 3.6 IU, 3.8 IU, 4 IU, 4.1 IU per dose or per 25 μg under heat stability test. The stability test is carried out by keeping the lyophilized formulation at a high temperature (e.g., a temperature higher than room temperature, e.g., more than about 30° C., e.g., about 35-40° C., e.g., about 37° C.) for a period of time (e.g., about or at least about 2, 3, 4, 5, 6 weeks), and assessing the potency (e.g., NIH test) of the lyophilized virus formulation after said time period.

In some embodiments, the lyophilized virus formulation has a water content of about or less than about 5%, 4%, 3%, 2%, or 1.5%.

Methods of Assessing Suitability and Releasing Vaccine Compositions

Provided herein are methods of assessing suitability of an enveloped virus vaccine composition comprising virus particles for clinical use and methods of releasing a commercial batch of an enveloped virus vaccine composition comprising virus particles for clinical use. In some embodiments, the methods comprise determining the percentage of viral proteins out of the total protein in the composition and/or determining the relative percentage of one or more outer membrane proteins in the viral proteins. In some embodiments, the methods comprise determining the percentage of intact virus in the vaccine composition. The methods of assessing the intactness include methods described herein and any methods known in the art.

In some embodiments, the virus composition is suitable for clinical use if the percentage of viral proteins out of the total protein in the composition is about or at least about 75%, 80%, 85%, 90%, 92.5%, or 95%. In some embodiments, the virus composition is suitable for clinical use if the relative percentage of one or more outer membrane proteins in the viral proteins is about or at least about 5%, 10%, 15%, 20%, 25%, 30%, 35%, 40%, 45%, 50%, 55%, 60%, 65%, 70%, 75%, or 80% or 5-10%, 10-15%, 15-20%, 20-25%, 25-30%, 30-35%, 35-40%, 40-45%, 45-50%, 50-55%, 55-60%, 60-65%, 65-70%, 70-75%, or 75-80%. In some embodiments, the virus composition is suitable for clinical use if at least about 50%, 55%, 60%, 65%, 70%, 75%, 80%, 85%, 90%, or 95% of the virus particles in the composition is intact virus.

In some embodiments, the percentage of the viral proteins out of the total proteins in the composition is determined by SDS-PAGE. In some embodiments, the relative percentage of the one or more outer membrane proteins in the viral proteins is determined by HPLC. In some embodiments, the intactness of the virus particles is determined by electron microscopy.

A. Rabies Virus

Provided herein are methods of assessing suitability of a virus vaccine composition comprising rabies virus particles for clinical use and methods of releasing a commercial batch of a virus vaccine composition comprising rabies virus particles for clinical use. In some embodiments, the methods comprise a) determining the percentage of viral proteins out of the total protein in the composition and b) determining the relative percentage of protein G in the viral protein. In some embodiments, the methods further comprise determining the relative percentages of protein N, P, and/or M in the viral protein.

In some embodiments, the composition is suitable for clinical use if 1) at least about 75%, 80%, 85%, 90%, 92.5%, or 95% of the total protein in the total composition is viral protein; and/or 2) the viral protein comprises about or at least about 10%, 15%, 20%, 25%, 30%, 35%, 40%, 45%, 50%, 55%, 60%, 65%, or 70% or 10-15%, 15-20%, 20-25%, 25-30%, 30-35%, 35-40%, 40-45%, 45-50%, 50-55%, 55-60%, 60-65%, or 65-70% protein G. In some embodiments, the composition is suitable for clinical use if 1) at least about 80% of the total protein in the total composition is viral protein; and/or 2) the viral protein comprises about or at least about 25-70%, 30-60%, 35-55%, or 35-48% protein G.

In some embodiments, the batch of the virus composition can be released or is released if 1) at least about 75%, 80%, 85%, 90%, 92.5%, or 95% of the total protein in the total composition is viral protein; and/or 2) the viral protein comprises about or at least about 10%, 15%, 20%, 25%, 30%, 35%, 40%, 45%, 50%, 55%, 60%, 65%, or 70% or 5-10%, 10-15%, 15-20%, 20-25%, 25-30%, 30-35%, 35-40%, 40-45%, 45-50%, 50-55%, 55-60%, 60-65%, or 65-70% protein G. In some embodiments, the composition is suitable for clinical use if 1) at least about 80% of the total protein in the total composition is viral protein; and/or 2) the viral protein comprises about or at least about 25-70%, 30-60%, 35-55%, or 35-48% protein G.

In some embodiments, the viral protein in the composition further comprises: about, at least about 10%, 15%, 20%, 25% or 30% or 10-50%, 20-40%, or 25-35% protein N; and/or, at least about 3%, 5%, 6%, 7% or 8% or 3-20%, 5-15%, 7-13%, or 8-12% protein P; and/or, at least about 5%, 8%, 10%, 12%, or 13%, or 5-25%, 8-20%, 10-18% or 12-16% protein M.

The percentage of the viral proteins out of the total proteins in the composition can be determined by SDS-PAGE. In some embodiments, the relative percentage of the one or more outer membrane proteins in the viral proteins is determined by HPLC. In some embodiments, the intactness of the virus particles is determined by electron microscopy.

EXEMPLARY EMBODIMENTS

Embodiment 1. A method of purifying an enveloped virus from a biological sample, comprising subjecting the biological sample to an ion exchange ("IE") chromatography and a hydroxyapatite ("HA") chromatography.

Embodiment 2. The method of embodiment 1, wherein the hydroxyapatite chromatography is carried out after the ion exchange chromatography.

Embodiment 3. The method of embodiment 1, wherein the ion exchange chromatography is carried out after the hydroxyapatite chromatography.

Embodiment 4. The method of any one of embodiments 1-3, wherein the IE chromatography comprises:
   a) an optional IE pre-equilibration step, comprising pre-equilibrating an ion exchange column with an ion exchange pre-equilibrating buffer;
   b) an IE loading step, comprising loading the biological sample or a post-HA chromatography sample to the ion exchange column;
   c) an optionally IE equilibration step, comprising equilibrating the ion exchange column with an IE equilibrating buffer;
   d) an optional IE pre-elution step, comprising pre-eluting the ion exchange column with an IE pre-eluting buffer; and e) an IE elution step, comprising eluting the IE column with an IE elution buffer.

Embodiment 5. The method of embodiment 4, further comprising a second IE elution step comprising eluting the IE column with a second IE elution buffer.

Embodiment 6. The method of embodiment 5, wherein a first IE eluate and a second IE eluate are collected from the first IE elution step and the second IE elution step, respectively, and wherein the first IE eluate and the second IE eluate comprise virus with different structure, purity or virus protein composition.

Embodiment 7. The method of any one of embodiments 1-6, wherein the HA chromatography comprises:
- a) an optional HA pre-equilibration step, comprising pre-equilibrating an HA column with an HA pre-equilibrating buffer;
- b) an HA loading step, comprising loading the biological sample or a post-IE chromatography sample to the HA column;
- c) an optionally HA equilibration step, comprising equilibrating the HA column with an HA equilibrating buffer;
- d) an optional HA pre-elution step, comprising pre-eluting the HA column with an HA pre-eluting buffer; and
- e) an HA elution step, comprising eluting the HA column with an HA elution buffer.

Embodiment 8. The method of embodiment 7, further comprising a second HA elution step comprising eluting the HA column with a second HA elution buffer.

Embodiment 9. The method of embodiment 8, wherein a first HA eluate and a second HA eluate are collected from the first HA elution step and the second HA elution step, respectively, and wherein the first HA eluate and the second HA eluate comprise virus with different structure, purity or virus protein composition.

Embodiment 10. The method of any one of embodiments 1-9, wherein there is no intervening chromatography between the IE and the HA.

Embodiment 11. The method of embodiment 10, wherein there is no intervening step between the IE and the HA.

Embodiment 12. The method of any one of embodiments 1-11, wherein the IE chromatography is anion exchange chromatography.

Embodiment 13. The method of embodiment 12, wherein the anion exchange chromatography is Capto-DEAE chromatography.

Embodiment 14. The method of embodiment 12 or embodiment 13, wherein the method comprises an IE pre-equilibrating step, and wherein the IE pre-equilibrating buffer has pH of about 7.0 to about 9.5.

Embodiment 15. The method of embodiment 14, wherein the IE pre-equilibrating buffer is a phosphate buffer.

Embodiment 16. The method of any of embodiments 12-15, wherein the method comprises an IE equilibrating step, and wherein the IE equilibrating buffer has pH of about 7.0 to about 9.5.

Embodiment 17. The method of embodiment 16, wherein the IE equilibrating buffer is a phosphate buffer.

Embodiment 18. The method of any one of embodiments 12-17, wherein the method comprises an IE pre-elution step, and wherein the IE pre-elution buffer has pH of about 7.0 to about 9.5.

Embodiment 19. The method of embodiment 18, wherein the IE pre-elution buffer is a phosphate buffer.

Embodiment 20. The method of embodiment 18 or 19, wherein the IE pre-elution buffer further comprises sodium chloride.

Embodiment 21. The method of any one of embodiments 12-20, wherein the method comprises an IE elution step, and wherein the IE elution buffer has pH of about 7.0 to about 9.5.

Embodiment 22. The method of embodiment 21, wherein the IE elution buffer is a phosphate buffer.

Embodiment 23. The method of embodiment 21 or 22, wherein the IE elution buffer further comprises sodium chloride.

Embodiment 24. The method of any one of embodiments 1-23, wherein the hydroxyapatite chromatography is CHT chromatography.

Embodiment 25. The method of embodiment 24, wherein the method comprises an HA pre-equilibrating step, and wherein the HA pre-equilibrating buffer has pH of about 7.0 to about 9.5.

Embodiment 26. The method of embodiment 25, wherein the HA pre-equilibrating buffer is a phosphate buffer.

Embodiment 27. The method of any of embodiments 24-26, wherein the method comprises an HA equilibrating step, and wherein the HA equilibrating buffer has pH of about 7.0 to about 9.5.

Embodiment 28. The method of embodiment 27, wherein the HA equilibrating buffer is a phosphate buffer.

Embodiment 29. The method of any one of embodiments 24-29, wherein the method comprises an HA pre-elution step, and wherein the HA pre-elution buffer has pH of about 7.0 to about 9.5.

Embodiment 30. The method of embodiment 29, wherein the HA pre-elution buffer is a phosphate buffer.

Embodiment 31. The method of any one of embodiments 24-30, wherein the method comprises an HA elution step, and wherein the HA elution buffer has pH of about 7.0 to about 9.5.

Embodiment 32. The method of embodiment 31, wherein the HA elution buffer is a phosphate buffer.

Embodiment 33. The method of any one of embodiments 1-32, further comprising a virus inactivation step.

Embodiment 34. The method of embodiment 33, wherein the virus inactivation step is carried out prior to the IE chromatography, the HA chromatography, or both.

Embodiment 35. The method of embodiment 33, wherein the virus inactivation step is carried out after the IE chromatography, the HA chromatography, or both.

Embodiment 36. The method of any one of embodiments 33-35, wherein the inactivation step comprises inactivating the virus with an inactivating agent.

Embodiment 37. The method of any one of embodiments 1-36, wherein the biological sample is subjected to a clarification step prior to being loaded to the IE or HA column.

Embodiment 38. The method of embodiment 37, wherein the clarification step comprise microfiltration through a microfilter having pore size of 0.1-0.5 μm.

Embodiment 39. The method of any one of embodiments 1-38, wherein the biological sample is not subjected to centrifugation or ultrafiltration prior to being loaded to the IE or HA column.

Embodiment 40. The method of any one of embodiments 1-39, wherein the biological sample is a virus harvest sample.

Embodiment 41. The method of embodiment 40, wherein the virus harvest sample is derived from a culture of animal tissue, avian tissue, primary animal cells, or passaged cells.

Embodiment 42. The method of any one of embodiments 1-41, wherein the enveloped virus is selected from the group consisting of rabies virus, influenza virus, Japanese encephalitis virus, measles virus, rubella virus, varicella virus, mumps virus, dengue fever virus, or human immunodeficiency virus (HIV).

Embodiment 43. The method of embodiment 42, wherein the virus is rabies virus.

Embodiment 44. The method of any one of embodiments 1-43, further comprising obtaining the biological sample.

Embodiment 45. The method of embodiment 44, wherein the biological sample is obtained by harvesting a virus with animal tissue, avian tissue, primary animal cells, or passaged cells.

Embodiment 46. The method of any one of embodiments 1-45, further comprising combining the isolated virus with a stabilizer.

Embodiment 47. The method of embodiment 46, wherein the stabilizer comprises sucrose and albumin.

Embodiment 48. The method of embodiment 47, wherein the albumin is human serum albumin.

Embodiment 49. The method of embodiment 47 or 48, wherein the weight ratio of sucrose in the mixture is about 0.5-10%.

Embodiment 50. The method of any one of embodiments 47-49, wherein the weight ratio of albumin in the mixture is about 1-20%.

Embodiment 51. A composition comprising the isolated enveloped virus obtained according to any one of embodiments 1-50.

Embodiment 52. The composition of embodiment 51, wherein the composition is a virus vaccine.

Embodiment 53. A virus composition comprising rabies virus particles, wherein at least about 80% of the total protein in the composition is viral protein, wherein the viral protein comprises: at least about 35-48% protein G.

Embodiment 54. The virus composition of embodiment 53, wherein the virus protein further comprises: about 28-37% protein N; about 8-12% protein P; and about 13-16% protein M.

Embodiment 55. The virus composition of embodiment 53 or 54, wherein at least about 80% of the rabies virus particles in the composition are intact viral particles.

Embodiment 56. The virus composition of 55, wherein the intactness of the virus particles can be determined by size, shape, potency (e.g., NIH test), biophysical or biochemical characteristics (e.g., glycosylation of outer membrane protein).

Embodiment 57. The virus composition of any one of embodiment 54-56, wherein the composition is substantially free of non-viral DNA.

Embodiment 58. The virus composition of any one of embodiments 54-57, wherein the composition has a potency (e.g., NIH test) of at least about 4 IU/dose or 4 IU/25 μg.

Embodiment 59. The virus composition of any one of embodiments 54-58, wherein the composition is stable for at least about 1, 2, 3, 4, 5, 6, 7, 8, or 9 months at room temperature or under a refrigerated condition.

Embodiment 60. The virus composition of any one of embodiments 54-59, further comprising a stabilizer.

Embodiment 61. The virus composition of embodiment 60, wherein the stabilizer comprises sucrose and albumin.

Embodiment 62. The virus composition of any one of embodiments 54-61, wherein pH of the composition is about 7.5-7.7.

Embodiment 63. The virus composition of any one of embodiments 54-62, wherein the composition is white when it is solid, and wherein a solution of the composition is clear.

Embodiment 64. The virus composition of any one of embodiments 54-63, wherein the water content of the composition is less than 3%.

Embodiment 65. The virus composition of any one of embodiments 54-64, wherein the potency (e.g., NIH test) of the composition under long term stability test is at least about 4 IU/dose or 4 IU/25 μg.

Embodiment 66. The virus composition of any one of embodiments 54-65, wherein the potency (e.g., NIH test) of the composition under heat stability test is at least 3 IU/dose.

Embodiment 67. The virus composition of any one of embodiments 54-66, wherein the bovine serum albumin (BSA) content is less than about 10 ng/dose.

Embodiment 68. The virus composition of any one of embodiments 54-67, wherein the composition is a virus vaccine composition.

Embodiment 69. The virus composition of any one of embodiments 54-68, wherein the composition is lyophilized.

Embodiment 70. A commercial batch of a virus vaccine composition of embodiment 68.

Embodiment 71. A method of assessing suitability of a virus vaccine composition comprising rabies virus particles for clinical use, comprising: a) determining the percentage of viral proteins out of the total protein in the composition and b) determining the relative percentage of each of G, N, P, M in the viral proteins, wherein the composition is suitable for clinical use if i) at least about 80% of the total protein in the composition is viral protein, and ii) the viral protein comprises: about 35-48% protein G.

Embodiment 72. The method of embodiment 71, wherein the viral protein in the composition further comprises: about 28-37% protein N; about 8-12% protein P; and about 13-16% protein M.

Embodiment 73. A method of releasing a commercial batch of a virus vaccine composition comprising rabies virus particles for clinical use, comprising: a) determining the percentage of viral proteins out of the total protein in the composition; b) determining the relative percentage of each of G, N, P, M in the viral proteins, and c) releasing the commercial batch for clinical use if i) at least about 80% of the total protein in the composition is viral protein, and ii) the viral protein comprises about 35-48% protein G.

Embodiment 74. The method of embodiment 73, wherein the viral protein in the composition further comprises: about 28-37% N; about 8-12% P; and about 13-16% M.

Embodiment 75. The method of embodiment 73 or 74, wherein the percentage of the viral proteins out of the total proteins in the composition is determined by SDS-PAGE.

Embodiment 76. The method of any one of embodiments 73-75, wherein the relative percentage of each of G, N, P, M in the viral proteins is determined by HPLC.

EXAMPLES

Example 1: The Purification of Virus from Multiple Sources

In this example, the methods of isolating virus in the present application is demonstrated by applying the methods to biological samples collected from Vero cell culture (roller flask culture, square flask culture, bioreactor culture), human diploid cells culture and chicken embryos culture in which the cells were infected with the CTN-1 strain of the rabies virus.

A. Pretreatment of the Biological Samples

The collected biological samples were filtered through a microporous membrane filter with a pore size of 0.45 μm.

B. Anion Exchange ("AE") Chromatography The filtered samples were then subjected to an AE chromatography under the following conditions. A Capto-DEAE column was first pre-equilibrated with a 20 mM phosphate buffer that had pH of 7.6 and contains 150 mM NaCl. The filtered samples were then loaded to the column. After the loading, 2-5 column volumes of the 20 mM phosphate buffer that had pH of 7.6 and contains 150 mM NaCl was applied to the column for equilibrating the column. The column was then loaded with a 20 mM phosphate buffer that had pH of 7.6 and contains 200 mM NaCl to pre-elute the column. Following the pre-elution step, the column was loaded with a 20 mM phosphate buffer that had pH of 7.6 and contains 500 mM NaCl to elute the column. The eluate ("the AE eluate") was collected according to the light absorption peak(s) indicated by the chromatography detector.

C. Hydroxyapatite ("HA") Chromatography

The AE eluate collected from the AE chromatography as described above was then subjected to an HA chromatography under the following conditions. A CHT column was first pre-equilibrated with a 20 mM phosphate buffer that had pH of 7.6. The eluate A was then loaded to the column. After the loading, 2-5 column volumes of the 20 mM phosphate buffer that had pH of 7.6 were applied to the column for equilibrating the column. The column was then loaded with a 100 mM phosphate buffer that had pH of 7.6 to pre-elute the column. Following the pre-elution step, the column was loaded with a 200 mM phosphate buffer that had pH of 7.6 to elute the column. The eluate ("the HA eluate") was collected according to the light absorption peak(s) indicated by the chromatography detector.

D. Assessing the Purify and Other Parameters of the Purified Virus

After the virus were harvested from different sources including Vero cell culture (roller flask culture, square flask culture, bioreactor culture), human diploid cells culture and chicken embryos culture and purified by the AE and HA chromatography sequentially as discussed above, they were analyzed by SDS-polyacrylamide gel electrophoresis (SDS-PAGE). The gel was subject to silver or Coomassie blue staining and scanned in the gel imaging system. The peak area normalization method was used to calculate the proportion of each virus protein in the total protein. The purity of the virus was calculated by totaling the proportion of all the virus proteins. The results were shown in Table 1 and FIG. 1. Virus products harvested from different batches had comparable purity, potency and virus protein composition.

The samples at different stages of the purification process are also assessed by SDS-PAGE analysis. See FIG. 2. The results showed that each chromatography step has achieved significant purification effect.

Vero cell DNA residues in the purified virus and the potency (NIH test) were determined according to the method described in the Volume 3 of the Pharmacopoeia of the People's Republic of China published in 2015.

TABLE 1

Characteristics of purified target virus harvested from different sources

| Source | Purity (%) | Virus protein composition (G:N:P:M) | Potency (NIH test) (IU/50 ug) |
|---|---|---|---|
| Vero cell (roller flask) | 96.3 | 47.3:30.2:8.9:13.6 | 11.7 |
| Vero cell (square flask) | 95.7 | 47.2:29.6:9.4:13.8 | 10.4 |
| Vero cell (bioreactor) | 96.01 | 47.1:29.6:9.2:14.1 | 14.2 |
| Human diploid cell | 95.7 | 47.5:29.9:8.9:13.7 | 14.6 |
| Chicken embryo | 98.2 | 47.7:30.0:9.3:13.0 | 9.2 |

Example 2: The Purification of Virus Under Different Chromatography Conditions In this example, the methods of isolating virus in the present application is demonstrated by applying the methods to biological samples collected from Vero cell culture in which the cells were infected with the CTN-1 strain of the rabies virus.

A. Pretreatment of the Biological Samples

The collected biological samples were filtered through a microporous membrane filter with a pore size of 0.45 μm.

B. Anion Exchange ("AE") Chromatography

The filtered samples were then subjected to an AE chromatography under the following conditions. A Capto-DEAE column was first pre-equilibrated with a 20 mM phosphate buffer that had pH of 7.6 and contains 150 mM NaCl. The filtered samples were then loaded to the column. After the loading, 2-5 column volumes of the 20 mM phosphate buffer that had pH of 7.6 and contains 150 mM NaCl was applied to the column for equilibrating the column. The column was then loaded with a 20 mM phosphate buffer that had pH of 7.6 and contains 200 mM NaCl to pre-elute the column. Following the pre-elution step, the column was loaded with a 20 mM phosphate buffer that had pH of 7.6 and contains 500 mM NaCl to elute the column. The eluate ("the AE eluate") was collected according to the light absorption peak(s) indicated by the chromatography detector.

C. Hydroxyapatite ("HA") Chromatography

The eluate A collected from the AE chromatography as described above was then subjected to an HA chromatography under the following conditions. A CHT column was first pre-equilibrated with a 20 mM phosphate buffer that had pH of 7.6. The eluate A was then loaded to the column. After the loading, 2-5 column volumes of the 50 mM phosphate buffer that had pH of 7.6 were applied to the column for equilibrating the column. The column was then loaded with a 100 mM phosphate buffer that had pH of 7.6 to pre-elute the column. Following the pre-elution step, the column was loaded with the following three elution buffer chronologically and a different eluate was respectively collected during each step. The first elution buffer, a 100 mM phosphate buffer that had a pH of 7.6 was first applied to the column, and the eluate A ("the HA eluate A") was collected. Subsequently, the second elution buffer, a 200 mM phosphate buffer that had a pH of 7.6 was secondly applied to the column, and the eluate B ("the HA eluate B") was collected. Finally, the third elution buffer, a 300 mM phosphate buffer that had a pH of 7.6 was applied to the column, and the eluate C ("the HA eluate C") was collected.

D. Assessing the Purify and Other Parameters of the Purified Virus

The purity, protein proportions, potency (NIH test) and DNA residue from Vero cells of the virus purified as described above were assessed with methods described in Example 1D. Results were shown in Table 2 as below.

TABLE 2

Characteristics of target virus purified under different HA chromatography conditions.

| Eluate | Purity (%) | Virus protein composition (G:N:P:M) | Potency (NIH test) (IU/50 ug) | DNA residue of Vero Cell (pg/ml) |
|---|---|---|---|---|
| HA Eluate A | 86.7 | 37.1:35.5:11.8:15.6 | 4.8 | <100 |
| HA Elate B | 96.3 | 46.4:29.4:10.2:14.0 | 12.2 | <100 |
| HA Elate C | 95.9 | 45.3:29.9:10.4:14.4 | 8.8 | >500 |

Example 3: Production of Rabies Virus Vaccine Harvested from Vero Cells and Assessment of Product Quality A. Virus Harvest 2) Preparation of Vero Seed Cells Cryopreserved Vero cells were thawed in 38-40° C., and replanted into a cell culture flask with M199 cell culture media supplemented with 5% fetal bovine serum (FBS). After the cells were cultured for 72-96 hours in 37° C., the Vero cells were digested with trypsin and sub-cultured at a 1:4 ratio into new cell culture flasks for proliferation for five generations, or until a sufficient number of seed cells were obtained for the bioreactor large scale cell culture.

3) Bioreactor Expansion of Vero Cells

After confluence of the seed cells in the flasks, cells were trypsinized and suspended in culture media. Cell suspensions from multiple culture flasks were pooled and inoculated into a bioreactor with M199 culture media supplemented with 10% calf serum (CS). The culture condition was set as following: 37° C.; pH7.2; and 35% dissolved oxygen. The cell culture was under continuous perfusion to expel the culture broth and add fresh media.

4) Inoculation of Rabies Virus

After the cells were cultured in the bioreactor for six days, the cells were transfected with CTN-1V strain of rabies virus at 0.01-0.1 multiplicity of infection (MOI). After transfection, the virus was harvested under a condition of 33° C.; pH 7.6; and 35% dissolved oxygen concentration. Virus solutions were collected and fresh maintenance solution was added under continuous perfusion.

5) Production of a Virus Sample

Collected virus solutions were pooled to make a batch of virus sample for further use.

B. Assessment of the Virus Sample

The virus sample harvested from Vero cells were assessed for the virus titer, antigen content under ELISA, sterility, and existence of *mycoplasma*. The results were shown in Table 3 as below.

TABLE 3

Test results for virus sample (virus harvested from Vero cells in bioreactor).

| Test | Result |
|---|---|
| Virus titer (lgLD$_{50}$/ml) | 7.02 |
| antigen content (ELISA) (EU/ml) | 6.0 |
| Sterility Test | Sterile |
| Mycoplasma Test | In compliance. |

C. Virus Purification

1) Pretreatment of the Virus Sample

The virus samples harvested from Vero cells as described above were subjected to a filtration clarification to remove exfoliated cells and cell debris prior to the purification.

2) Anion Exchange ("AE") Chromatography

The filtered virus samples were then subjected to an AE chromatography under the following conditions. A Capto-DEAE column was first pre-equilibrated with a 20 mM phosphate buffer that had pH of 7.6 and contains 150 mM NaCl. About 20 column volumes of the filtered samples were then loaded to the column. After the loading, 2-5 column volumes of the 20 mM phosphate buffer that had pH of 7.6 and contains 150 mM NaCl was applied to the column for equilibrating the column. The column was then loaded with a 20 mM phosphate buffer that had pH of 7.6 and contains 250 mM NaCl to pre-elute the column. Following the pre-elution step, the column was loaded with a 20 mM phosphate buffer that had pH of 7.6 and contains 550 mM NaCl to elute the column. The eluate ("the AE eluate") was collected according to the light absorption peak(s) indicated by the chromatography detector.

3) Hydroxyapatite ("HA") Chromatography

The AE eluate collected from the AE chromatography as described above was then subjected to an HA chromatography under the following conditions. A CHT column was first pre-equilibrated with a 20 mM phosphate buffer that had pH of 7.6. The eluate A was then loaded to the column. After the loading, 2-5 column volumes of the 20 mM phosphate buffer that had pH of 7.6 were applied to the column for equilibrating the column. The column was then loaded with a 100 mM phosphate buffer that had pH of 7.6 and 150 mM NaCl to pre-elute the column. Following the pre-elution step, the column was loaded with a 200 mM phosphate buffer that had pH of 7.6 and 150 mM NaCl to elute the column. The eluate ("the HA eluate") was collected according to the light absorption peak(s) indicated by the chromatography detector.

D. Virus Inactivation

The HA eluate obtained according to the method described above was added β-propiolactone at a final concentration of 1/4000 to inactivate the virus at 2-8° C. for 24 hours. The mixture was then moved to 37° C. water for two hours to hydrolyze β-propiolactone.

E. Desalination and Preparation of Vaccine Stock Solution

The HA eluate was then desalted using a S-200 gel filtration column chromatography. Following chromatography, a vaccine stock solution was prepared using a 20 mM phosphate buffer that had pH of 7.6 and 50 mM NaCl.

F. Assessment of Vaccine Stock Solution

The vaccine stock solution was tested for Virus protein content, protein and DNA residues of Vero cells in two methods.

1) ELISA

To assess the content of the active ingredient in the vaccine stock solution, a commercial ELISA kit named "virus antigen relative content kit to detect virus antigen in rabies virus vaccine for human" was used to assess the content of the enzyme-labeled antigen(s).

2) Protein Content Text

The protein content of the vaccine stock solution (unit: µg/ml) was assessed and the results were relied upon to calibrate active ingredient content and prepare the final vaccine formulations and packaging. The assessment of the protein content of the vaccine stock solution was carried out according to the method described in the "Pharmacopoeia of the People's Republic of China" (2015), Volume III (General Rules 0731, the "Lorry Rule").

3) Other Quality Tests

Other relevant methods for assessing the quality of the vaccine were used. For example, the product testing procedures or methods described in the Section of "freeze-dried human rabies vaccine (Vero cells)" the General Principles of Pharmacopoeia were also applied here.

4) Results

The results were obtained using the methods described above for the vaccine stock solution. The results were compared with the harvested virus sample prior to the purification to calculate the effectiveness of the purification processes to remove the impurities. See Table 4. Additionally, the concentration of bovine serum albumin (BSA) in the vaccine stock solution was also measured and the result showed a concentration of 6.98 ng/ml. The results show that the vaccine stock solution had a low content of the impurity. For example, the total protein content and the protein residues from Vero cells were significantly lower than the prescribed national pharmacopoeia standards. See Table 5.

TABLE 4

Test results for vaccine stock solution (virus harvested from Vero cells)

| Assessment and analysis | | Virus sample | Vaccine stock solution |
|---|---|---|---|
| Total amount (ml) | | 15000 | 330 |
| Host cell DNA | Content (pg/ml) | $4 \sim 8 \times 10^5$ | <100 |
| | Removal rate (%) | | >99.99 |
| Host cell protein | Content (μg/ml) | 12.72 | 3.66 |
| | Removal rate (%) | | 99.38 |
| Total protein | Content (μg/ml) | 2844.71 | 121.43 |
| | Removal rate (%) | | 99.91 |

TABLE 5

Test results of vaccine stock solution compared to the standard

| | Vaccine stock solution | Standard[1] |
|---|---|---|
| Host cell DNA residue | <100 pg/dose | ≤100 pg/dose |
| Host cell protein residue | 0.46 μg/dose | ≤4 μg/dose |
| Total protein | 20 μg/dose | ≤80 μg/dose |
| Antigen purity | ☐95% | See footnote[2] |

[1] National Pharmacopoeia Standard
[2] No quantitative purity standard is available. The current standard recommends qualitative analysis of impurities according to test results.

Figure 3:
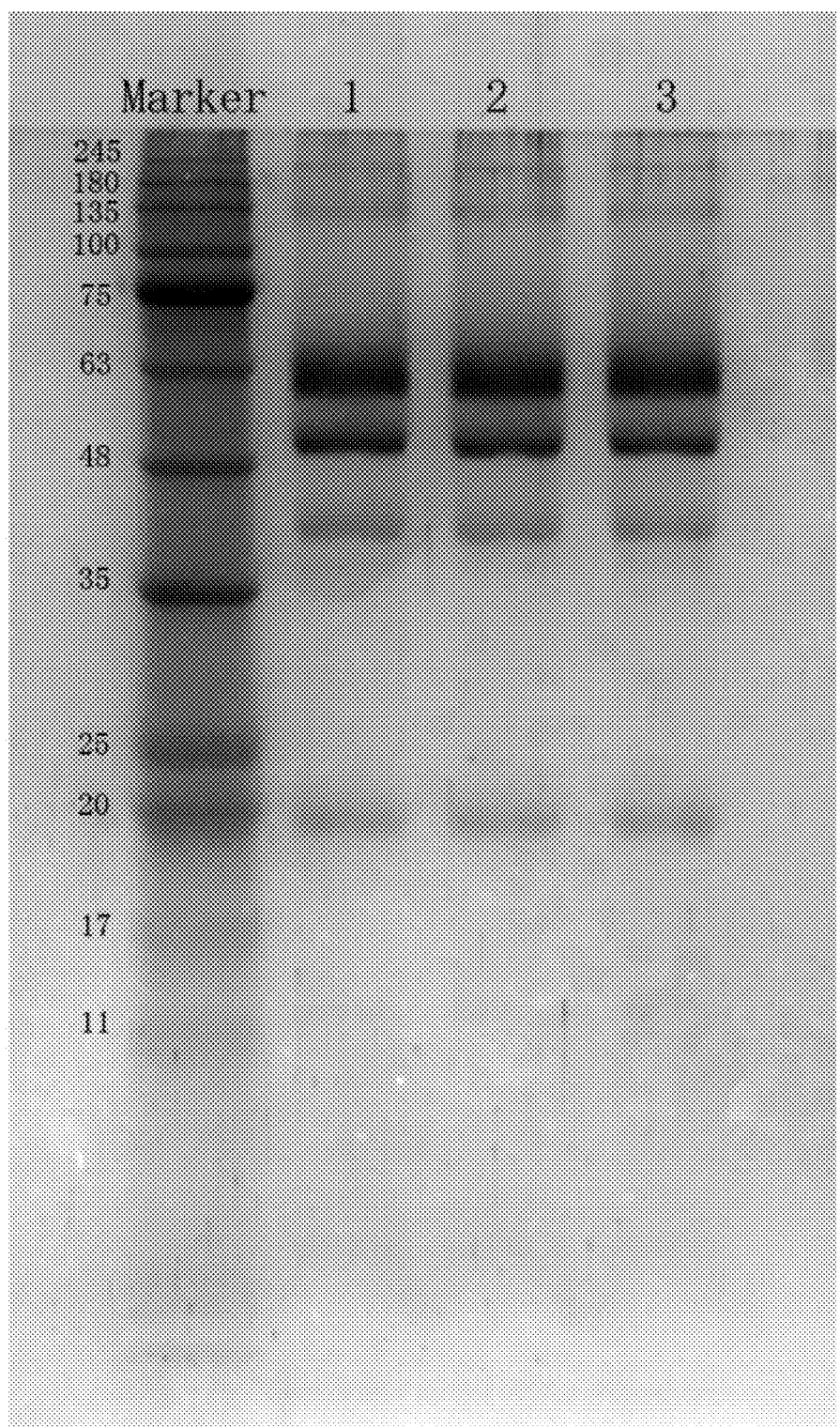
FIG. 3 shows the results of SDS-page electrophoresis of the virus stock solutions in three repeated experiments as described in Example 3 (rabies virus harvested from Vero cells). Marker represents the reference sample that indicates molecular weight standard of proteins. The molecular weight of each band of the reference sample was marked in the left. Bands 1-3 represent the three independent tests of the virus stock solutions.
Figure 4:
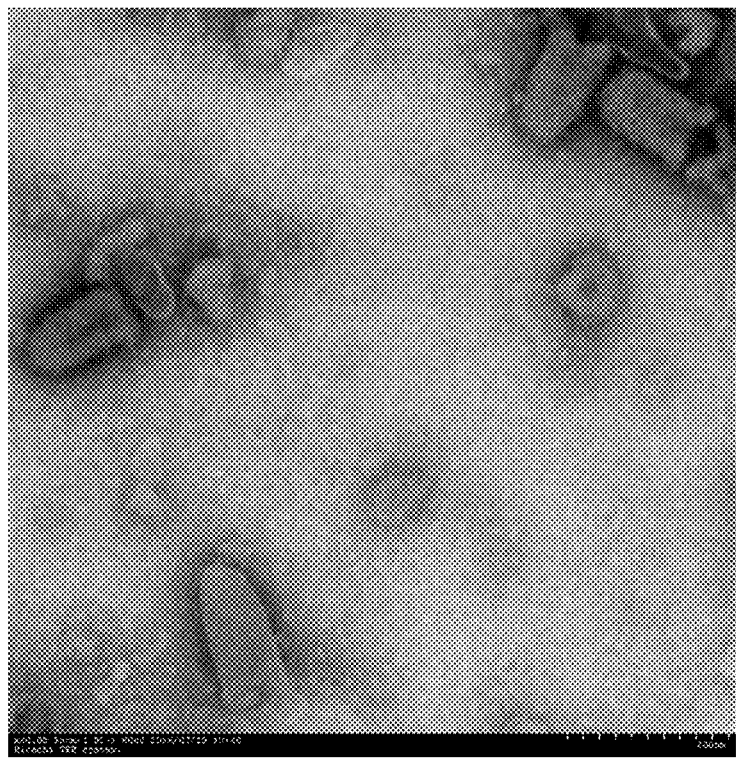
FIG. 4 shows a representative electron microscopy picture of the rabies virus in the virus stock solution as described in Example 3.

Samples of the vaccine stock solution were analyzed three times by SDS-polyacrylamide gel electrophoresis (SDS-PAGE). The gels were subject to silver staining to assess the virus antigen purity. Results were shown in Table 6. A representative picture of the SDS-page electrophoresis analysis was shown in FIG. 3. These results show that the virus antigen purity was higher than 95% in all three individual tests. Samples of the vaccine stock solution were also analyzed under electron microscopy. As shown in FIG. 4, the virus particles had intact structure and typical bullet-shaped rabies virus morphology.

TABLE 6

Analysis of virus antigen purity in vaccine stock solution (virus harvested from Vero cells).

| Test # | Antigen purity (%) |
|---|---|
| 1 | 95.501 |
| 2 | 95.731 |

TABLE 6-continued

Analysis of virus antigen purity in vaccine stock solution (virus harvested from Vero cells).

| Test # | Antigen purity (%) |
|---|---|
| 3 | 95.889 |
| Average | 95.71 |

G. Preparation of Vaccine Formulation and Packaging

According to the results of the total protein content, the vaccine stock solution was formulated to make a final solution that have a final total protein concentration of 40 μg/ml. 1% of human serum albumin and 5% of the sucrose were added as excipient/stabilizer to stabilize the vaccine formulation.

The final solution was packaged into 2 ml glass tubes with a volume of 0.5 ml per tube. The vaccine was lyophilized in a freeze dryer, and immediately closed with rubber plug and sealed with aluminum-plastic lid.

H. Quality Test of the Vaccine Product

The "freeze-dried human rabies vaccine (Vero cells)" product testing procedures and methods described in the General Principles in the "Pharmacopoeia of the People's Republic of China" in 2015 Volume III were used to assess the quality of the vaccine product. The results were compared to the Standard illustrated in the current version of the National Pharmacopoeia. See Table 7. It showed that the each quality indicator of the product met or exceeded the national pharmacopoeia standards.

TABLE 7

Quality assessment of the vaccine product (virus harvested from Vero cells)

| Test | Standard | Result |
|---|---|---|
| Identification (e.g., ELISA) | contains virus antigen | In compliance |
| Appearance | White and loose in solid form. Clear solution after dissolved. No precipitation. | In compliance |
| Osmolality (mOsmol/kg) | In compliance with criteria | 376 |
| pH | 7.2 ~ 8.0 | 7.63 |
| Water content (%) | ≤3% | 2.43 |
| Potency (IU/dose) | ≥2.5 | 5.4 |
| Heat stability (IU/dose) | ≥2.5 | 3.0 |
| Bovine serum protein residue (ng/dose) | ≤50 | 2.95 |
| Vero cell DNA residue (pg/dose) | ≤100 | ≤100 |
| Vero cell protein residue (μg/dose) | ≤4 | 0.46 |
| Sterility | In compliance with criteria | In compliance |
| Uncommon toxicity | In compliance with criteria | In compliance |
| Bacterial endotoxin (EU/dose) | ≤25 | ≤12.5 |

I. Stability Assessment

1) Real-Time Stability (Long-Term Stability) Assessment

The vaccine product was stored at 2-8° C. for long-term storage. Samples of the vaccine product was tested at 3 months, 6 months, 9 months, 1 year, 2 years and 3 years after placement to measure NIH potency. The 1-year stability study has been completed and the NIH potency test results at each time point are shown in Table 8. The results showed that the vaccine product was stable.

TABLE 8

Vaccine product long-term stability test results

| Time point | 3 months | 6 months | 9 months | 12 months |
|---|---|---|---|---|
| Potency (NIH test, IU/dose) | 5.9 | 8.1 | 6.5 | 6.7 |

2) Heat Stability Assessment

The vaccine product was stored in a 37° C. incubator and samples were taken for testing potency using NIH test at 28, 35 and 42 days after placement. The test results of NIH potency at each time point are shown in Table 9. The results showed that, after 42 days of treatment at 37° C., the vaccine product remained stable enough to meet the standard of the National Pharmacopoeia. Therefore, the heat stability of the product at 37° C. exceeds the required stability of 28 days set by the National Pharmacopoeia.

J. Homogeneity Among Different Batches

According to the same processes and/or methods described in this Example, nine batches of the virus vaccine products were continuously produced. The purity of virus antigen(s) was tested in samples of each batch. Table 10 shows that the different batches of products have consistently high purity (>95%) of virus antigen, suggesting a high homogeneity among the products.

TABLE 10

Virus antigen purity analysis among nine batches continuously produced (virus harvest from Vero cells)

| Batch no. of vaccine stock solution | Antigen purity (%) |
|---|---|
| B20150801 | 96.52 |
| B20150802 | 96.28 |
| B20150901 | 96.00 |
| B20151001 | 95.78 |
| B20151002 | 95.71 |
| B20151201 | 95.60 |
| B20151202 | 96.01 |
| B20160201 | 95.71 |
| B20160202 | 95.94 |

Example 4: Production of Rabies Virus Vaccine Harvested from Human Diploid Cells (MRC-5 Cells) and Assessment of Product Quality A. Virus Harvest 1) MRC-5 Cell Expansion:

One tube of cryopreserved MRC-5 cells was thawed in a water bath at 38-40° C. The cell suspension was transferred to a cell culture flask and cultured with MEM media supplemented with 5% fetal bovine serum for 72-96 hours at 37° C. Cells were then trypsinized and passaged into new cell culture flasks at a ratio of 1:2 for 6 generations. At least 8 flasks (TC-175 flasks) of MRC cells were prepared.

2) Virus Inoculation

After the TC-175 flask bottoms were covered by a single layer MRC-5 cells, the media was removed, and a MEM media supplemented with 0.3% human serum albumin was added. The cells were then infected with the CTN-1 strain of rabies virus at 0.01-0.1 MOI. After the virus proliferated in the incubator at 33° C. for 144 hours, the first virus sample was collected. Fresh media was added after that and the rabies virus proliferated in the incubator at the same temperature for another 94 hours. The second virus sample was collected. For each TC-175 flask, two virus samples were collected. All virus samples collected from the eight flasks (or more) were pooled as a batch of virus sample.

B. Assessment of the Virus Sample

According to the methods used in the Example 3B, the virus samples harvested from MRC-5 cells were similarly assessed. The results were shown in Table 11.

TABLE 11

Test results for virus sample (virus harvested from MRC-5 cells).

| Test | Result |
|---|---|
| Virus titer (lgLD50/ml) | 6.52 |
| antigen content (ELISA) (EU/ml) | 0.8 |
| Sterility Test | Sterile |
| Mycoplasma Test | In compliance |

C. Virus Purification

The virus was purified according to the processes and/or methods described in Example 3C. The volume of DEAE column was adjusted proportionally according to the ELISA results that indicate virus antigen contents in the sample.

D. Virus Inactivation

The purified virus was inactivated according to the processes and/or methods described in Example 3D.

E. Desalination and Preparation of Vaccine Stock Solution

After the purification and inactivation, the virus sample was further desalted and a vaccine stock solution was prepared according to the processes and/or methods described in Example 3E. The scale of the desalting column was proportionally adjusted according to the sample volume after inactivation.

F. Assessment of Vaccine Stock Solution

The protein content and virus antigen content of the vaccine stock solution were assessed according to the methods described in Example 3F. The results were compared with the virus sample before purification. See Table 12.

TABLE 12

Comparison between pre-purified virus sample and post-purified vaccine stock solution.

| Assessment and analysis | | Virus sample | Vaccine stock solution |
|---|---|---|---|
| Total amount (ml) | | 950 | 3.85 |
| antigen content (ELISA) | Content (EU/ml) | 0.8 | 36.5 |
| | Recovery rate (%) | | 18.5% |
| Total protein | Content (μg/ml) | 3440 | 152 |
| | Removal rate (%) | | 99.93% |

Figure 5:
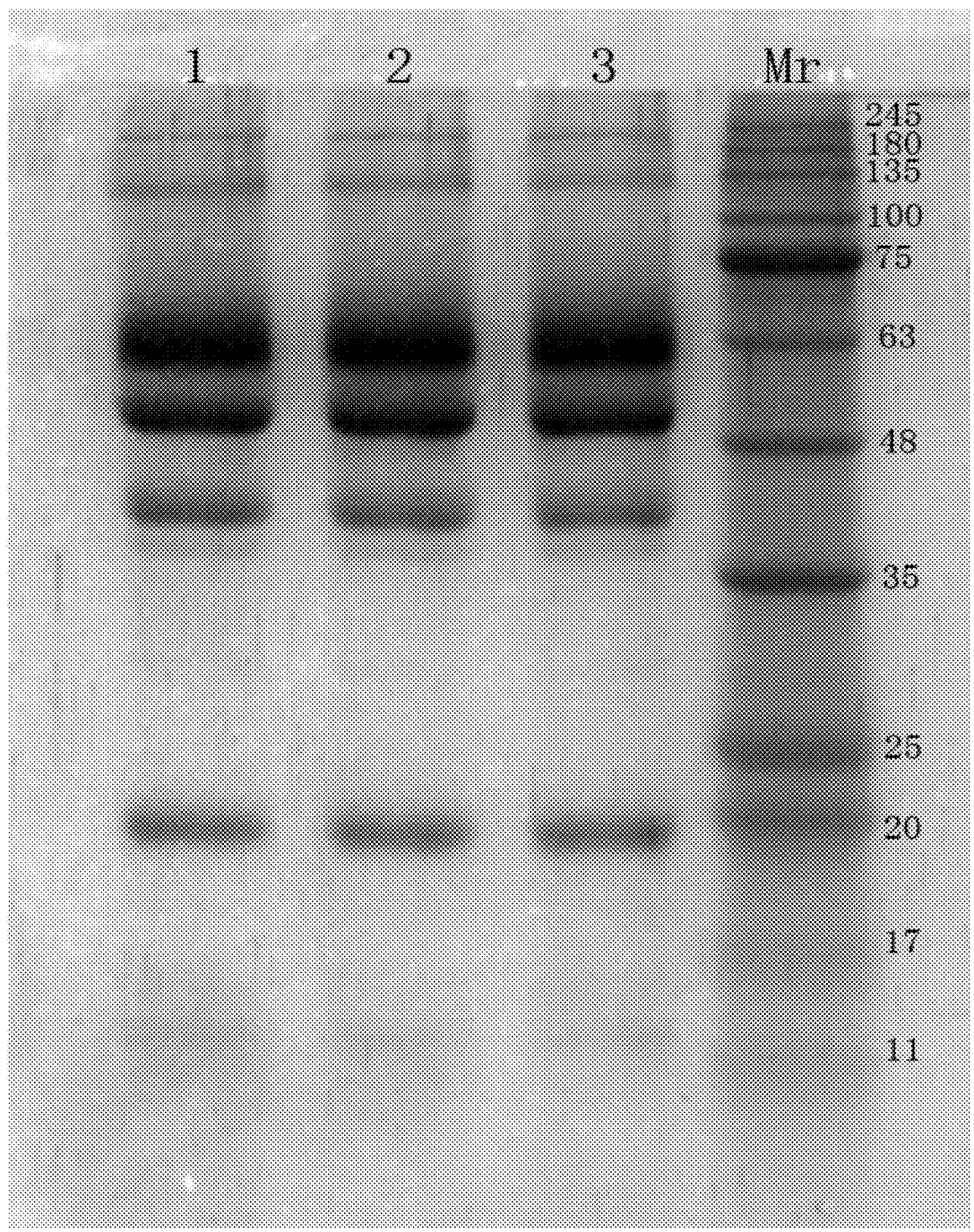
FIG. 5 shows the results of SDS-page electrophoresis of the virus stock solutions in three repeated experiments as described in Example 4 (rabies virus harvested from MRC-5 cells). Marker represents the reference sample that indicates molecular weight standard of proteins. The molecular weight of each band of the reference sample was marked in the right. Bands 1-3 represent the three independent tests of the virus stock solutions.

Samples of the vaccine stock solution were analyzed three times by SDS-polyacrylamide gel electrophoresis (SDS-PAGE). The gels were subject to silver staining to assess the virus antigen purity. Results were shown in Table 13. A representative picture of the SDS-page electrophoresis analysis was shown in FIG. 5. These results show that the virus antigen purity was higher than 95% in all three individual tests.

TABLE 13

Virus antigen purity analysis (virus harvested from human diploid cells)

| Test # | Antigen purity (%) |
|---|---|
| 1 | 95.87 |
| 2 | 96.32 |
| 3 | 95.84 |
| Average | 96.01 |

G. Preparation of Vaccine Formulation and Packaging

Vaccine formulation was prepared and packaged to final product as described in the methods and/or processes described in Example 3G.

H. Quality Test of the Final Product

Since rabies vaccine harvested from human diploid cells has not been listed in the National Pharmacopoeia, the "freeze-dried human rabies vaccine (Vero cells)" product testing procedures and methods described in the General Principles in the "Pharmacopoeia of the People's Republic of China" in 2015 Volume III were used to assess the quality of the vaccine final product. The results were shown in Table 13. According to the relevant provisions of vaccine product management in this country and abroad, the vaccine that was harvested from human diploid cells is not subject to the assessment of host cell DNA and protein residues.

TABLE 14

Quality analysis of the vaccine product (virus harvested from human diploid cells).

| Test | Standard | Result |
|---|---|---|
| Identification (e.g., ELISA) | Contains virus antigen | In |
| Appearance | White and loose in solid form. Clear solution after dissolved. No precipitation in solution. | In compliance |
| Osmolality (mOsmol/kg) | In compliance with the criteria | 381 |
| pH | 7.2~8.0 | 7.67 |
| Water content (%) | ≤3% | 2.69 |
| Potency (IU/dose) | ≥2.5 | 4.6 |
| Heat stability (IU/dose) | ≥2.5 | 3.6 |
| Bovine serum protein residue (ng/dose) | ≤50 | 3.7 |
| Sterility | In compliance with the criteria | In |
| Uncommon toxicity | In compliance with the criteria | In |
| Bacteria endotoxin (EU/dose) | ≤25 | <12.5 |

Example 5: Production of Rabies Virus Vaccine Harvested from Chicken Embryo and Assessment of the Product Quality A. Virus Harvest Five-day old SPF-grade chicken embryo was purchased, sterilized on the surface and inoculated with the CTN-1 strain of rabies virus by administering the virus into the embryo through a needle in a biological safe cabinet. The area on the embryo where the needle applied to was sealed by a sterile membrane. The embryo then was placed in a 33° C. incubator for 144 hours. After the incubation, about 2 ml chicken embryo allantoic fluid was collected. Fifty chicken embryos were inoculated with the virus, and the collected chicken embryo allantoic fluid was pooled together as the virus sample.

B. Assessment of the Virus Sample

According to the methods used in the Example 3B, the virus sample harvested from chicken embryos was similarly assessed. The results were shown in Table 15.

TABLE 15

Test results for the virus sample (virus harvested from chicken embryo).

| Test | Result |
|---|---|
| Virus titer (lgLD50/ml) | 9.02 |
| antigen content (ELISA) (EU/ml) | 28.8 |
| Sterility Test | Sterile |
| Mycoplasma Test | In compliance |

C. Virus Purification

1) Pretreatment of the Virus Sample

A virus sample of 100 ml chicken embryo allantoic fluid was harvested, collected and pooled as described above. The virus sample was added 400 ml PBS solution containing 0.1% human serum albumin. The PBS solution had pH of 7.6, 20 mM sodium phosphate and 150 mM sodium chloride. The virus sample was then filtrated through a 0.45 μm pore-sized microporous filter to remove tissue debris, exfoliated cells and cell debris.

2) Hydroxyapatite ("HA") Chromatography

The filtered virus sample was then subjected to an HA chromatography under the following conditions. A CHT column was first pre-equilibrated with a 20 mM phosphate buffer that had pH of 7.6 and 150 mM NaCl. About twenty column volumes of the virus sample were then loaded to the column. After the loading, 2-5 column volumes of the 20 mM phosphate buffer that had pH of 7.6 and 150 mM NaCl was applied to the column for equilibrating the column. The column was then loaded with a 100 mM phosphate buffer that had pH of 7.6 and 150 mM NaCl to pre-elute the column. Following the pre-elution step, the column was loaded with a 200 mM phosphate buffer that had pH of 7.6 and 150 mM NaCl to elute the column. The eluate ("the HA eluate") was collected according to the light absorption peak(s) indicated by the chromatography detector.

3) Anion Exchange ("AE") Chromatography

The HA elute were then subjected to an AE chromatography under the following conditions. A Capto-DEAE column was first pre-equilibrated with a 20 mM phosphate buffer that had pH of 7.6 and contains 150 mM NaCl. About five column volumes of the filtered samples were then loaded to the column. After the loading, 2-5 column volumes of the 20 mM phosphate buffer that has pH of 7.6 and contains 150 mM NaCl was applied to the column for equilibrating the column. The column was then loaded with a 20 mM phosphate buffer that has pH of 7.6 and contains 250 mM NaCl to pre-elute the column. Following the pre-elution step, the column was loaded with a 20 mM phosphate buffer that has pH of 7.6 and contains 550 mM NaCl to elute the column. The eluate ("the AE eluate") was collected according to the light absorption peak(s) indicated by the chromatography detector.

D. Virus Inactivation

The purified virus was inactivated according to the processes and/or methods described in Example 3D.

E. Desalination and Preparation of Vaccine Stock Solution

After the purification and inactivation, the virus sample was further desalted and a vaccine stock solution was prepared according to the processes and/or methods described in Example 3E. The scale of the desalting column was proportionally adjusted according to the sample volume after inactivation.

F. Assessment of Vaccine Stock Solution

The protein content and virus antigen content of the vaccine stock solution were assessed according to the methods described in Example 3F. The results were compared with the virus sample before purification. See Table 16.

TABLE 16

Comparison between pre-purified virus sample and post-purified vaccine stock solution (virus harvested from chicken embryo).

| Assessment and analysis | | Virus sample | Vaccine stock solution |
|---|---|---|---|
| Total amount (ml) | | 500 | 15.6 |
| Antigen content (ELISA) | Content (EU/ml) | 5.76 | 38.9 |
| | Recovery rate (%) | | 21.1% |
| Total protein | Content (µg/ml) | 1320 | 164 |
| | Removal rate (%) | | 99.61% |

Figure 6:
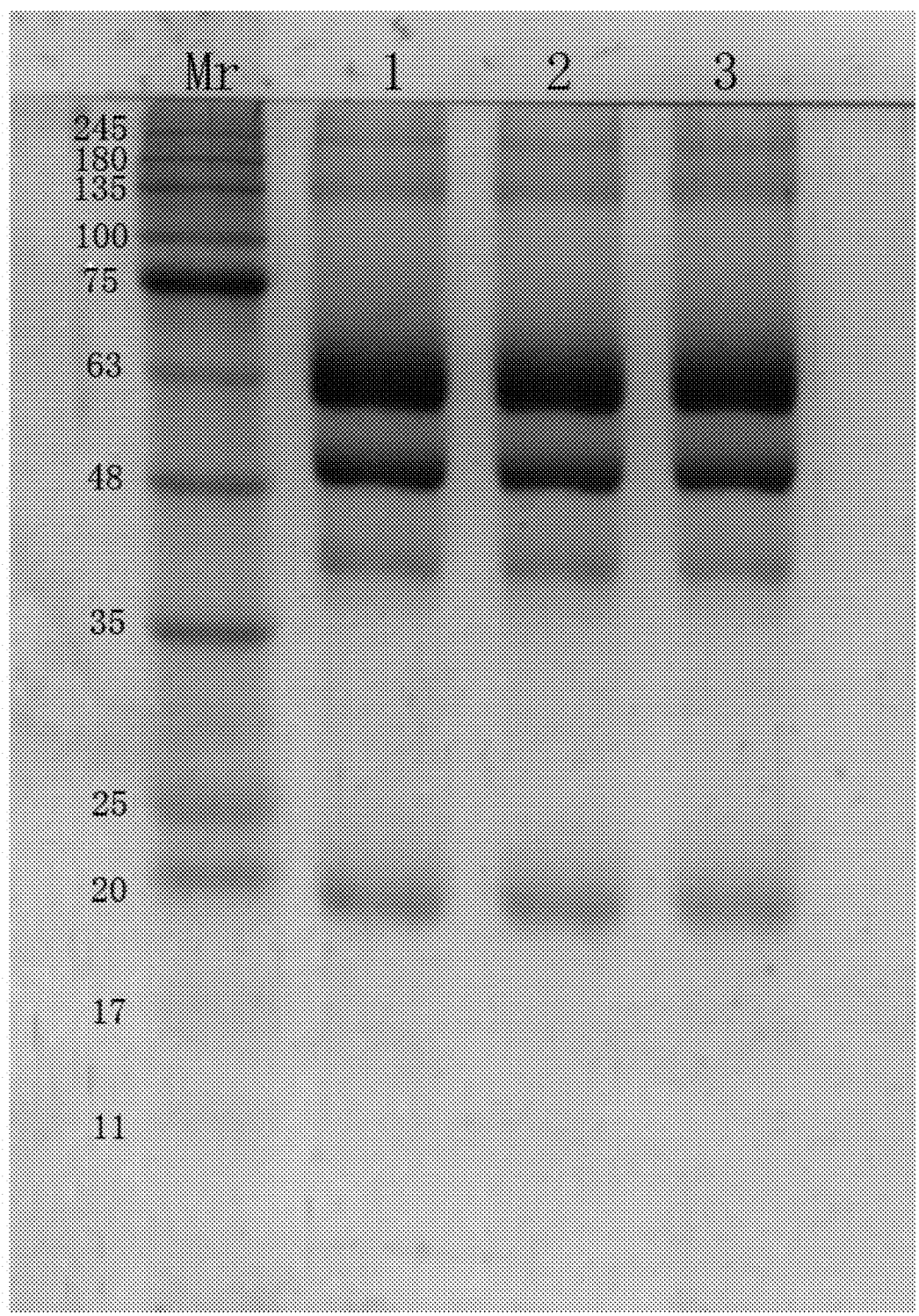
FIG. 6 shows the results of SDS-page electrophoresis of the virus stock solutions in three repeated experiments as described in Example 5 (rabies virus harvested from chicken embryo). Marker represents the reference sample that indicates molecular weight standard of proteins. The molecular weight of each band of the reference sample was marked in the left. Bands 1-3 represent the three independent tests of the virus stock solutions.

Samples of the vaccine stock solution were analyzed three times by SDS-polyacrylamide gel electrophoresis (SDS-PAGE). The gels were subject to silver staining to assess the virus antigen purity. Results were shown in Table 17. A representative picture of the SDS-page electrophoresis analysis was shown in FIG. 6. These results show that the virus antigen purity was higher than 95% in all three individual tests.

TABLE 17

Virus antigen purity analysis (virus harvested from chicken embryo).

| Test # | Antigen purity (%) |
|---|---|
| 1 | 95.600 |
| 2 | 95.737 |
| 3 | 95.989 |
| Average | 95.780 |

G. Preparation of Vaccine Formulation and Packaging

Vaccine formulation was prepared and packaged to final product as described in the methods and/or processes described in Example 3G.

H. Quality Test of the Vaccine Product

Since rabies vaccine harvested from chicken embryos has not been listed in the National Pharmacopoeia, the "freeze-dried human rabies vaccine (Vero cells)" product testing procedures and methods described in the General Principles in the "Pharmacopoeia of the People's Republic of China" in 2015 Volume III were used to assess the quality of the vaccine product. The results were shown in Table 18. According to the relevant provisions of vaccine product management in this country and abroad, the vaccine that was harvested from chicken embryos is not subject to the assessment of host cell DNA and protein residues.

TABLE 18

Quality analysis of the vaccine product (virus harvested from chicken embryo).

| Test | Standard | Result |
|---|---|---|
| Identification (e.g., ELISA) | Contains virus antigen | In compliance. |
| Appearance | White and loose in solid form. Clear solution after dissolved. No precipitation in the solution. | In compliance. |
| Osmolality (mOsmol/kg) | In compliance with the criteria | 384 |
| pH | 7.2~8.0 | 7.66 |
| Water content (%) | ≤3% | 2.57 |
| Potency (IU/dose) | ≥2.5 | 5.1 |

TABLE 18-continued

Quality analysis of the vaccine product (virus harvested from chicken embryo).

| Test | Standard | Result |
|---|---|---|
| Heat stability (IU/dose) | ≥2.5 | 2.7 |
| Bovine serum protein residue (ng/dose) | ≤50 | <1 |
| Sterility | In compliance with the criteria | In compliance |
| Uncommon toxicity | In compliance with the criteria | In compliance |
| Bacteria endotoxin (EU/dose) | ≤25 | <12.5 |

Example 6: Comparison of Rabies Vaccines Produced from Different Methods

Virus sample was harvested from Vero cells and purified by three different methods, two of which are the traditional methods generally used to purify rabies virus in the art: 1) a combination of ultrafiltration and ultracentrifugation; and 2) a combination of ultrafiltration and gel filtration. The third method was as described in the Example 1 (including both IE chromatography and HA chromatography). A vaccine stock solution was obtained from each method. A sample of each vaccine stock solution was reconstituted into a virus titer of 12.1 EU/ml and tested for protein content(s) by Lowry assay, protein residues from host cells by ELISA and DNA residues from host cells by hybridization technology (e.g., PCR). See Table 19.

TABLE 19

Comparison of rabies vaccines produced from different methods.

| Test | Ultrafiltration and ultracentrifugation | Ultrafiltration and gel filtration | Method described in Example 1 |
|---|---|---|---|
| Antigen titer (EU/ml) | 12.1 | 12.1 | 12.1 |
| Total protein content (µg/ml) | 125.47 | 179.82 | 50.00 |
| Host cell protein residues (µg/ml) | 17.3 | 24.6 | 1.5 |
| Host cell DNA residues (pg/ml) | >1000 | >1000 | 20-100 |

Example 7: Purification of Japanese Encephalitis Virus

In this example, the methods of isolating virus in the present application is demonstrated by applying the methods to biological samples collected from Vero cell culture in which the cells were infected with the P3 strain of the Japanese encephalitis virus.

A. Pretreatment of the Biological Samples

The collected biological samples were filtered through a microporous membrane filter with a pore size of 0.45 μm.

B. Anion Exchange ("AE") Chromatography

The filtered samples were then subjected to an AE chromatography under the following conditions. A Capto-DEAE column was first pre-equilibrated with a 20 mM phosphate buffer that had pH of 8.0. The filtered samples were then loaded to the column. After the loading, 2-5 column volumes of the 20 mM phosphate buffer that had pH of 8.0 were applied to the column for equilibrating the column. The column was then loaded with a 20 mM phosphate buffer that had pH of 8.0 and contains 50 mM NaCl to pre-elute the column. Following the pre-elution step, the column was loaded with a 20 mM phosphate buffer that had pH of 7.2 and contains 300 mM NaCl to elute the column. The eluate ("the AE eluate") was collected according to the light absorption peak(s) indicated by the chromatography detector.

C. Hydroxyapatite ("HA") Chromatography

The eluate A collected from the AE chromatography as described above was then subjected to an HA chromatography under the following conditions. A CHT column was first pre-equilibrated with a 5 mM phosphate buffer that had pH of 7.2. The eluate A was then loaded to the column. After the loading, 2-5 column volumes of the 5 mM phosphate buffer that had pH of 7.2 were applied to the column for equilibrating the column. The column was then loaded with a 5 mM phosphate buffer that had pH of 7.2 to pre-elute the column. Following the pre-elution step, the column was loaded with a 150 mM phosphate buffer that had a pH of 7.2, and the eluate ("the HA eluate") was collected according to the light absorption peak(s) indicated by the chromatography detector.

D. Results

Figure 7:
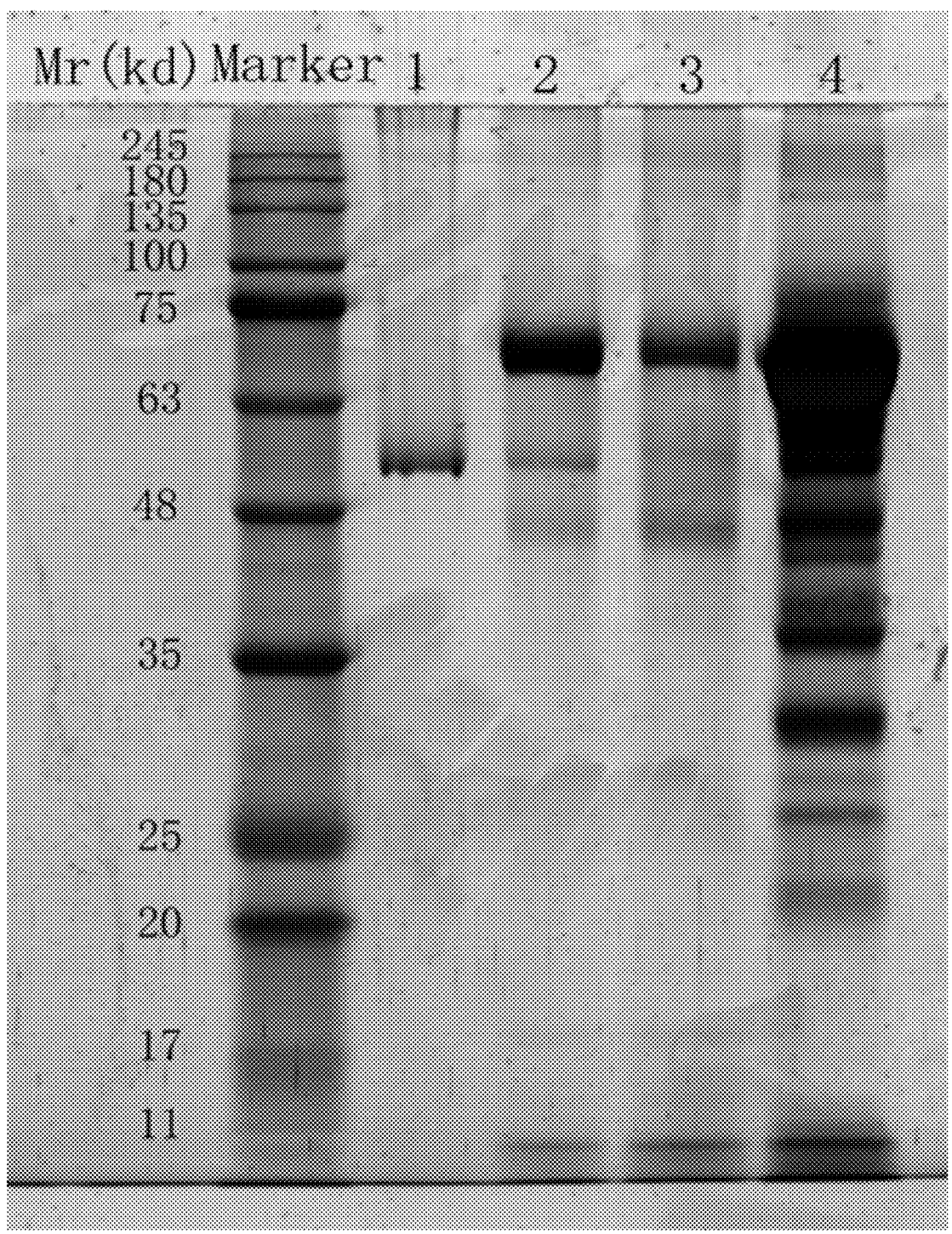
FIG. 7 shows the results of SDS-page electrophoresis of the Japan into the culture. Therefore, the host cell DNA in the virus harvest culture is also a complex mixture that includes many that are close to the virus particles in size. Another example is serum (e.g., bovine serum) which is used to supplement the culture medium. Importantly, another example is structural derivatives derived from the enveloped viruses themselves. During the virus harvest, a portion of the assembled virus particles are incomplete or less preferable. For examples, some virus particles have low copy numbers of outer membrane proteins, and/or have incomplete or less preferable glycosylation of outer membrane proteins. These virus particles may have comparable size as intact and/or preferable virus particles, but have significant differences in their biological functions and immunological properties (such as potency). As above, methods based upon molecular sieves (such as density gradient ultracentrifugation or gel filtration chromatography) are less satisfactory since they cannot successfully separate the intact and/or preferable virus particles from the impurities in comparable sizes such as those described above.

Samples of the vaccine stock solution obtained through the method described above were analyzed by SDS-polyacrylamide gel electrophoresis (SDS-PAGE) in comparison with the samples obtained through traditional method #1 (gel filtration) and samples obtained through traditional #2 (ultracentrifugation). The gels were subject to silver staining to assess the virus antigen purity. A representative picture of the SDS-page electrophoresis analysis was shown in FIG. 7. Compared with traditional method #1 (lane #2) and method #2 (land #3), the method of the present invention has only one band (lane #1), indicating that the sample contained almost no impurities and has achieved excellent effects of separation and purification.

Figure 8:
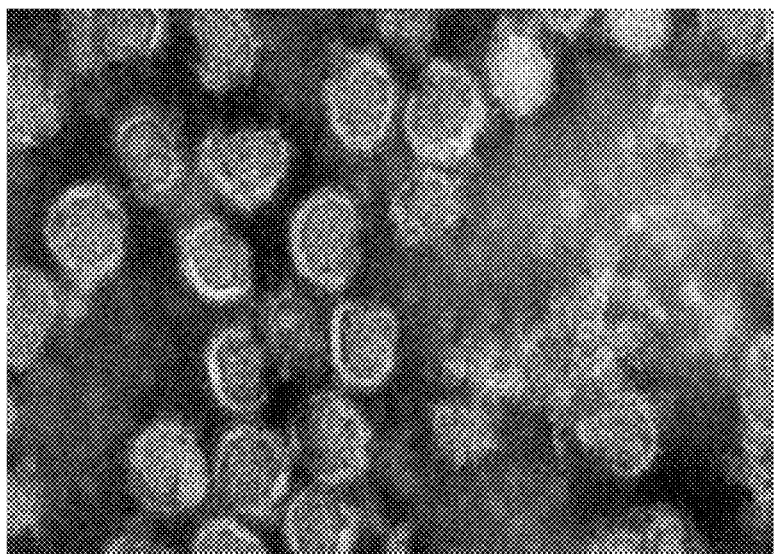

Electron microscopy was used for observing virus particle in the vaccine stock solution obtained using the method described in this Example. The electron micrograph in FIG. 8 showed Japanese encephalitis virus particles with intact structure and typical round-shaped morphology. The morphology of different virus particles has no significant differences. The results further illustrate that the methods of the present application can be used to isolate and/or purify highly homogenous intact virus particles.

Example 8: Purification of Influenza Virus

In this example, the methods of isolating virus in the present application is demonstrated by applying the methods to biological samples collected from chicken embryo tissues in which the cells were infected with the H1N1 strain of the influenza virus.

A. Pretreatment of the Biological Samples

The collected biological samples were filtered through a microporous membrane filter with a pore size of 1.2 μm.

B. Anion Exchange ("AE") Chromatography

The filtered samples were then subjected to an AE chromatography under the following conditions. A Capto-DEAE column was first pre-equilibrated with a 20 mM phosphate buffer that had pH of 7.6. The filtered samples were then loaded to the column. After the loading, 2-5 column volumes of the 20 mM phosphate buffer that had pH of 7.6 were applied to the column for equilibrating the column. The column was then loaded with a 20 mM phosphate buffer that had pH of 7.6 and contains 120 mM NaCl to pre-elute the column. Following the pre-elution step, the column was loaded with a 20 mM phosphate buffer that had pH of 7.6 and contains 500 mM NaCl to elute the column. The eluate ("the AE eluate") was collected according to the light absorption peak(s) indicated by the chromatography detector.

C. Hydroxyapatite ("HA") Chromatography

The eluate A collected from the AE chromatography as described above was then subjected to an HA chromatography under the following conditions. A CHT column was first pre-equilibrated with a 20 mM phosphate buffer that had pH of 7.6. The eluate A was then loaded to the column. After the loading, 2-5 column volumes of the 20 mM phosphate buffer that had pH of 7.6 were applied to the column for equilibrating the column. The column was then loaded with a 20 mM phosphate buffer that had pH of 7.6 to pre-elute the column. Following the pre-elution step, the column was loaded with a 200 mM phosphate buffer that had a pH of 7.6, and the eluate ("the HA eluate") was collected according to the light absorption peak(s) indicated by the chromatography detector.

D. Results

Figure 9:
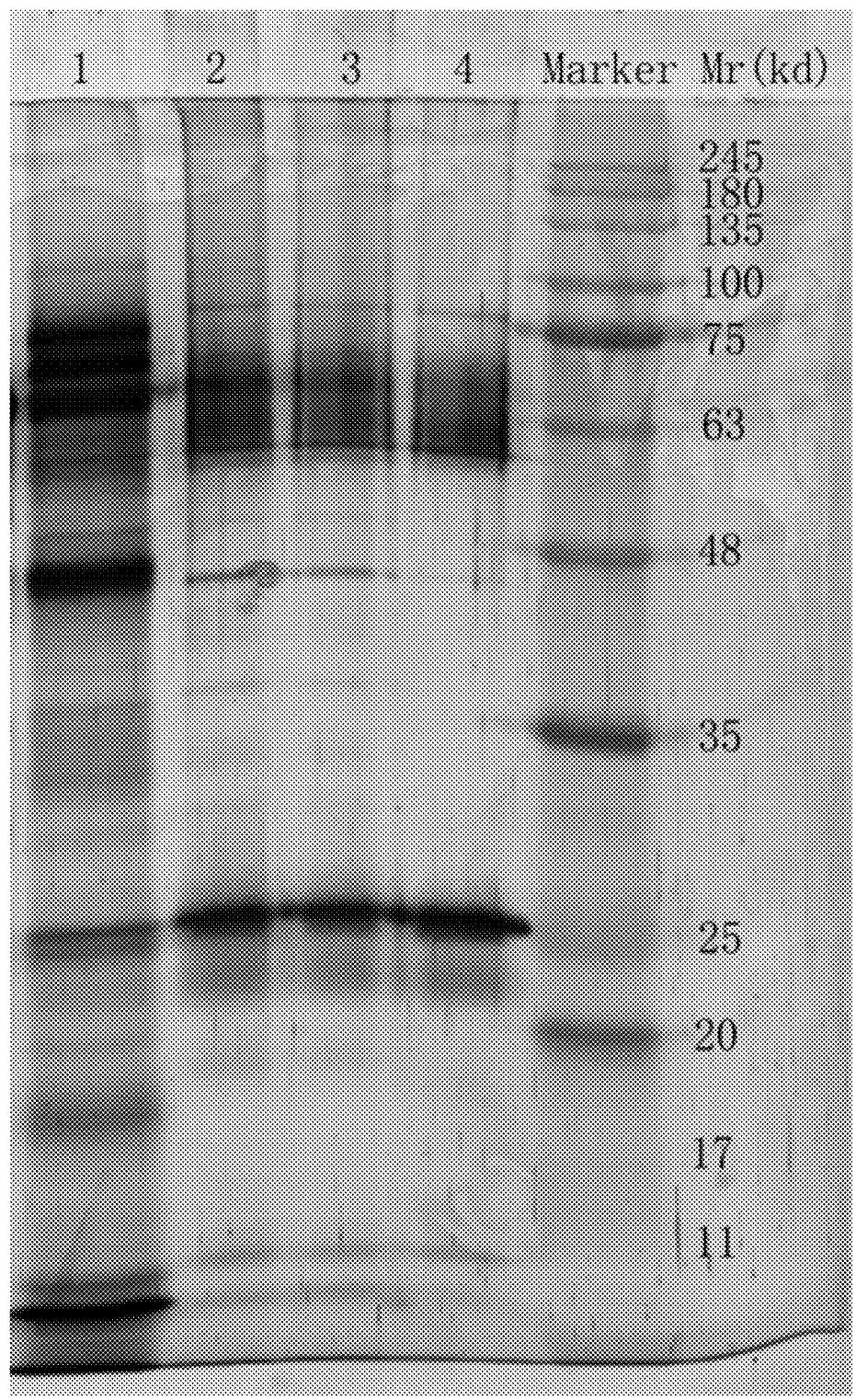

Samples of the vaccine stock solution obtained through the method described above were analyzed by SDS-polyacrylamide gel electrophoresis (SDS-PAGE) in comparison with the samples obtained through traditional method #1 (gel filtration) and samples obtained through traditional #2 (ultracentrifugation). The gels were subject to silver staining to assess the virus antigen purity. A representative picture of the SDS-page electrophoresis analysis was shown in FIG. 9. The results showed that the impurities were significantly reduced, while the concentration of virus-related proteins was significantly increased.

Figure 10:
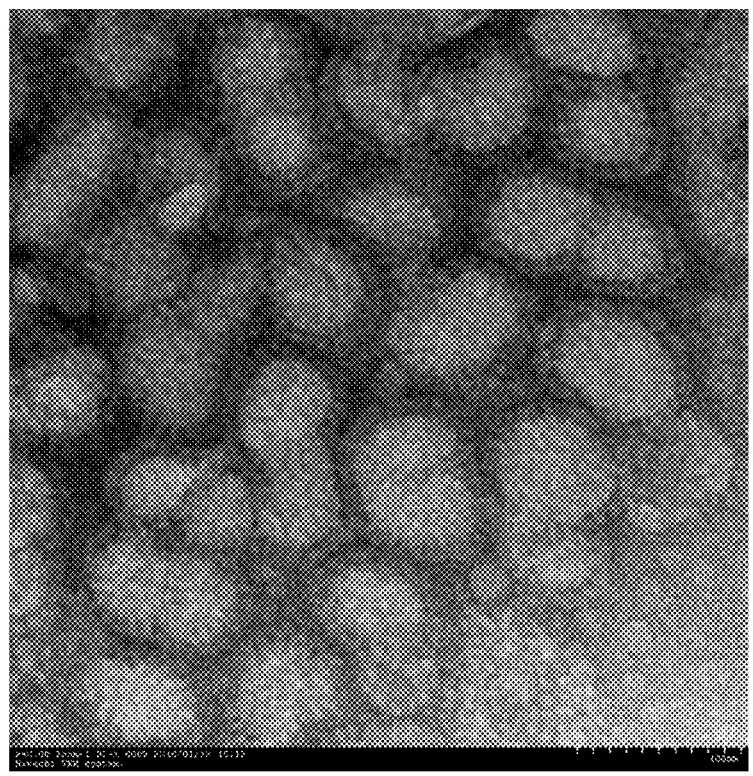

Electron microscopy was used for observing virus particle in the vaccine stock solution obtained using the method described in this Example. The electron micrograph in FIG. 10 showed influenza virus particles with intact structure and typical influenza virus morphology. The morphology of different virus particles has no significant differences. The results further illustrate that the methods of the present application can be used to isolate and/or purify highly homogenous intact virus particles.

Isolation and/or purification of other enveloped viruses such as measles virus, rubella virus, varicella, mumps virus, dengue virus or HIV can also be achieved using the methods of the present application without making substantive modifications to the methods disclosed in the above examples.

Example 9: Vaccine Formulation

A. Vaccine Formulation and Lyophilization

The purified virus vaccine was formulated to a vaccine stock solution with human serum albumin at a weight ratio (w/w) of 1.5%, sucrose at a weight ratio (w/w) of 5.0%, and a phosphate buffer that had pH of 7.2-8.0.

The vaccine stock solution was packaged into 2 ml glass tubes with a volume of 0.5 ml per tube, and then lyophilized in a freeze dryer.

B. Assessment of the Vaccine Product

1) The Potency Loss after Lyophilization

The potency of vaccine stock solution and the lyophilized vaccine product were measured to calculate the potency loss rate during the lyophilization. See Table 19. The potency loss rate is within the acceptable range.

TABLE 19

Comparison of potency between vaccine stock solution and the lyophilized vaccine product.

| Potency (IU/ml) | | |
| --- | --- | --- |
| Pre-lyophilization | Post-lyophilization | Potency loss rate. |
| 13.7 | 10.8 | 21.2% |

2) Assessment of Lyophilized Vaccine Product a) Potency, Water Content, and Uncommon Toxicity The potency, water content and uncommon toxicity of the lyophilized vaccine were assessed according to the following methods or rules. Potency was assessed according to Rule No. 3503 of the General Rules in the Volume 3 of the Pharmacopoeia of the People's Republic of China published in 2015. Water content was assessed according to Rule No. 0832 of the General Rules the Volume 3 of the Pharmacopoeia of the People's Republic of China published in 2015. Uncommon toxicity was assessed according to Rule No. 1141 of the General Rules in the Volume 3 of the Pharmacopoeia of the People's Republic of China published in 2015. See Table 20.

TABLE 20

Quality assessment of the lyophilized vaccine product.

| Test | Result |
| --- | --- |
| Potency (IU/dose) | 10.8 |
| Water content | 1.8% |
| Uncommon toxicity | In compliance | b) Heat Stability

To test the heat stability, samples of the vaccine product were incubated in 37±1° C. for 4, 5, and 6 weeks, respectively. The samples before incubation and the ones obtained at each time point after incubation were administered to mice and the potency was measured by the NIH test.

TABLE 21

Heat stability of the lyophilized vaccine product

| Time point | Potency IU/dose | Potency loss rate |
| --- | --- | --- |
| 0 | 5.4 | / |
| 4 weeks | 4.1 | 24.1% |
| 5 weeks | 3.8 | 29.6% |
| 6 weeks | 3.4 | 37.0% |

The results show that the lyophilized vaccine product still had a potency more than 2.5 IU/dose six weeks after incubated in 37° C., which was in compliance with the relevant requirements in the Volume 3 of the Pharmacopoeia of the People's Republic of China published in 2015.

c) Long Term Stability

To test the long term stability, sample of the vaccine product was stored in 4±2° C. for 3 months, 6 months, and 9 months, respectively. The samples before storage and the ones obtained at each time point after storage were administered to mice and the potency was measured by the NIH test after administration. See Table 22.

TABLE 22

Long term stability of the lyophilized vaccine product.

| Time point | Potency IU/dose | Potency loss |
| --- | --- | --- |
| 0 | 5.4 | |
| 3 months | 5.2 | 3.7% |
| 6 months | 5.0 | 7.4% |
| 9 months | 4.8 | 11.1% |

C. The Effect of Sucrose on the Lyophilized Vaccine Formulation

To study the effect of sucrose on the lyophilized vaccine formulation, different concentrations of sucrose were tested, including 1%, 3%, 5% and 10%. The concentration of human serum albumin was 1.5% in all the tests. The appearance, re-dissolution time, and water content of the produced vaccine formulations were assessed. See Table 23.

TABLE 23

Lyophilized vaccine formulation with different concentrations of sucrose

| Sucrose concentration (%) | Appearance (in solid form) | Re-dissolution time (seconds) | Water content (%) |
| --- | --- | --- | --- |
| 1 | White and loose, slightly larger pores. | <10 s | 1.5% |
| 3 | White and loose | <10 s | 1.5% |
| 5 | White and loose | <10 s | 1.8% |
| 10 | White and loose | <20 s | 2.4% |

The results showed that the appearance, the re-dissolution time and the water content of the lyophilized vaccine formulations with 1-10% sucrose all met the requirements in the Pharmacopoeia of the People's Republic of China published in 2015. The results also suggested that lyophilized vaccine formulations with 3-5% sucrose have superior appearances and re-dissolution time.

D. The Effect of Human Serum Albumin on the Vaccine Formulation

To study the effect of human serum albumin on the vaccine formulation, different concentrations of human serum albumin were tested, including 0.3%, 0.5%, 1.5%, 3% and 5%. The concentration of sucrose was 5% in all the tests. The appearance, re-dissolution time, and water content of the produced vaccine formulations were assessed. See Table 24.

TABLE 24

Vaccine formulations with different concentrations of human serum albumin.

| Human serum albumin concentration (%) | Appearance (in solid form) | Re-dissolution time (seconds) | Water content (%) |
| --- | --- | --- | --- |
| 0.3 | Deficiency of solid matter, shrinkage | <30 s | 2.1% |
| 0.5 | Water and loose, slightly larger pores | <10 s | 1.5% |
| 1.5 | White and loose | <10 s | 1.5% |
| 3 | White and loose | <10 s | 1.8% |
| 5 | White and loose | <10 s | 2.4% |

The results showed that the lyophilized vaccine formulations with 0.5-5% human serum albumin had preferable appearances, while the one with 0.3% human serum albumin had less preferable appearances.

The invention claimed is:

1. A virus composition comprising inactivated rabies virus particles, wherein at least about 90% of the total proteins in the composition are viral proteins,
wherein the viral proteins comprise: at least about 35-48% protein G.

2. The virus composition of claim 1, wherein the virus proteins further comprise:
about 28-37% protein N;
about 8-12% protein P; and
about 13-16% protein M.

3. The virus composition of claim 2, wherein the composition is substantially free of non-viral DNA.

4. The virus composition of claim 2, wherein the composition has a potency of at least about 4 IU/dose or 4 IU/25 µg.

5. The virus composition of claim 2, wherein the composition is stable for at least about 1, 2, 3, 4, 5, 6, 7, 8, or 9 months at room temperature or under a refrigerated condition.

6. The virus composition of claim 2, wherein pH of the composition is about 7.5-7.7.

7. The virus composition of claim 2, wherein the composition is white when it is solid, and wherein a solution of the composition is clear.

8. The virus composition of claim 2, wherein the water content of the composition is less than 3%.

9. The virus composition of claim 2, wherein the potency of the composition under long term stability test is at least about 4 IU/dose or 4 IU/25 µg.

10. The virus composition of claim 2, wherein the potency of the composition under heat stability test is at least 3 IU/dose.

11. The virus composition of claim 1, wherein at least about 80% of the rabies virus particles in the composition are intact viral particles.

12. The composition of claim 1, wherein at least about 95% of the total proteins in the composition are viral proteins.

13. The composition of claim 1, the total viral proteins comprise at least about 40% or at least about 45% protein G.

14. A virus composition comprising inactivated rabies virus particles comprising viral proteins, wherein the virus composition has at least about 80% purity of the rabies virus, wherein the purity is calculated by totaling proportions of all viral proteins based upon silver staining of SDS-PAGE analysis of the virus composition, wherein the viral proteins comprise: at least about 35-48% protein G.

15. The composition of claim 14, the total viral proteins comprise at least about 40% or at least about 45% protein G.

16. The composition of claim 14, wherein the virus composition has at least about 90% purity of the rabies virus.

17. The composition of claim 14, wherein the virus composition has at least about 95% purity of the rabies virus.

18. The composition of claim 14, wherein the viral proteins further comprise about 28-37% protein N; about 8-12% protein P; or about 13-16% protein M.

19. The composition of claim 14, wherein the viral proteins further comprise about 28-37% protein N; about 8-12% protein P; and about 13-16% protein M.

20. The composition of claim 19, wherein the composition is a virus vaccine composition.

21. A commercial batch of the virus vaccine composition of claim 20.

22. A virus composition comprising inactivated rabies virus particles comprising viral proteins,
wherein the total viral proteins comprise 35-48% protein G and 13-16% protein M.

23. The composition of claim 22, the total viral proteins comprise at least about 40% protein G.

24. The composition of claim 23, the total viral proteins comprise at least about 45% protein G.

25. The composition of claim 22, wherein the total viral proteins comprise 28-37% protein N and/or 8-12% protein M.

26. The composition of claim 22, wherein the composition is a virus vaccine composition.

27. A commercial batch of the virus vaccine composition of claim 22.

28. The virus composition of claim 22, wherein the composition comprises bovine serum albumin (BSA), wherein the bovine serum albumin content is less than about 10 ng/dose.

29. The virus composition of claim 22, wherein the composition is lyophilized.

30. A virus composition produced by combining a virus stock solution with a stabilizer, wherein the stock solution comprises rabies virus particles,
wherein at least about 90% of the total proteins in the stock solution are viral proteins,
wherein the viral proteins comprise: at least about 35-48% protein G.

31. The virus composition of claim 30, wherein the stabilizer comprises sucrose, albumin, or sucrose and albumin.

* * * * *